(12) United States Patent
Dixit et al.

(10) Patent No.: US 12,390,416 B2
(45) Date of Patent: *Aug. 19, 2025

(54) CHEWABLE PHARMACEUTICAL DOSAGE FORMS

(71) Applicant: USpharma Ltd, Miami Lakes, FL (US)

(72) Inventors: Manesh A Dixit, Miami Lakes, FL (US); Rahul Botkar, Maharashtra (IN); Partha S Sen, Valsad (IN)

(73) Assignee: USPHARMA LTD, Miami Lakes, FL (US)

( * ) Notice: Subject to any disclaimer, the term of this patent is extended or adjusted under 35 U.S.C. 154(b) by 650 days.

This patent is subject to a terminal disclaimer.

(21) Appl. No.: 17/679,192

(22) Filed: Feb. 24, 2022

(65) Prior Publication Data

US 2022/0183970 A1 Jun. 16, 2022

Related U.S. Application Data

(63) Continuation-in-part of application No. 16/515,982, filed on Jul. 18, 2019, now Pat. No. 11,273,123.

(60) Provisional application No. 62/831,500, filed on Apr. 9, 2019, provisional application No. 62/700,149, filed on Jul. 18, 2018.

(51) Int. Cl.
| | | |
|---|---|---|
| *A61K 9/00* | (2006.01) |
| *A61K 9/06* | (2006.01) |
| *A61K 45/06* | (2006.01) |
| *A61K 47/02* | (2006.01) |
| *A61K 47/10* | (2017.01) |
| *A61K 47/26* | (2006.01) |

(52) U.S. Cl.
CPC .............. *A61K 9/0056* (2013.01); *A61K 9/06* (2013.01); *A61K 45/06* (2013.01); *A61K 47/02* (2013.01); *A61K 47/10* (2013.01); *A61K 47/26* (2013.01)

(58) Field of Classification Search
CPC ........ A61K 9/0056; A61K 9/06; A61K 45/06; A61K 47/02; A61K 47/10; A61K 47/26
See application file for complete search history.

(56) References Cited

U.S. PATENT DOCUMENTS

| | | | |
|---|---|---|---|
| 4,894,441 A | 1/1990 | Menicagli |
| 5,837,272 A | 11/1998 | Fierro, Jr. |
| 5,928,664 A | 7/1999 | Yang |
| 8,097,279 B2 | 1/2012 | Hassan |
| 8,496,977 B2 | 7/2013 | Medasani |
| 8,541,383 B2 | 9/2013 | Gokaraju |
| 8,802,164 B2 | 8/2014 | Shimoda |
| 9,072,677 B2 | 7/2015 | Hassan et al. |
| 9,167,831 B2 | 10/2015 | Subramanian et al. |
| 9,616,121 B2 | 4/2017 | Agrawal |
| 9,757,332 B2 | 9/2017 | Kitanaka et al. |
| 9,764,032 B2 | 9/2017 | Moshtagh |
| 9,855,288 B2 | 1/2018 | Sinnott et al. |
| 9,993,447 B2 | 6/2018 | Alevizache et al. |
| 11,273,123 B2 * | 3/2022 | Dixit .................... A61K 31/138 |
| 2002/0086068 A1 | 7/2002 | Bandyopadhyay |
| 2003/0044456 A1 | 3/2003 | Ichie |
| 2004/0028622 A1 | 2/2004 | Gurin |
| 2006/0228412 A1 | 10/2006 | Dunn |
| 2007/0269386 A1 | 11/2007 | Steen |
| 2008/0026038 A1 | 1/2008 | Steele |
| 2008/0125394 A1 | 5/2008 | Savica |
| 2008/0286252 A1 | 11/2008 | Sinnott |
| 2009/0130199 A1 | 5/2009 | Kovacs |
| 2009/0155189 A1 | 6/2009 | Kovacs |
| 2010/0203078 A1 | 8/2010 | Gokaraju |
| 2010/0226904 A1 | 9/2010 | Davis |
| 2010/0330058 A1 | 12/2010 | Davis |
| 2011/0044964 A1 | 2/2011 | Davis |
| 2011/0071119 A1 | 3/2011 | Davis |
| 2011/0313055 A1 | 12/2011 | Ervin |
| 2012/0061280 A1 | 3/2012 | Cooperman |
| 2013/0005740 A1* | 1/2013 | Lowther ................. A23L 29/20 514/630 |
| 2013/0109671 A1 | 5/2013 | Gedulin et al. |
| 2013/0338093 A1 | 12/2013 | Gedulin et al. |
| 2014/0212453 A1 | 7/2014 | Chang |

(Continued)

FOREIGN PATENT DOCUMENTS

| | | |
|---|---|---|
| WO | WO2010101588 A1 | 9/2010 |
| WO | WO2010151275 A1 | 12/2010 |

(Continued)

OTHER PUBLICATIONS

J.E. Henney, C.L. Taylor, and C.S. Boon, Editors, Chapter 4, pp. 91-92, of "Strategies to Reduce Sodium Intake in the United States," Washington, D.C.: The National Academies Press, 2010 (Year: 2010).*

J. Pitha, J. Milecki, and H. Fales. Hydroxypropyl b-cyclodextrin: preparation and characterization; effects on solubility of drugs, International Journal of Pharmaceutics, 29 (1986) 73-82. (Year: 1986).*

European Paediatric Formulation Initiative The 3rd Annual Conference of the EuPFI—Abstracts For Oral Presentations—Topic: Age appropriateness of Formulations—Development and Analysis of Medicated Soft Chew Dosage Form Suitable For Paediatric Use p. 14—2nd Column Sep. 2010; Berlin, Germany.

*Primary Examiner* — Michael P Cohen
(74) *Attorney, Agent, or Firm* — West Law Office LLC

(57) ABSTRACT

One aspect of the present invention concerns compositions and methods of manufacturing translucent chewable gels that are pharmaceutically suitable for oral administration. The chewable gels includes an active pharmaceutical ingredient and a complexing agent. The active pharmaceutical ingredient has a bitter taste. The active pharmaceutical ingredient and the complexing agent are complexed in the form of an inclusion complex. The chewable gels are substantially devoid of bitter taste and/or a tendency to cause oral numbness when chewed.

15 Claims, 24 Drawing Sheets

(56) References Cited

U.S. PATENT DOCUMENTS

| | | |
|---|---|---|
| 2014/0308374 A1 | 10/2014 | Goel |
| 2015/0290128 A1 | 10/2015 | Fernandez |
| 2015/0306029 A1 | 10/2015 | Fernandez et al. |
| 2015/0374660 A1 | 12/2015 | Goel |
| 2016/0015777 A1 | 1/2016 | Traylor |
| 2016/0067180 A1 | 3/2016 | Westhusing et al. |
| 2016/0067340 A1 | 3/2016 | Westhusing et al. |
| 2016/0089363 A1 | 3/2016 | Borody |
| 2016/0151279 A1 | 6/2016 | Westhusing et al. |
| 2016/0296470 A1 | 10/2016 | Romanoschi et al. |
| 2016/0310518 A1 | 10/2016 | Gedulin et al. |
| 2017/0157042 A1 | 6/2017 | Fernandez et al. |
| 2017/0173067 A1 | 6/2017 | Sinnott |
| 2017/0209369 A1 | 7/2017 | Westhusing et al. |
| 2017/0209370 A1 | 7/2017 | Westhusing et al. |
| 2017/0251692 A1 * | 9/2017 | Yaranossian .......... A23L 29/256 |
| 2017/0274071 A1 | 9/2017 | Agrawal |
| 2017/0368085 A1 | 12/2017 | Gedulin et al. |
| 2018/0071268 A1 | 3/2018 | Borody |
| 2018/0168182 A1 | 6/2018 | Majeed |
| 2018/0177804 A1 | 6/2018 | Papas et al. |
| 2018/0263904 A1 | 9/2018 | Sirihorachai et al. |

FOREIGN PATENT DOCUMENTS

| | | |
|---|---|---|
| WO | WO2011028314 A1 | 3/2011 |
| WO | WO2011034644 A1 | 3/2011 |
| WO | WO2016164470 A1 | 10/2016 |
| WO | WO2018027070 A1 | 2/2018 |
| WO | WO2018027081 A1 | 2/2018 |
| WO | WO2018027083 A1 | 2/2018 |
| WO | WO2018027127 A1 | 2/2018 |
| WO | WO2018236990 A1 | 12/2018 |
| WO | WO2018237000 A1 | 12/2018 |
| WO | WO2019140403 A1 | 7/2019 |
| WO | WO2019140406 A1 | 7/2019 |
| WO | WO2019241146 A1 | 12/2019 |
| WO | WO2019241583 A1 | 12/2019 |

* cited by examiner

CHEWABLE PHARMACEUTICAL DOSAGE FORMS

RELATED APPLICATIONS

The present application is a continuation-in-part of U.S. patent application Ser. No. 16/515,982 filed Jul. 18, 2019, entitled CHEWABLE PHARMACEUTICAL DOSAGE FORMS, which claims the benefit of U.S. Provisional Patent Application Ser. No. 62/700,149, filed Jul. 18, 2018, entitled Chewable Pharmaceutical Dosage Forms and U.S. Provisional Patent Application Ser. No. 62/831,500, filed Apr. 9, 2019, entitled Chewable Pharmaceutical Dosage Forms, each of which is hereby incorporated in its entirety by reference herein.

BACKGROUND

1. Field

The present invention relates generally to pharmaceutical products for human and animal use. More particularly, the present invention relates to orally consumable pharmaceutical products and methods of manufacturing the same. Even more particularly, the present invention relates to chewable pharmaceutical oral dosage forms, including chewable gels. As defined by the United States Pharmacopeia: "[c]hewable gels are used to deliver drug substances or dietary supplements via the oral route. In addition to drug substances(s) or dietary supplements, chewable gels can consist of all or some of the following components: gelling agent(s), sugars, water, sweeteners, and flavoring agents. The sweeteners and flavoring are intended to enhance patient acceptance and mask the taste of the delivered labeled drug substance or dietary supplement. Chewable gels maintain their molded shape, are elastic, and yield to mastication. They are intended to be chewed before swallowing. Chewable gels are also known as "gummies" in the confectionary and dietary supplement industries."

2. Discussion of Prior Art

Chewable oral dosage forms can be an effective way to administer drugs to those who are unable (or unwilling) to swallow traditional oral dosage forms. Known chewable dosage forms tend to lack certain organoleptic properties and are perceived by many patients as being dry, gritty, dusty, and/or bad tasting. Chewable gels could be a suitable alternative; however, chewable gels known in the art are difficult to manufacture (especially on a large scale) and/or suffer from an inability to consistently satisfy generally accepted regulatory standards. Further, many active pharmaceutical ingredients have tastes that are strongly disagreeable, something which manufactures of known chewable gels have failed to overcome. Thus, there is a need for pleasant tasting chewable gels that: include active pharmaceutical ingredients; are capable of commercially viable manufacture; and consistently satisfy generally accepted regulatory standards.

SUMMARY OF THE INVENTION

One aspect of the present invention concerns chewable gels that can both be manufactured using commercially viable methods (e.g., in commercial batch sizes, etc.) and satisfy generally accepted regulatory standards (e.g., are pharmaceutically suitable) for chewable oral dosage forms.

One aspect of the present invention concerns compositions and methods of manufacturing a translucent chewable gel that is pharmaceutically suitable for oral administration. The chewable gel includes a water insoluble active pharmaceutical ingredient and a complexing agent. The water insoluble active pharmaceutical ingredient has a bitter taste. The water insoluble active pharmaceutical ingredient and the complexing agent are complexed in the form of an inclusion complex. The chewable gel is substantially devoid of bitter taste when chewed.

One aspect of the present invention concerns compositions and methods of manufacturing a translucent chewable gel that is pharmaceutically suitable for oral administration. The chewable gel includes a water soluble active pharmaceutical ingredient and a complexing agent. The water soluble active pharmaceutical ingredient has a bitter taste and a tendency to cause oral numbness. The water soluble active pharmaceutical ingredient and the complexing agent are complexed in the form of an inclusion complex. The chewable gel is substantially devoid of bitter taste and tendency to cause oral numbness when chewed.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Figure 23:
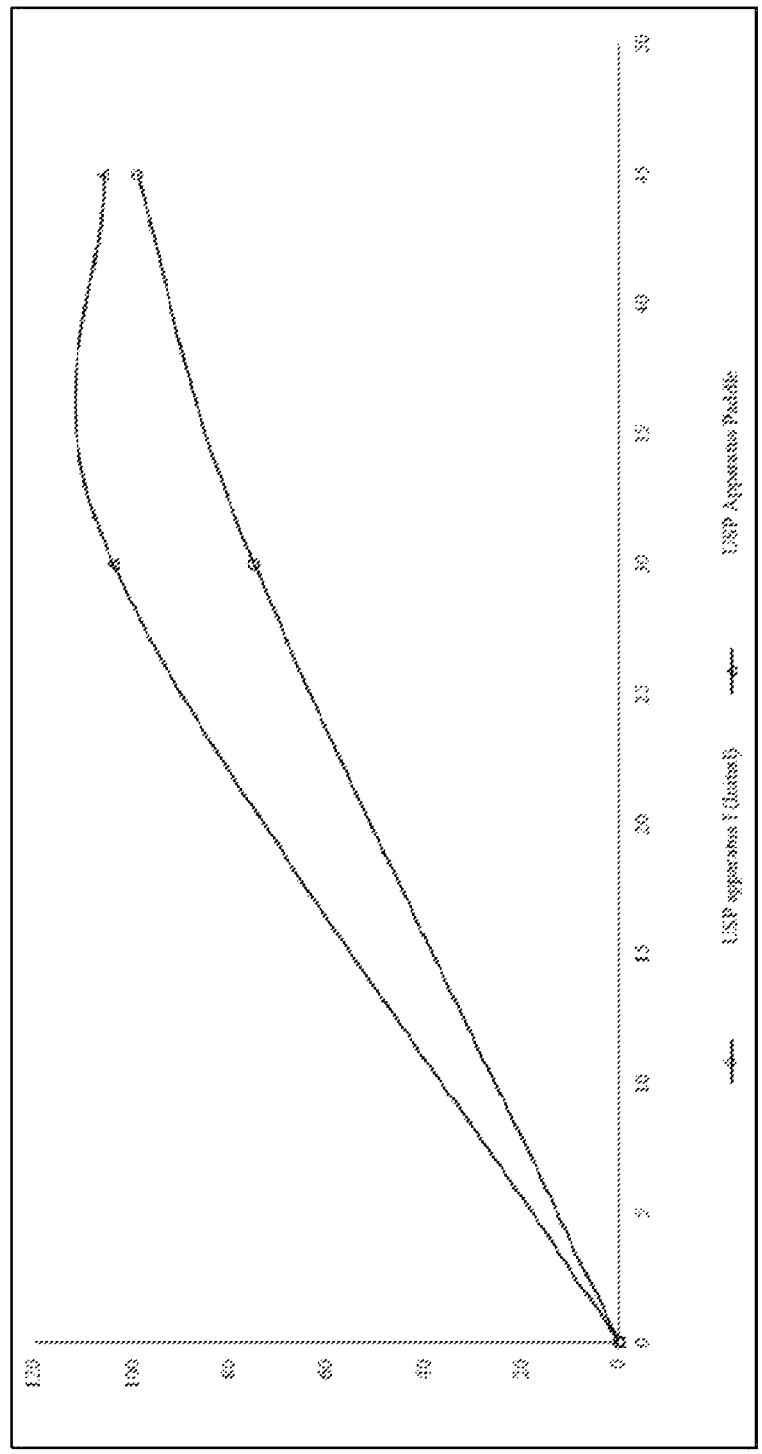
Figure 24:
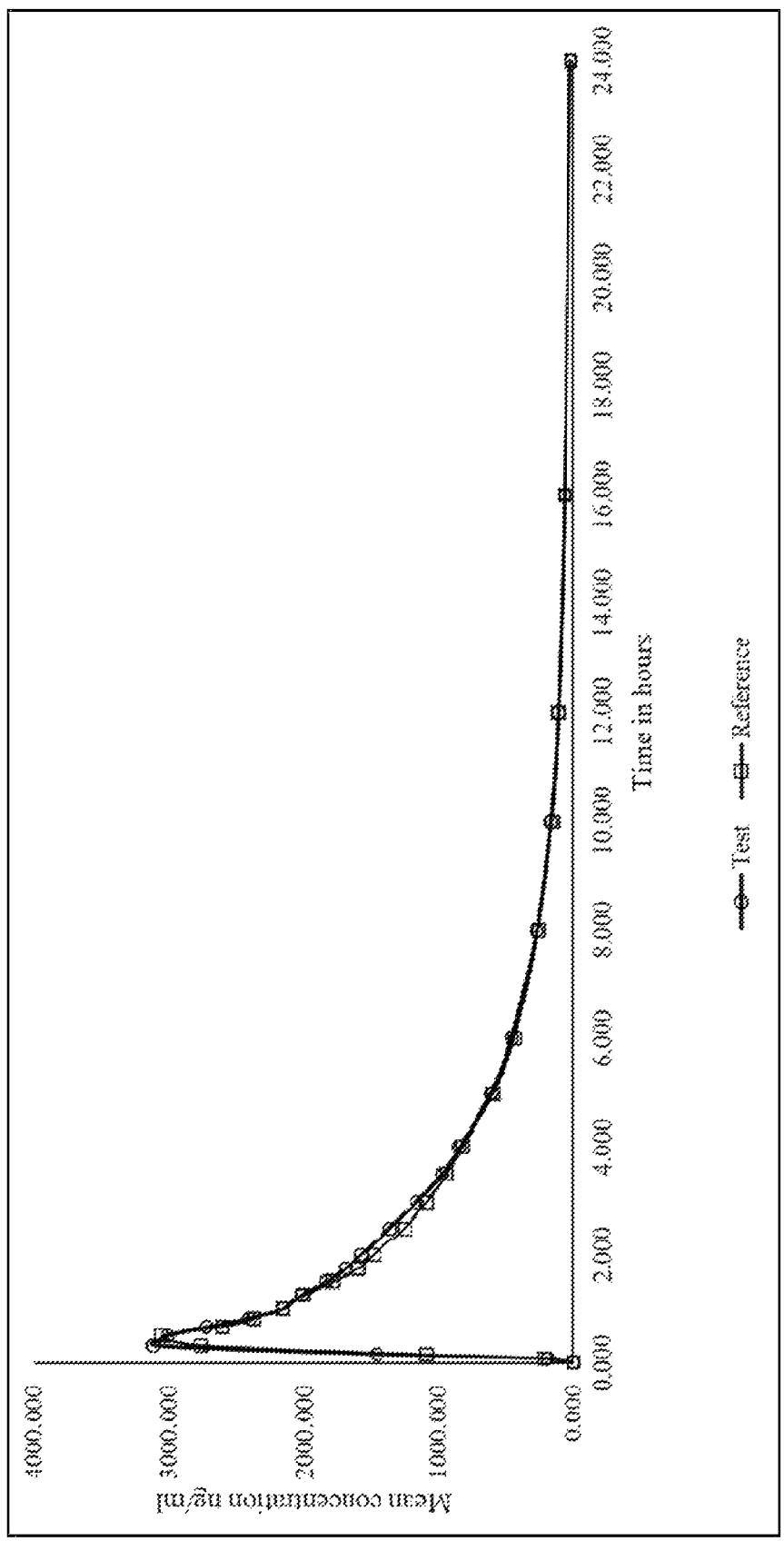

FIG. 23 is a chart showing comparative dissolution profiles (% cumulative average drug released vs. time in minutes) of chewable gel units formed in accordance with Example 14 analyzed using two (2) different apparatuses; and FIG. 24 is a chart showing comparative mean serum drug concentrations over a 24-hour period with respect to the chewable gel units formed in accordance with Example 16 and a reference marketed product.

The figures do not limit the present invention to the specific embodiments disclosed and described herein. The emphasis instead being placed upon clearly illustrating certain principles of the present invention.

DETAILED DESCRIPTION OF THE PREFERRED EMBODIMENTS

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

The terms and phrases "gummy pharmaceutical dosage form," "gummy," "gummy dosage form," "chewable gel," and plural versions thereof as used herein have interchangeable meanings and shall be interpreted to have the same meaning as "chewable gel" as defined by United States Pharmacopeia and National Formulary General Chapter (1151), which is incorporated herein by reference in its entirety.

In certain embodiments of the present invention, the composition of the chewable gel may include one or more the following components: functional ingredients; active ingredients; complexing agents; co-solvents; gelling agents; non-crystallizing polyol solutions; recrystallization inhibitors; lubricants (release agents); flavors; taste enhancing agents; and/or other additives.

In certain embodiments of the present invention, the composition of the chewable gel has an active ingredient content ranging from about one-tenth of one percent-by-weight (0.1% w/w) to about ten percent-by-weight (10% w/w). As used herein, the phrase "percent-by-weight" (% w/w) refers to the amount/concentration of one or more components in a group of components. The percent-by-weight (% w/w) of one or more components in a group of components can be calculated by dividing the numerical value for the weight of one or more components in a group of components by the numerical value for the weight of all of the components in the group and multiplying the quotient by one-hundred (100).

An active pharmaceutical ingredient (also referred to as active ingredient, pharmaceutically active agent, pharmaceutically acceptable active ingredient, drug, or active drug) for use in the process or product according to the current invention is a substance used in a pharmaceutical dosage form, intended to furnish pharmacological activity or to otherwise have direct effect in the diagnosis, cure, mitigation, treatment, and/or prevention of disease. Active ingredients also include compounds that have, or are thought to have, a direct effect in restoring, correcting, or modifying physiological functions in a patient population (humans or animals).

As used herein, the phrase "functional ingredient" includes, but is not limited to, minerals, vitamins, nutraceutical agents, and other supplements; including derivatives, salts (and the like), and/or mixtures of the foregoing. A "functional/active" refers to both a functional ingredient and active pharmaceutical ingredient. As used herein, the phrase "pharmaceutically acceptable salt(s)" refers to salt(s) that retain the desired biological activity of the parent compound and exhibit minimal undesired toxicological effects.

Although certain ingredients, such as acetaminophen, diphenhydramine hydrochloride ("diphenhydramine HCl"), azithromycin, ibuprofen, dimenhydrinate, amphetamine, fexofenadine hydrochloride ("fexofenadine HCl"), aspirin, dextromethorphan hydrobromide ("dextromethorphan HBr"), amoxicillin, cetirizine hydrochloride ("cetirizine HCl"), loratadine, phenylephrine hydrochloride ("phenylephrine HCl"), and/or methylphenidate, may appear in the examples provided below, it will be understood by those having ordinary skill in the art that other types of active ingredients (and/or functional ingredients) are within the scope of the present invention and that other active ingredients may be used without departing from the spirit of the present invention. For example, the present invention is equally applicable to gummy dosage forms where the active ingredient is selected from a group comprising of anti-inflammatory actives, coronary dilators, cerebral dilators, peripheral vasodilators, anti-infectives, psychotropics, anti-manics, stimulants, gastro-intestinal sedatives, antidiarrheal active ingredients, anti-anginal drugs, vasodilators, anti-hypertensive drugs, vasoconstrictors and anti-migraine treatment actives, antibiotics, tranquilizers, antipsychotics, antitumor drugs, anticoagulants and antithrombotic drugs, hypnotics, sedatives, anti-emetics, antinauseants, anticonvulsants, neuromuscular drugs, hyper- and hypoglycemic agents, thyroid and antithyroid preparations, diuretics, antispasmodics, uterine relaxants, nutritional additives, anti-obesity drugs, anabolic drugs, erythropoietic drugs, antiasthmatics, expectorants, cough suppressants, mucolytics, anti-hyperuricemia drugs, antidepressants, and the like, or combinations of the foregoing.

In certain embodiments of the present invention, the chewable gel formulation may include drugs used for treatment of Attention Deficit Hyperactivity Disorder (ADHD) selected from a group comprising of methylphenidate, dexmethylphenidate, amphetamine, dextroamphetamine, and lisdexamfetamine dimesylate; including derivatives, salts (and the like), and/or mixtures of the foregoing.

In certain embodiments of the present invention, the chewable gel formulation may include cannabis or hemp-based active/functional ingredients including, but not limited to, tetrahydrocannabinol, cannabidiol, and cannabis extracts, derivatives, salts (and the like), and/or mixtures of the foregoing.

In certain embodiments of the present invention, the chewable gel formulation includes a complexing agent. A complexing agent is a pharmaceutical grade inactive ingredient which forms a complex with a functional/active ingredient.

In certain embodiments of the present invention, the composition of the chewable gel has a complexing agent content ranging from about two-tenths of one percent-by-weight (0.2% w/w) to about twenty percent-by-weight (20% w/w).

In certain embodiments of the present invention, cyclodextrins, such as hydroxypropyl-beta cyclodextrin ("HP.beta.CD"), can be used as complexing agents. Cyclodextrins are crystalline, homogeneous, non-hygroscopic substances built-up from glucopyranose units (oligomers of dextrose or its derivatives) joined by $\alpha$-1,4-linkages. Typical examples include alpha-, beta-, and/or gamma-cyclodextrin; including derivatives and/or mixtures of the foregoing. Cyclodextrins form an active ingredient-cyclodextrin complex (i.e., an inclusion complex), which is an association between the active ingredient and the cyclodextrin and, preferably, takes the form of a clathrate-type inclusion complex, wherein the functional/active ingredient acts as the guest molecule in the enclosed tubular space of the cyclodextrin host, which facilitates increased solubility of functional/active ingredient. It is theorized that this enwrapping of functional/active ingredient (guest) inside cyclodextrin host may prevent interaction of functional/active ingredient with taste buds and/or interact with the gate-keeper proteins of taste buds affecting their functionality resulting in taste masking an unpleasant functional/active ingredient.

In certain embodiments of the present invention, it is preferable to maintain a ratio of complexing agent to active ingredient whereby the active ingredient(s) remains substantially complexed with complexing agent (i.e., inclusion complex) to maintain high amounts of water insoluble active ingredient in solubilized form, which tends to minimize any disagreeable tastes, such as bitterness, and/or other unpleasant oral sensations, such as numbness of the mouth and tongue, and/or throat irritation that may be associated with the water insoluble (or poorly water soluble) active ingredient. Furthermore, maintaining a ratio of complexing agent to active ingredient whereby active ingredient remains substantially complexed with complexing agent (i.e., inclusion complex) facilitates the formation of a gummy dosage form with superior translucency and enhanced taste. For example, translucent gummy dosage forms that include acetaminophen can be difficult to formulate because acetaminophen has a strong bitter taste and is substantially insoluble in water, which is often a preferred solvent to make gummy dosage forms. When manufacturing such translucent gummy dosage form, it can be imperative to keep all components of the dosage form solubilized, or substantially solubilized, in water. Formation of an inclusion complex of acetaminophen and HP.beta.CD in the proper ratio helps to maintain acetaminophen in, or substantially in, solution, which also helps minimize the bitter taste of acetaminophen. In certain embodiments of the present invention, a ratio of complexing agent to active ingredient of at least about one-to-one (1:1) is preferred.

Complexing agents can also facilitate minimization of disagreeable tastes, such as bitterness, and/or other unpleasant oral sensations with water soluble drugs. For example, diphenhydramine hydrochloride, an active ingredient, is known to cause numbness and/or tingling sensations in the mouth when taken via oral route. The inventors hereof found that when gummy dosage forms of the present invention were formulated using, among other ingredients, diphenhydramine hydrochloride complexed with HP.beta.CD in a ratio of complexing agent to active ingredient of about two-to-one (2:1), no numbness or tingling sensation of mouth was perceived upon mastication of the gummy dosage form.

It should be understood that other complexing agents may be used without departing from the spirit of the present invention. Furthermore, as will be understood by those having ordinary skill in the art, certain aspects of the present invention may apply to the use of complexing agents that form different kinds of complexes with functional/active ingredients. Additionally, it should be understood that certain aspects of the present invention are not limited to formulations that include a complexing agent.

In certain embodiments of the present invention, the chewable gel formulation includes a buffering agent. A buffering agent is a weak acid or base used to maintain the pH of a dispersion near a desired value during the manufacturing process, which, in the context of the present invention, can help minimize molding times (i.e., the amount of time necessary to form a product from a gummy mixture and to remove the formed product from the mold) to less that one (1) hour and/or reduce (or in some instances eliminate) the amount of time needed to cure the gummies after they are removed from a forming device.

In certain embodiments of the present invention, trisodium citrate is used in an amount of up to about one percent-by-weight (1% w/w) to maintain the pH of the gummy mixture in the range of about five (5) to about eight (8). It should be understood that other buffering agents may be used without departing from the spirit of the present invention. Furthermore, it should be understood that certain embodiments of the present invention are not limited to formulations that include a buffering agent.

In certain embodiments of the present invention, the chewable gel formulation includes a non-acidic antimicrobial agent, such as a tonicity modifying agent. As discussed in greater detail below, the use of tonicity modifying agents reduce the need for acidic antimicrobial agents (e.g., citric acid, fumaric acid, benzoic acid, acetic acid, etc.) to inhibit microbial growth.

In certain embodiments of the present invention, the composition of the chewable gel has a tonicity modifying agent content of less than about two percent-by-weight (2% w/w). In certain embodiments of the present invention, sodium chloride is used as a tonicity modifying agent (and may also facilitate improved taste of gummy dosage forms of the present invention).

It should be understood that other antimicrobial agents may be used without departing from the spirit of the present invention. Additionally, it should be understood that certain embodiments of the present invention are not limited to formulations that include a non-acidic antimicrobial agent.

A gelling agent provides structural integrity to the chewable gels of the present invention. More particularly, chewable gels can be described as a two-phase system consisting of suspended particles in a dispersion medium. The suspended particles (i.e., gelling agents) undergo a high degree of cross-linking or association when hydrated, forming an interlaced three-dimensional structure that provides structural integrity to the chewable gel.

In certain embodiments of the present invention, the composition of the chewable gel has a gelling agent content ranging from about one-tenth of one percent-by-weight (0.1% w/w) to about twenty percent-by-weight (20% w/w).

Gelling agents of the present invention may include, but are not limited to, the group comprising of gelatin, alginate, carrageenan, dextran, gellan, guar gum, hyaluronic acid, pullulan, xanthan, xyloglucan, pectins, chitosan, tapioca, and the like; including combinations of the foregoing. It should be understood that other gelling agents may be used without departing from the spirit of the present invention.

Carrageenan is a naturally occurring polysaccharide derived from different species of Rhodophyceae (red seaweed). There are three primary families of carrageenan based on the position of sulfate groups and the presence or absence of anhydrogalactose: lambda, iota, and kappa, with iota-carrageenan being preferred in certain embodiments of the present invention. Carrageenan does not exhibit a thermo-reversible gelling property and is stable in accelerated conditions of temperature (e.g., about thirty-seven degrees Celsius (37° C.) to about forty-three degrees Celsius (43° C.)) and relative humidity (about seventy percent relative humidity (70% RH) to about eighty percent relative humidity (80% RH)) in accordance with guidelines set by the International Council for Harmonisation of Technical Requirements for Pharmaceuticals for Human Use (ICH).

In some embodiments of the present invention, the dosage form contains carrageenan in a concentration of at least one percent-by-weight (1.0% w/w).

Additional information relating to gelling agents can be found in the Handbook of Pharmaceutical Excipients (Raymond C Rowe et al. eds., 6th ed. 2009), which is incorporated herein by reference in its entirety. Additional information concerning carrageenan can be found in the Handbook of Hydrocolloids (Glyn O. Phillips et al., eds., 2nd ed. 2009), which is incorporated herein by reference in its entirety.

In certain embodiments of the present invention, the chewable gel formulation includes a co-solvent. A co-solvent is either a water-miscible or partially miscible organic solvent, that facilitates reduction of strong interactions between water molecules and hence reduces the ability of water to precipitate-out non-polar solute. Co-solvents work synergistically with complexing agents like cyclodextrins to increase the solubility of the functional/active ingredient, which, as discussed above, facilitates the formation of a chewable gel with improved translucency and taste. The exact mechanism of synergism between co-solvent and cyclodextrins is not clear; however, it is assumed that when a co-solvent is introduced into solution containing the inclusion complex, co-solvents facilitate formation of a drug bearing binary/ternary complex increasing solubility of the functional/active ingredient.

In certain embodiments of the present invention, the composition of the chewable gel has a co-solvent content ranging from about one-half of one percent-by-weight (0.5% w/w) to about fifty percent-by-weight (50% w/w).

In certain embodiments of the present invention, the co-solvent is selected from a group comprising of polyethylene glycol ("PEG"), propylene glycol, glycerin/glycerol, sorbitol, maltitol, and the like; including combinations of the foregoing. However, it should be understood that other co-solvents may be used without departing from the spirit of the present invention.

In certain embodiments of the present invention, the chewable gel formulation includes a recrystallization inhibitor. Recrystallization inhibitors aid to inhibit recrystallization of certain ingredients in the composition and can also reduce irritability of the functional/active ingredient on oral mucosa, which aids in masking unpleasant taste of active/functional ingredients and mixtures thereof.

Formulations of the present invention may include one or more recrystallization inhibitors selected from the group consisting of polyvinyl alcohol ("PVA"), mannitol, sodium carboxymethyl cellulose ("CMCNa"), hydroxypropyl methylcellulose ("HPMC"), and povidone (also known as polyvinylpyrrolidone, "PVP"), and the like; including combinations of the foregoing. However, it should be understood that other recrystallization inhibitors may be used without departing from the spirit of the present invention.

In certain embodiments of the present invention, the composition of the chewable gel may have a recrystallization inhibitor content ranging from about one-tenth of one percent-by-weight (0.1% w/w) to about five percent-by-weight (5% w/w).

In certain embodiments of the present invention, the chewable gel formulation includes a non-crystallizing polyol solution. Non-crystallizing polyol solutions provide a sweet taste and will not, under conditions presented herein, precipitate out of solution. Additionally, non-crystallizing polyol solutions may contribute to an increased solubility of the chewable gel formulation; for instance, in formulations containing sugar, non-crystallizing polyol solutions can prevent or reduce recrystallization of solubilized sugar from the gummy composition. If solubilized sugar recrystallizes from the gummy composition, the chewable gels formed therefrom may not have the translucent appearance that is preferred in many embodiments of the present invention.

Formulations of the present invention may also include one or more non-crystallizing polyol solutions selected from the group consisting of non-crystallizing sorbitol solution, maltitol solution, and the like; including combinations of the foregoing. Other non-crystallizing polyol solutions may be used without departing from the spirit of the present invention.

In certain embodiments of the present invention, the chewable gel formulation includes lubricating agents (also referred to as release agents). Lubricating agents facilitate formation of the chewable gel by preventing the occurrence of damaging contact between the gummy and surfaces of dosage form forming devices. In certain embodiments of the present invention, the chewable gel formulation may have a lubricant content ranging from about one-tenth of one percent-by-weight (0.1% w/w) to about five percent-by-weight (5% w/w).

Formulations of the present invention may include at least one lubricating agent selected from the group consisting of mineral oil, light mineral oil, and the like; including combinations of the foregoing. Both mineral oil and light mineral oil are transparent, colorless, viscous oily liquids, without fluorescence in daylight. They are practically tasteless and odorless when cold, and have a faint odor when heated. It should be understood that other lubricating agents may be used without departing from the spirit of the present invention. Furthermore, it should be understood that certain embodiments of the present invention are not limited to formulations that include a lubricating agent.

Formulations of the present invention may also include one or more flavor compositions, for example, fruit flavor compositions, botanical flavor compositions, or mixtures thereof. The particular amount of the flavor component useful for imparting flavor characteristics to the composition of the present invention will depend upon the flavor(s) selected, the flavor impression desired, and the form of the flavor component. Those skilled in the art are readily able to determine the amount of any flavor component(s) used to achieve the desired flavor impression. It should be understood that a wide range of flavor compositions may be used without departing from the spirit of the present invention. Furthermore, it should be understood that certain embodiments of the present invention are not limited to formulations that include a flavor composition.

In certain embodiments of the present invention, the chewable gel formulation may include taste enhancing agents. Taste enhancing agents are substances that may enhance or suppress perceived tastes and/or smells. Also, taste enhancing agents may provide a perceived flavor.

In certain embodiments of the present invention, taste enhancing agents may include taste masking powders, bitter blocker powders, and/or sweetening agents such as dextrose, neotame, and sucralose. It should be understood that other taste enhancing agents may be used without departing from the spirit of the present invention.

In certain embodiments of the present invention, the composition of the chewable gel includes coloring agents such as dyes and pigments. It should be understood that a wide range of coloring agents may be used without departing from the spirit of the present invention. Furthermore, it should be understood that certain embodiments of the present invention are not limited to formulations that include a coloring agent.

In some embodiments of the present invention, a single excipient has more than one function in the gummy formulation. In certain embodiments of the present invention glycerol may serve a multi-purpose role as a co-solvent and a humectant. In certain embodiments of the present invention, maltitol solution may serve a multi-purpose role as a co-solvent and re-crystallization inhibitor. In certain embodiments of the present invention, caster sugar may serve a multi-purpose role as a sweetener and humectant.

In certain embodiments of the present invention, it may be preferable to maintain a product temperature below about one hundred five degrees Celsius (105° C.). Product temperature generally refers to actual temperature at which product is maintained during different stages of manufacturing. Processing temperature refers to a temperature that enables the product temperature to be maintained during various stages of manufacturing. Known processes of manufacturing gummy dosage forms and/or gummy products require higher product temperatures, which can be problematic and/or impractical for the manufacture of pharmaceutical grade gummy dosage forms. For instance, satisfaction of regulatory requirements for pharmaceuticals including, but not limited to, efficacy and safety, is problematic using known processes because of, among other things, difficulties relating to controlling the assay of active ingredient; providing a unit dosage form having acceptable content uniformity and achieving acceptable drug degradation limits. Additionally, known processes of manufacturing gummy dosage forms do not enable addition of the active/functional ingredient near the end of the heating process based on the viscosity and dynamic solid content (% w/w) of the heated gummy mixture, which may result in a unit dosage form having unacceptable content uniformity. Furthermore, known processes of manufacturing gummy dosage forms and/or gummy products at higher product temperatures often require that the higher product temperature of the final gummy mixture be maintained, or substantially maintained, until the final gummy mixture is transferred to a mold or other forming device. Moreover, such known processes often require substantial conditioning at considerably lower temperatures for formation of and/or curing of the final dosage form (i.e., final formed structure), which adds to the duration of processing time (negatively impacting commercial viability). The foregoing limitations of known processes can be overcome by, among other things, maintaining a constant solid content (% w/w) of the gummy mixture during manufacture by proper control of product temperature below about one hundred five degrees Celsius (105° C.) during certain/specific stages of manufacturing.

In certain embodiments of the present invention, it may be preferable to maintain the pH of the gummy mixture in the range of about five (5) to about eight (8). Preferably, the pH of the gummy mixture according to the present invention is maintained in the range of about five (5) to about eight (8) without the use of acid preservatives (e.g., citric acid, fumaric acid, benzoic acid, acetic acid, etc.). Gummies formed by known processes typically have a high-water content (e.g., twenty (20) to thirty-five (35) percent-by-weight), which often requires the addition of acid preservatives to the gummy mixture to prevent microbial spoilage. Characteristically, acid preservatives do not kill microorganisms but inhibit their growth by extending lag phases. Generally, acid preservatives are more effective at low pH values (where solutions contain increased concentrations of undissociated acids), where they become increasingly potent as antimicrobial agents. In gummy formulations that include carrageenan, the use of acid preservatives may be problematic to due to autohydrolysis of carrageenan in gummy mixtures having lower pH levels (and higher temperatures), which can result in, among other things: an increased molding time; and/or a prolonged curing period. In certain embodiments of the present invention, use of a buffering agent (e.g., trisodium citrate) can facilitate a pH of the gummy mixture in a range of about five (5) to about eight (8), which can lead to faster molding times (i.e., less than one (1) hour).

In certain embodiments of the present invention, non-acidic antimicrobial agents, such as tonicity modifying agents, can be used to control microbial content. For instance, sodium chloride can be used to provide a chewable gel composition with a relatively high osmotic pressure gradient (hypertonic), which inhibits microbial growth. This inhibition of microbial growth can be corroborated by the low water activity ($a_w$) of the product. Water activity ($a_w$) of a product is the ratio between the vapor pressure of the product itself, when in a completely undisturbed balance with the surrounding air media, and the vapor pressure of distilled water under identical conditions. Water activity ($a_w$) has its most useful application in predicting the growth of bacteria, yeast, and mold. It is well known that for an orally consumable product to have a useful shelf life without relying on refrigerated storage, it is necessary to control either its acidity level (pH) or the level of water activity ($a_w$) or a suitable combination of the two. This can effectively increase the product's stability and make it possible to predict its shelf life under known ambient storage conditions. In certain embodiments of the present invention, the average water content in the chewable gel unit is about eighteen percent (18%) to about twenty-two percent (22%), with a water activity ($a_w$) of up to 0.75, which provides, among other things, a chewable gel unit having a longer shelf life than what is known in the art.

Solid content is the percentage of solid/dry matter in the formulation. Solid content (SC) can be computed using the following equation: SC=100−((((mass of the wet sample)−(mass of the dry sample))÷(mass of the wet sample))×100). For example, if the mass of the dry sample is thirty grams (30 g) and the mass of the wet sample is forty-five grams (45 g), then the solid content would be approximately sixty-six and seven-tenths percent-by-weight (66.7% w/w). Solid content can be measured using various instruments, including refractometer meters. A refractometer is an optical instrument that employs the measurement of refractive index of a composition to determine the solid content of the composition. In certain embodiments of the present invention, it is preferable for the gummy mixture to have a solid content ranging from about seventy percent-by-weight (70% w/w) to about eighty percent-by-weight (80% w/w); and more preferably ranging from about seventy-four percent-by-weight (74% w/w) to about eighty percent-by-weight (80% w/w). If the solid content is too high or too low, then the gummy dosage forms (gummies) formed may be too sticky or too brittle, respectively. Gummy dosage forms that are too sticky or too brittle will not have the preferred organoleptic properties of the present invention. Further, gummy dosage forms that are too sticky can be difficult to remove from molds (e.g., sticking to the mold), and dosage forms that are too brittle tend to be easily breakable.

As discussed above, the present invention is not limited to any particular dosage form forming device. Many different devices and methods may be used to facilitate shaping the gummy dosage forms without departing from the spirit of the present invention.

The present invention is not limited to any particular means of transferring the gummy mixture to the dosage form forming device(s). With reference to certain manufacturing processes of the present invention, in some embodiments, the gummy mixture may be transferred to the dosage form forming device(s) by pouring or other means of transfer whereby gravity is the primary motive force inducing flow.

With reference to certain manufacturing processes of the present invention, in some embodiments, it is preferable to mechanically induce flow of the gummy mixture to facilitate transfer of the mixture to the dosage form forming device(s). For example, a wide range of pumping devices may be used to facilitate transfer of the gummy mixture to the dosage form forming device or other means of transfer whereby gravity is the primary motive force inducing flow are not sufficient. It should be understood by those having ordinary skill in the art that transferring the gummy mixture to the dosage form forming device(s) may be accomplished by many different ways, including the use of many different types of devices, without departing from the spirit of the present invention. Additionally, it should be understood that gummy dosage forms of the present invention may be made using a continuous process including, but not limited to, mogul-type production systems.

With reference to certain manufacturing processes of the present invention, in some embodiments, the gummy mixture is removed from the dosage form forming device after drying. Drying the gummy mixture may be accomplished in several different ways without departing from the spirit of the present invention. For example, in certain embodiments of the present invention, the gummy mixture is allowed to dry in the dosage form forming device at ambient temperature (also referred to as room temperature, around 20° C.) for a duration of time ranging from about twenty (20) to about thirty (30) minutes (dry time) before the chewable gels are removed. The dry time may be reduced by adjusting a dry time parameter. For example, in certain embodiments of the present invention, the gummy mixture is dried at a temperature ranging from about two degrees Celsius (2° C.) to about five degrees Celsius (5° C.) for a duration of time ranging from about ten (10) minutes to about fifteen (15) minutes before the chewable gels are removed. Different/additional drying parameters (e.g., temperature, etc.) may be used without departing from the spirit of the present invention. As will be discussed in greater detail below, in certain embodiments of the present invention, the chewable gels are cured after being removed from the dosage form forming device. In certain embodiments of the present invention, the chewable gels are cured within the dosage form forming device.

The means of removing the dosage forms from the dosage form forming device may vary depending on the type of dosage form forming device being used. It should be understood by those having ordinary skill in the art that many different types of dosage form forming devices may be used without departing from the spirit of the present invention.

Preferably, once the gummy mixture has sufficiently dried in the dosage form forming device, the individual chewable gels of the present invention are removed. Undesired defects to the appearance and/or shape of the individual chewable gel units of the present invention may occur if improperly removed. Those having ordinary skill in the art will appreciate that such defects can increase manufacturing costs.

In certain embodiments of the present invention, the chewable gel units may optionally include a dusting of polishing agents on the outer surface. When packaged in bulk in certain containers, polishing agents help reduce the occurrence of sticking between one or more chewable gel units. Suitable polishing agents include pregelatinized starch, citric acid anhydrous, magnesium stearate, and combinations of thereof. It should be understood that other polishing agents and/or polishing agent blends may be used without departing from the spirit of the present invention. Furthermore, it should be understood that the present invention is not limited to chewable gel units having a dusting of polishing agents on an outer surface.

With reference to certain manufacturing processes of the present invention, in some embodiments, the chewable gels are cured after removal from the dosage form forming device. Curing period parameters (e.g., duration, temperature, etc.) are important for producing a chewable gel unit that is physically stable. For example, a curing period that is too long may result in dosage forms that are too hard. Conversely, if the curing period is too short, the resulting dosage forms may be sticky, misshapen, and/or easily deformed. In certain embodiments of the present invention, the chewable gels are cured at room temperature for a duration of about forty-eight hours (cure period). Curing methods having different/additional parameters (e.g., temperature, etc.) may be used without departing from the spirit of the present invention. As discussed above, in certain embodiments of the present invention, the chewable gels may be cured without first being removed from the dosage form forming device.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

The compositions and methods of the appended claims are not limited in scope by the specific compositions, formulations, and methods described herein, which are intended as illustrations of a few aspects of the claims. Any compositions, formulations, and methods that are functionally equivalent are intended to fall within the scope of the claims. Various modifications of the compositions, formulations, and methods in addition to those shown and described herein are intended to fall within the scope of the appended claims. Further, while only certain representative compositions, formulations, and method steps disclosed herein are specifically described, other combinations of the compositions, formulations, and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Any publications cited herein and the materials for which they are cited are specifically incorporated by reference.

EXAMPLES the following Examples set forth preferred therapeutic agents and methods in accordance with the invention, but it is to be understood that these examples are given by way of illustration only, and nothing therein should be taken as a limitation upon the overall scope of the invention.

Example 1

A process for making chewable gel units in accordance with certain aspects of the present invention is provided in Example 1 below. The ingredients corresponding to Example 1 are tabulated in Table 1 with the amount of each ingredient used in the process (i.e., the batch quantity) given in kilograms. Each chewable gel unit formed by the process of Example 1 has a mass of about two thousand four hundred fifty milligrams (2,450 mg). Thirty thousand (30,000) chewable gel units are formed by the process of Example 1; however, as should be understood by those having ordinary skill in the art, the principles of Example 1 can be used to make more or less chewable gel units by proportionally increasing or decreasing the amount of ingredients as necessary to produce the desired quantity of chewable gel units.

TABLE 1

| Ingredient Name | Batch Quantity |
| --- | --- |
| Bitter blocker powder | 0.270 |
| Carrageenan | 1.868 |
| Corn syrup (liquid glucose) | 30.375 |
| Flavor agent (tutti frutti flavor) | 0.075 |
| HP.beta.CD | 1.448 |
| Maltitol solution | 6.300 |
| Neotame | 0.038 |
| Purified water | 26.250 |
| Sodium chloride | 0.375 |
| Sucralose | 0.375 |
| Sucrose | 18.263 |
| Trisodium citrate | 0.300 |
| Citric acid anhydrous | 0.300 |
| Pregelatinized starch (starch 1500) | 1.350 |

Procedure—Example 1

Step 1: Add about 82.5% of the batch quantity of purified water to a container. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring, continue stirring while heating the mixture to a temperature in the range of about fifty degrees Celsius (50° C.) to about fifty-five degrees Celsius (55° C.) to form a homogenous mixture.

Step 3: Mix the batch quantities of carrageenan and trisodium citrate, and about 11.0% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about eighty-five degrees Celsius (85° C.) to about ninety-five degrees Celsius (95° C.) until a thick gel mixture is observed.

Step 6: Add the batch quantity of maltitol solution and about 89.0% of the batch quantity of sucrose to the gel mixture of Step 5 while heating the mixture to a temperature in the range of about ninety degrees Celsius (90° C.) to about one hundred ten degrees Celsius (110° C.).

Step 7: Add about 7.6% of the batch quantity of purified water to a container. Slowly add the batch quantity of HP.beta.CD to the purified water under continuous stirring until a clear solution is formed.

Step 8: Combine the solution of Step 7 and the gel mixture of Step 6 under stirring and maintain the temperature of the mixture in the range of about 95° C. to about 110° C. until the total solid content of the mixture raises to about seventy-four percent by weight (74% w/w) or about seventy-four brix (74 brix).

Step 9: Add about 9.9% of the batch quantity of purified water in a container and add the batch quantity of the flavor agent under stirring until a clear solution is formed.

Step 10: Combine the solution of Step 9 to the gel mixture of Step 8 under stirring, maintaining a temperature in the range of about 90° C. to about one hundred five degrees Celsius (105° C.), until a gummy mixture is formed.

Step 11: Prepare a dry mix blend by delumping the batch quantities of pregelatinized starch and citric acid anhydrous using a #40 mesh and mix with a V-blender for approximately about five (5) minutes to form a homogenous blend.

Step 12: Set-up a gummy depositing line with a hopper and a dosator. Set the hopper, distribution plate, and bottom plate to a temperature in the range of about 85° C. to about one hundred fifteen degrees Celsius (115° C.). Set the cooling chamber to a temperature below fifteen degrees Celsius (15° C.).

Step 13: Lubricate gummy molds and conveyer belts with mineral oil (further lubricate during process as necessary to reduce sticking). Feed the hopper of a surface coating machine with the polishing blend of Step 11. Transfer the gummy mixture of Step 10 to the hopper of the gummy depositing line and start the molding process. After the molds are filled with the gummy mixture of Step 10, the molds are transferred to the cooling chamber. After cooling, the individual chewable gel units are ejected from the molds onto a conveyor. The individual chewable gel units are conveyed to the surface coating machine where the polishing blend of Step 11 is sprinkled onto the chewable gel units. The excess polishing blend is collected at the bottom of the surface coating machine.

Step 14: Collect the chewable gel units of Step 13 on curing trays and store for curing at a temperature in the range of about twenty-five degrees Celsius (25° C.) to about thirty-five degrees Celsius (35° C.) for five (5) to seven (7) days.

Step 15: Transfer the chewable gel units of Step 14 into suitable packaging.

Example 2

A process for making chewable gel units in accordance with certain aspects of the present invention is provided in Example 2 below. The ingredients corresponding to Example 2 are tabulated in Table 2 with the amount of each ingredient used in the process (i.e., the batch quantity) given in grams. In Example 2 the active ingredient is cetirizine HCl. Each chewable gel unit formed in accordance with Example 2 has an active strength of cetirizine HCl of about ten milligrams (10 mg). Each chewable gel unit formed by the process of Example 2 has a mass of about two thousand five hundred fifty milligrams (2,550 mg). Two hundred (200) chewable gel units are formed by the process of Example 2; however, as should be understood by those having ordinary skill in the art, the principles of Example 2 can be used to make more or less chewable gel units by proportionally increasing or decreasing the amount of ingredients as necessary to produce the desired quantity of chewable gel units.

TABLE 2

| Ingredient Name | Batch Quantity |
| --- | --- |
| Cetirizine HCl | 1.992 |
| Bitter blocker powder | 1.800 |
| Carrageenan | 12.450 |
| Citric acid anhydrous | 1.000 |
| Corn syrup (liquid glucose) | 207.400 |
| Flavor agent (tutti frutti flavor) | 0.250 |
| HP.beta.CD | 9.650 |
| Maltitol solution | 42.000 |
| Neotame | 0.250 |
| Pregelatinized starch (starch 1500) | 9.000 |
| Purified water | 175.000 |
| Sodium chloride | 2.500 |
| Sucralose | 2.508 |
| Sucrose | 142.200 |
| Trisodium citrate | 2.000 |

Procedure—Example 2

Step 1: Add about 79.2% of the batch quantity of purified water to a container (e.g., manufacturing vessel). Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring, continue stirring while heating the mixture to a temperature in the range of about 50° C. to about 55° C. to form a homogenous mixture.

Step 3: Mix the batch quantities of carrageenan and trisodium citrate, and about 28.1% of the batch quantity of sucrose until a homogenous blend is formed.

Step 4: Add the mixture of Step 3 to the mixture of Step 2 under continuous stirring, maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 71.9% of the batch quantity of sucrose to the gel mixture of Step 5 while maintaining a temperature in the range of about 90° C. to about 105° C.

Step 7: Add about 13% of the batch quantity of purified water to a container. Slowly add the batch quantity of HP.beta.CD to the purified water under continuous stirring until a clear solution is formed.

Step 8: Add the batch quantity of cetirizine HCl to the solution of Step 7 under continuous stirring until a clear solution is formed.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 7.8% of the batch quantity of purified water to a container and add the batch quantity of the flavor agent under stirring until a clear solution is formed.

Step 11: Combine the solution of Step 10 to the gel mixture of Step 9 under stirring, maintaining a temperature in the range of about 90° C. to about 105° C., until a gummy mixture is formed.

Step 12: Transfer the gummy mixture of Step 11 to a product mold. Allow the gummy mixture to cool at room temperature for about ten (10) to about fifteen (15) minutes and then remove the individual chewable gel units from the mold.

Step 13: Mix the batch quantities of pregelatinized starch and citric acid anhydrous until a homogenous blend is formed.

Step 14: Polish the chewable gel units of Step 12 with the blend of Step 13 for approximately 5 to about 10 minutes to form polished chewable gel units.

Step 15: Store the polished chewable gel units of Step 14 for curing at a temperature in the range of about 25° C. to about 35° C. for 5 to 7 days.

Step 16: Transfer the chewable gel units of Step 15 into suitable packaging.

Example 3

A process for making chewable gel units in accordance with certain aspects of the present invention is provided in Example 3 below. The ingredients corresponding to Example 3 are tabulated in Table 3 with the amount of each ingredient used in the process (i.e., the batch quantity) given in grams. In Example 3 the active ingredient is cetirizine HCl. Each chewable gel unit formed in accordance with Example 3 has an active strength of cetirizine HCl of about 10 mg. Each chewable gel unit formed by the process of Example 3 has a mass of about 3,272 mg. One hundred fifty (150) chewable gel units are formed by the process of Example 3; however, as should be understood by those having ordinary skill in the art, the principles of Example 3 can be used to make more or less chewable gel units by proportionally increasing or decreasing the amount of ingredients as necessary to produce the desired quantity of chewable gel units.

TABLE 3

| Ingredient Name | Batch Quantity |
| --- | --- |
| Cetirizine HCl | 1.500 |
| Bitter blocker powder | 2.273 |
| Carrageenan | 14.700 |
| Citric acid anhydrous | 0.900 |
| Color agent (FD&C red #40) | 0.053 |
| Corn syrup (liquid glucose) | 234.750 |
| Flavor agent (strawberry flavor) | 0.525 |
| HP.beta.CD | 10.500 |
| Magnesium stearate | 0.900 |
| Maltitol solution | 147.000 |
| Pregelatinized starch (starch 1500) | 9.000 |
| Purified water | 183.750 |
| Sodium chloride | 3.600 |
| Sucralose | 2.400 |
| Trisodium citrate | 2.700 |

Procedure—Example 3

Step 1: Add about 65.3% of the batch quantity of purified water to a container (e.g., manufacturing vessel). Slowly add and dissolve the batch quantities of sucralose, bitter blocker powder, and sodium chloride under continuous stirring until a clear solution is formed.

Step 2: Add the batch quantity of corn syrup to the solution of Step 1 under continuous stirring, continue stirring while heating the mixture to a temperature in the range of about 50° C. to about 55° C. to form a homogenous mixture.

Step 3: Mix the batch quantities of carrageenan and trisodium citrate until a homogenous blend is formed.

Step 4: Add the mixture of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution to the gel mixture of Step 5 while maintaining a temperature in the range of about 90° C. to about 105° C.

Step 7: Add about 19.9% of the batch quantity of purified water to a container. Slowly add the batch quantity of HP.beta.CD to the purified water under continuous stirring until a clear solution is formed.

Step 8: Add the batch quantity of cetirizine HCl to the solution of Step 7 under continuous stirring until a clear solution is formed.

Step 9: Combine the solution of Step 8 and the gel mixture of Step 6 under stirring and maintain the temperature of the mixture in the range of about 90° C. to about 105° C. until the total solid content of the mixture raises to about sixty percent by weight (60% w/w) or about sixty brix (60 brix).

Step 10: Add about 14.8% of the batch quantity of purified water to a container and add the batch quantities of the flavor agent and the color agent under stirring until a clear solution is formed.

Step 11: Combine the solution of Step 10 with the gel mixture of Step 9 under stirring, maintaining a temperature in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 4

A process for making chewable gel units in accordance with certain aspects of the present invention is provided in Example 4 below. The ingredients corresponding to Example 4 are tabulated in Table 4 with the amount of each ingredient used in the process (i.e., the batch quantity) given in kilograms. In Example 4 the active ingredient is diphenhydramine HCl. Each chewable gel unit formed in accordance with Example 4 has an active strength of diphenhydramine HCl of about 12.5 mg. Each chewable gel unit formed by the process of Example 4 has a mass of about 2,500 mg. Thirty thousand (30,000) chewable gel units are formed by the process of Example 4; however, as should be understood by those having ordinary skill in the art, the principles of Example 4 can be used to make more or less chewable gel units by proportionally increasing or decreasing the amount of ingredients as necessary to produce the desired quantity of chewable gel units.

TABLE 4

| Ingredient Name | Batch Quantity |
| --- | --- |
| Diphenhydramine HCl | 0.375 |
| Bitter blocker powder | 0.270 |
| Carrageenan | 1.875 |
| Citric acid anhydrous | 0.150 |
| Corn syrup (liquid glucose) | 30.375 |
| Flavor agent (tutti frutti flavor) | 0.075 |
| HP.beta.CD | 1.448 |
| Maltitol solution | 6.300 |
| Neotame | 0.038 |
| Pregelatinized starch (starch 1500) | 1.350 |
| Purified water | 26.250 |
| Sodium chloride | 0.375 |
| Sucralose | 0.375 |
| Sucrose | 18.195 |
| Trisodium citrate | 0.300 |

Procedure—Example 4

Step 1: Add about 82.5% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring, continue stirring while heating the mixture to a temperature in the range of about 50° C. to about 55° C. to form a homogenous mixture.

Step 3: Mix the batch quantities of carrageenan and trisodium citrate, and about 11.0% of the batch quantity of sucrose until a homogenous blend is formed.

Step 4: Add the mixture of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 89.0% of the batch quantity of sucrose to the gel mixture of Step 5, maintaining a temperature in the range of about 90° C. to about 105° C.

Step 7: Add about 7.6% of the batch quantity of purified water to a container. Slowly add the batch quantity of HP.beta.CD to the purified water under continuous stirring until a clear solution is formed.

Step 8: Add the batch quantity of diphenhydramine HCl to the solution of Step 7 under continuous stirring until a clear solution is formed.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 9.9% of the batch quantity of purified water in a container and add the batch quantity of the flavor agent under stirring until a clear solution is formed.

Step 11: Combine the solution of Step 10 and the gel mixture of Step 9 under stirring, maintaining a temperature in the range of about 90° C. to about 105° C. until a gummy mixture is formed.

Step 12: Prepare a dry mix blend by delumping the batch quantities of pregelatinized starch and citric acid anhydrous using a #40 mesh and mix with a V-blender for approximately about five (5) minutes to form a homogenous blend.

Step 13: Set-up a gummy depositing line with a hopper and a dosator. Set the hopper, distribution plate, and bottom plate to a temperature in the range of about 85° C. to about 115° C. Set the cooling chamber to a temperature below 15° C.

Step 14: Lubricate gummy molds and conveyer belts with mineral oil (further lubricate during the process as necessary to reduce sticking). Feed the hopper of a surface coating machine with the polishing blend of Step 12. Transfer the gummy mixture of Step 11 to the hopper of the gummy depositing line and start the molding process. After the molds are filled with the gummy mixture of Step 11, the molds are transferred to the cooling chamber. After cooling, the individual chewable gel units are ejected from the molds onto a conveyor. The individual chewable gel units are conveyed to the surface coating machine where the polishing blend of Step 12 is sprinkled onto the chewable gel units. The excess polishing blend is collected at the bottom of the surface coating machine.

Step 15: Collect the chewable gel units of Step 14 on curing trays and store for curing at a temperature in the range of about 25° C. to about 35° C. for 5 to 7 days.

Step 16: Transfer the chewable gel units of Step 15 into suitable packaging.

Example 5

A process for making chewable gel units in accordance with certain aspects of the present invention is provided in Example 5 below. The ingredients corresponding to Example 5 are tabulated in Table 5 with the amount of each ingredient used in the process (i.e., the batch quantity) given in kilograms. In Example 5 the active ingredient is diphenhydramine HCl. Each chewable gel unit formed in accordance with Example 5 has an active strength of diphenhydramine HCl of about 12.5 mg. Each chewable gel unit formed by the process of Example 5 has a mass of about 2,455 mg. Thirty thousand (30,000) chewable gel units are formed by the process of Example 5; however, as should be understood by those having ordinary skill in the art, the principles of Example 5 can be used to make more or less chewable gel units by proportionally increasing or decreasing the amount of ingredients as necessary to produce the desired quantity of chewable gel units.

TABLE 5

| Ingredient Name | Batch Quantity |
| --- | --- |
| Diphenhydramine HCl | 0.375 |
| Bitter blocker powder | 0.270 |
| Carrageenan | 1.875 |
| Citric acid anhydrous | 0.150 |
| Corn syrup (liquid glucose) | 30.375 |
| Flavor agent (tutti frutti flavor) | 0.075 |
| HP.beta.CD | 1.448 |
| Magnesium stearate | 0.150 |
| Maltitol solution | 6.300 |
| Neotame | 0.038 |
| Pregelatinized starch (starch 1500) | 1.350 |
| Purified water | 26.250 |
| Sodium chloride | 0.375 |
| Sucralose | 0.375 |
| Sucrose | 18.195 |
| Trisodium citrate | 0.300 |

Procedure—Example 5

Step 1: Add about 82.5% of the batch quantity of purified water to a container (e.g., manufacturing vessel). Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. to form a homogenous mixture.

Step 3: Mix the batch quantities of carrageenan and trisodium citrate, and about 11.0% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 89.0% of the batch quantity of sucrose to the gel mixture of Step 5, maintaining a temperature in the range of about 90° C. to about 105° C.

Step 7: Add about 7.6% of the batch quantity of purified water to a container. Slowly add the batch quantity of HP.beta.CD to the purified water under continuous stirring until a clear solution is formed.

Step 8: Add the batch quantity of diphenhydramine HCl to the solution of Step 7 under continuous stirring for approximately about twenty (20) minutes or until a clear solution is observed.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 9.9% of the batch quantity of purified water in a container and add the batch quantity of the flavor agent under stirring until a clear solution is formed.

Step 11: Combine the solution of Step 10 and the gel mixture of Step 9 under stirring, maintaining a temperature in the range of about 90° C. to about 105° C. until a gummy mixture is formed.

Step 12: Prepare a dry mix blend by delumping the batch quantities of pregelatinized starch, citric acid anhydrous, and magnesium stearate using a #40 mesh and mix with a V-blender for approximately about five (5) minutes to form a homogenous blend.

Step 13: Set-up a gummy depositing line with a hopper and a dosator. Set the hopper, distribution plate, and bottom plate to a temperature in the range of about 85° C. to about 115° C. Set the cooling chamber to a temperature below 15° C.

Step 14: Lubricate gummy molds and conveyer belts with mineral oil (further lubricate during the process as necessary to reduce sticking). Feed the hopper of a surface coating machine with the polishing blend of Step 12. Transfer the gummy mixture of Step 11 to the hopper of the gummy depositing line and start the molding process. After the molds are filled with the gummy mixture of Step 11, the molds are transferred to the cooling chamber. After cooling, the individual chewable gel units are ejected from the molds onto a conveyor. The individual chewable gel units are conveyed to the surface coating machine where the polishing blend of Step 12 is sprinkled onto the chewable gel units. The excess polishing blend is collected at the bottom of the surface coating machine.

Step 15: Collect the chewable gel units of Step 14 on curing trays and store for curing at a temperature in the range of about 25° C. to about 35° C. for 5 to 7 days.

Step 16: Transfer the chewable gel units of Step 15 into suitable packaging.

Example 6

A process for making chewable gel units in accordance with certain aspects of the present invention is provided in Example 6 below. The ingredients corresponding to Example 6 are tabulated in Table 6 with the amount of each ingredient used in the process (i.e., the batch quantity) given in grams. In Example 6 the active ingredient is diphenhydramine HCl. Each chewable gel unit formed in accordance with Example 6 has an active strength of diphenhydramine HCl of about 25 mg. Each chewable gel unit formed by the process of Example 6 has a mass of about 4,088 mg. Two hundred fifty (250) chewable gel units are formed by the process of Example 6; however, as should be understood by those having ordinary skill in the art, the principles of Example 6 can be used to make more or less chewable gel units by proportionally increasing or decreasing the amount of ingredients as necessary to produce the desired quantity of chewable gel units.

TABLE 6

| Ingredient Name | Batch Quantity |
| --- | --- |
| Diphenhydramine HCl | 6.250 |
| Bitter blocker powder | 4.250 |
| Carrageenan | 25.000 |
| Citric acid anhydrous | 2.000 |
| Corn syrup (liquid glucose) | 400.000 |
| Flavor agent (tutti frutti flavor) | 0.750 |
| HP.beta.CD | 25.000 |
| Magnesium stearate | 2.000 |
| Maltitol solution | 82.500 |
| Neotame | 0.250 |
| Pregelatinized starch (starch 1500) | 18.000 |
| Purified water | 350.000 |
| Sodium chloride | 3.250 |
| Sucralose | 3.750 |
| Sucrose | 245.000 |
| Trisodium citrate | 4.000 |

Procedure—Example 6

Step 1: Add about 68.6% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. until a homogenous mixture is formed.

Step 3: Mix the batch quantities of carrageenan and trisodium citrate, and about 32.7% of the batch quantity of sucrose until a homogenous blend is formed.

Step 4: Add the blend formed in Step 3 to the mixture of Step 2 under continuous stirring while maintaining the temperature of the mixture in the range of about 50° C. to about 55° C. until a homogenous gel is formed.

Step 5: Heat the gel formed in Step 4 to a temperature in the range of about 90° C. to about 105° C. until a thick gel mixture is formed.

Step 6: Add the batch quantity of maltitol solution and about 67.3% of the batch quantity of sucrose to the gel mixture formed in Step 5, maintaining the temperature of the mixture in the range of about 90° C. to about 105° C.

Step 7: Add about 22.9% of the batch quantity of purified water to a container. Slowly add the batch quantity of HP.beta.CD to the purified water under continuous stirring until a clear solution is formed.

Step 8: Add the batch quantity of diphenhydramine HCl to the solution of Step 7 under continuous stirring until a clear solution is formed.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 8.5% of the batch quantity of purified water in a container and add the batch quantity of the flavor agent under stirring until a clear solution is formed.

Step 11: Add the solution formed in Step 10 to the gel mixture of Step 9 under stirring while maintaining a temperature of the mixture in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units formed in Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 7

A process for making chewable gel units in accordance with certain aspects of the present invention is provided in Example 7 below. The ingredients corresponding to Example 7 are tabulated in Table 7 with the amount of each ingredient used in the process (i.e., the batch quantity) given in grams. In Example 7 the active ingredient is loratadine. Each chewable gel unit formed in accordance with Example 7 has an active strength of loratadine of about 10 mg. Each chewable gel unit formed by the process of Example 7 has a mass of about 2,550 mg. One thousand (1,000) chewable gel units are formed by the process of Example 7; however, as should be understood by those having ordinary skill in the art, the principles of Example 7 can be used to make more or less chewable gel units by proportionally increasing or decreasing the amount of ingredients as necessary to produce the desired quantity of chewable gel units.

TABLE 7

| Ingredient Name | Batch Quantity |
| --- | --- |
| Loratadine | 10.000 |
| Bitter blocker powder | 9.000 |
| Carrageenan | 62.250 |
| Citric acid anhydrous | 5.000 |
| Corn syrup (liquid glucose) | 993.300 |
| Flavor agent (tutti frutti flavor) | 1.250 |
| HP.beta.CD | 100.000 |
| Maltitol solution | 199.650 |
| Neotame | 1.250 |
| Pregelatinized starch (starch 1500) | 45.000 |
| Purified water | 875.000 |
| Sodium chloride | 12.500 |
| Sucralose | 12.500 |
| Sucrose | 588.300 |
| Trisodium citrate | 10.000 |

Procedure—Example 7

Step 1: Add about 52.9% of the batch quantity of purified water to a container (e.g., manufacturing vessel). Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. to form a homogenous mixture.

Step 3: Mix the batch quantities of carrageenan and trisodium citrate, and about 34.0% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. to form a homogenous gel.

Step 5: Heat the gel formed in Step 4 to a temperature in the range of about 90° C. to about 105° C. to form a thick gel mixture.

Step 6: Add the batch quantity of maltitol solution and about 66.0% of the batch quantity of sucrose to the gel mixture formed in Step 5 while maintaining a temperature of the mixture in the range of about 90° C. to about 105° C.

Step 7: Add about 45.7% of the batch quantity of purified water to a container. Slowly add the batch quantity of HP.beta.CD to the purified water under continuous stirring until a clear solution is formed.

Step 8: Add the batch quantity of loratadine to the solution of Step 7 under continuous stirring until a clear solution is formed and heat the solution to a temperature in the range of about seventy degrees Celsius (70° C.) to about eighty degrees Celsius (80° C.).

Step 9: Add the solution of Step 8 to the gel mixture formed in Step 6 under stirring and maintain the temperature of the mixture in the range of about 90° C. to about 105° C. until the total solid content of the mixture raises to about 74% w/w or about 74 brix.

Step 10: Add about 1.4% of the batch quantity of purified water and the batch quantity of the flavor agent to a container under stirring until a clear solution is formed.

Step 11: Combine the solution of Step 10 and the gel mixture formed in Step 9 under stirring while maintaining a temperature in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch and citric acid anhydrous to form a homogenous blend.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 8

A process for making chewable gel units in accordance with certain aspects of the present invention is provided in Example 8 below. The ingredients corresponding to Example 8 are tabulated in Table 8 with the amount of each ingredient used in the process (i.e., the batch quantity) given in grams. In Example 8 the active ingredient is loratadine. Each chewable gel unit formed in accordance with Example 8 has an active strength of loratadine of about 10 mg. Each chewable gel unit formed by the process of Example 8 has a mass of about 3,584 mg. One hundred (100) chewable gel units are formed by the process of Example 8; however, as should be understood by those having ordinary skill in the art, the principles of Example 8 can be used to make more or less chewable gel units by proportionally increasing or decreasing the amount of ingredients as necessary to produce the desired quantity of chewable gel units.

TABLE 8

| Ingredient Name | Batch Quantity |
| --- | --- |
| Loratadine | 1.000 |
| Bitter blocker powder | 1.515 |
| Carrageenan | 10.000 |
| Citric acid anhydrous | 0.700 |
| Color agent (FD&C red #40) | 0.035 |
| Corn syrup (liquid glucose) | 137.500 |
| Flavor agent (orange flavor) | 0.350 |
| HP.beta.CD | 15.000 |
| Magnesium stearate | 0.700 |
| Maltitol solution | 106.000 |
| Pregelatinized starch (starch 1500) | 7.000 |
| Purified water | 125.000 |
| Sucralose | 2.100 |
| Trisodium citrate | 4.000 |

Procedure—Example 8

Step 1: Add about 62.4% of the batch quantity of purified water to a main manufacturing vessel. Slowly add and dissolve the batch quantities of sucralose and bitter blocker powder under continuous stirring until a clear solution is formed.

Step 2: Add the batch quantity of corn syrup to the solution of Step 1 under continuous stirring while heating the mixture to a temperature in the range of about 50° C. to about 55° C. until a homogenous mixture is formed.

Step 3: Mix the batch quantities of carrageenan and trisodium citrate until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel formed in Step 4 to a temperature in the range of about 90° C. to about 105° C. until a thick gel mixture is observed.

Step 6: Add the batch quantity of maltitol solution to the gel mixture of Step 5 while maintaining the temperature of the mixture in the range of about 90° C. to about 105° C.

Step 7: Add about 24.0% of the batch quantity of purified water to a container. Slowly add the batch quantity of HP.beta.CD to the purified water under continuous stirring until a clear solution is formed.

Step 8: Add the batch quantity of loratadine to the solution of Step 7 under continuous stirring until a clear solution is formed and heat to a temperature in the range of about 70° C. to about 80° C.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 13.6% of the batch quantity of purified water and the batch quantities of the flavor agent and the color agent to a container under stirring until a clear solution is formed.

Step 11: Add the solution of Step 10 to the gel mixture formed in Step 9 under stirring while maintaining the temperature of the mixture in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Store the chewable gel units formed in Step 14 for curing at a temperature in the range of about 25° C. to about 35° C. for 5 to 7 days.

Step 16: Transfer the chewable gel units of Step 15 into suitable packaging.

Example 9

A process for making chewable gel units in accordance with certain aspects of the present invention is provided in Example 9 below. The ingredients corresponding to Example 9 are tabulated in Table 9 with the amount of each ingredient used in the process (i.e., the batch quantity) given in grams. In Example 9 the active ingredient is dextromethorphan HBr. Each chewable gel unit formed in accordance with Example 9 has an active strength of dextromethorphan HBr of about 30 mg. Each chewable gel unit formed by the process of Example 9 has a mass of about 3,580 mg. Six hundred (600) chewable gel units are formed by the process of Example 9; however, as should be understood by those having ordinary skill in the art, the principles of Example 9 can be used to make more or less chewable gel units by proportionally increasing or decreasing the amount of ingredients as necessary to produce the desired quantity of chewable gel units.

TABLE 9

| Ingredient Name | Batch Quantity |
| --- | --- |
| Dextromethorphan HBr | 18.972 |
| Bitter blocker powder | 7.500 |
| Carrageenan | 52.800 |
| Citric acid anhydrous | 4.800 |
| Corn syrup (liquid glucose) | 780.000 |
| Flavor agent (tutti frutti flavor) | 1.728 |
| HP.beta.CD | 150.000 |
| Maltitol solution | 168.000 |
| Neotame | 0.600 |
| Pregelatinized starch (starch 1500) | 43.200 |
| Purified water | 720.000 |
| Sodium chloride | 10.800 |
| Sucralose | 9.600 |
| Sucrose | 486.000 |
| Trisodium citrate | 9.000 |

Procedure—Example 9

Step 1: Add about 72.9% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. until a homogenous mixture is formed.

Step 3: Mix the batch quantities of carrageenan and trisodium citrate, and about 34.6% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 65.4% of the batch quantity of sucrose to the gel mixture of Step 5 while maintaining a temperature in the range of about 90° C. to about 105° C.

Step 7: Add about 23.3% of the batch quantity of purified water to a container. Slowly add the batch quantity of HP.beta.CD to the purified water under continuous stirring until a clear solution is formed.

Step 8: Add the batch quantity of dextromethorphan HBr to the solution of Step 7 under continuous stirring until a clear solution is formed.

Step 9: Combine the solution of Step 8 and the gel mixture formed in Step 6 under stirring and maintain the temperature of the mixture in the range of about 90° C. to about 105° C. until the total solid content of the mixture raises to about 74% w/w or about 74 brix.

Step 10: Add about 3.8% of the batch quantity of purified water and the batch quantity of the flavor agent to a container under stirring until a clear solution is formed.

Step 11: Combine the solution of Step 10 and the gel mixture of Step 9 under stirring while maintaining the temperature of the mixture in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch and citric acid anhydrous until a homogenous blend is formed.

Step 14: Polish the chewable gel units of Step 12 with the blend of Step 13 for approximately 5 to about 10 minutes to form polished chewable gel units.

Step 15: Store the chewable gel units formed in Step 14 for curing at a temperature in the range of about 25° C. to about 35° C. for 5 to 7 days.

Step 16: Transfer the chewable gel units of Step 15 into suitable packaging.

Example 10

A process for making chewable gel units in accordance with certain aspects of the present invention is provided in Example 10 below. The ingredients corresponding to Example 10 are tabulated in Table 10 with the amount of each ingredient used in the process (i.e., the batch quantity) given in grams. In Example 10 the active ingredient is dimenhydrinate. Each chewable gel unit formed in accordance with Example 10 has an active strength of dimenhydrinate of about 25 mg. Each chewable gel unit formed by the process of Example 10 has a mass of about 3,588 mg. Two hundred fifty (250) chewable gel units are formed by the process of Example 10; however, as should be understood by those having ordinary skill in the art, the principles of Example 10 can be used to make more or less chewable gel units by proportionally increasing or decreasing the amount of ingredients as necessary to produce the desired quantity of chewable gel units.

TABLE 10

| Ingredient Name | Batch Quantity |
| --- | --- |
| Dimenhydrinate | 6.250 |
| Bitter blocker powder | 3.250 |
| Carrageenan | 21.875 |
| Citric acid anhydrous | 2.000 |
| Corn syrup (liquid glucose) | 350.000 |
| Flavor agent (tutti frutti flavor) | 0.500 |
| HP.beta.CD | 87.500 |
| Magnesium stearate | 2.000 |
| Maltitol solution | 75.000 |
| Neotame | 0.250 |
| Pregelatinized starch (starch 1500) | 18.000 |
| Purified water | 295.000 |
| Sodium chloride | 3.750 |
| Sucralose | 4.375 |
| Sucrose | 155.000 |
| Trisodium citrate | 3.500 |

Procedure—Example 10

Step 1: Add about 59.3% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. to form a homogenous mixture.

Step 3: Mix the batch quantities of carrageenan and trisodium citrate, and about 45.2% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 54.8% of the batch quantity of sucrose to the gel mixture of Step 5 while maintaining the temperature of the mixture in the range of about 90° C. to about 105° C.

Step 7: Add about 32.5% of the batch quantity of purified water to a container. Slowly add the batch quantity of HP.beta.CD to the purified water under continuous stirring until a clear solution is formed.

Step 8: Add the batch quantity of dimenhydrinate to the solution of Step 7 under continuous stirring until a clear solution is formed.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 8.2% of the batch quantity of purified water and the batch quantity of the flavor agent to a container under stirring until a clear solution is formed.

Step 11: Combine the solution of Step 10 and the gel mixture of Step 9 under stirring while maintaining the temperature of the mixture in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 11

A process for making chewable gel units in accordance with certain aspects of the present invention is provided in Example 11 below. The ingredients corresponding to Example 11 are tabulated in Table 11 with the amount of each ingredient used in the process (i.e., the batch quantity) given in grams. In Example 11 the active ingredient is fexofenadine HCl. Each chewable gel unit formed in accordance with Example 11 has an active strength of fexofenadine HCl of about 30 mg. Each chewable gel unit formed by the process of Example 11 has a mass of about 4,088 mg. One hundred fifty (150) chewable gel units are formed by the process of Example 11; however, as should be understood by those having ordinary skill in the art, the principles of Example 11 can be used to make more or less chewable gel units by proportionally increasing or decreasing the amount of ingredients as necessary to produce the desired quantity of chewable gel units.

TABLE 11

| Ingredient Name | Batch Quantity |
| --- | --- |
| Fexofenadine HCl | 4.500 |
| Bitter blocker powder | 2.400 |
| Carrageenan | 16.500 |
| Citric acid anhydrous | 1.200 |
| Corn syrup (liquid glucose) | 228.900 |
| Flavor agent (cool mint flavor) | 0.030 |
| Flavor agent (orange flavor) | 0.300 |
| HP.beta.CD | 60.000 |
| Magnesium stearate | 1.200 |
| Maltitol solution | 60.000 |
| Neotame | 0.150 |
| Pregelatinized starch (starch 1500) | 10.800 |
| Purified water | 199.650 |
| Sodium chloride | 3.300 |
| Sucralose | 3.300 |
| Sucrose | 107.250 |
| Trisodium citrate | 3.720 |

Procedure—Example 11

Step 1: Add about 45.1% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. to form a homogenous mixture.

Step 3: Mix the batch quantities of carrageenan and trisodium citrate, and about 55.9% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 44.1% of the batch quantity of sucrose to the gel mixture of Step 5 while maintaining the temperature of the mixture in the range of about 90° C. to about 105° C.

Step 7: Add about 42.1% of the batch quantity of purified water to a container. Slowly add the batch quantity of HP.beta.CD to the purified water under continuous stirring until a clear solution is formed.

Step 8: Add the batch quantity of fexofenadine HCl to the solution of Step 7 under continuous stirring until a clear solution is formed.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 12.8% of the batch quantity of purified water and the batch quantities of the flavor agents to a container under stirring until a clear solution is formed.

Step 11: Combine the solution of Step 10 and the gel mixture of Step 9 under stirring while maintaining the temperature of the mixture in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 12

A process for making chewable gel units in accordance with certain aspects of the present invention is provided in Example 12 below. The ingredients corresponding to Example 12 are tabulated in Table 12 with the amount of each ingredient used in the process (i.e., the batch quantity) given in grams. In Example 12 the active ingredient is fexofenadine HCl. Each chewable gel unit formed in accordance with Example 12 has an active strength of fexofenadine HCl of about 60 mg. Each chewable gel unit formed by the process of Example 12 has a mass of about 4,088 mg. One hundred fifty (150) chewable gel units are formed by the process of Example 12; however, as should be understood by those having ordinary skill in the art, the principles of Example 12 can be used to make more or less chewable gel units by proportionally increasing or decreasing the amount of ingredients as necessary to produce the desired quantity of chewable gel units.

TABLE 12

| Ingredient Name | Batch Quantity |
| --- | --- |
| Fexofenadine HCl | 9.000 |
| Bitter blocker powder | 2.400 |
| Carrageenan | 16.500 |
| Citric acid anhydrous | 1.200 |
| Corn syrup (liquid glucose) | 225.000 |
| Flavor agent (cool mint flavor) | 0.060 |
| Flavor agent (orange flavor) | 0.600 |
| HP.beta.CD | 60.000 |
| Magnesium stearate | 1.200 |
| Maltitol solution | 60.000 |
| Neotame | 0.150 |
| Pregelatinized starch (starch 1500) | 10.800 |
| Purified water | 199.440 |
| Sodium chloride | 3.300 |
| Sucralose | 3.300 |
| Sucrose | 105.000 |
| Trisodium citrate | 5.250 |

Procedure—Example 12

Step 1: Add about 45.1% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring, continue stirring while heating the mixture to a temperature in the range of about 50° C. to about 55° C. to form a homogenous mixture.

Step 3: Mix the batch quantities of carrageenan and trisodium citrate, and about 57.1% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 42.9% of the batch quantity of sucrose to the gel mixture of Step 5 while maintaining the temperature of the mixture in the range of about 90° C. to about 105° C.

Step 7: Add about 45.1% of the batch quantity of purified water to a container. Slowly add the batch quantity of HP.beta.CD to the purified water under continuous stirring until a clear solution is formed.

Step 8: Add the batch quantity of fexofenadine HCl to the solution of Step 7 under continuous stirring until a clear solution is formed.

Step 9: Combine the solution of Step 8 and the gel mixture formed in Step 6 under stirring and maintain the temperature of the mixture in the range of about 90° C. to about 105° C. until the total solid content of the mixture raises to about 74% w/w or about 74 brix.

Step 10: Add about 9.8% of the batch quantity of purified water and the batch quantities of the flavor agents to a container under stirring until a clear solution is formed.

Step 11: Combine the solution of Step 10 and the gel mixture of Step 9 under stirring, maintaining a temperature in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 13

A process for making chewable gel units in accordance with certain aspects of the present invention is provided in Example 13 below. The ingredients corresponding to Example 13 are tabulated in Table 13 with the amount of each ingredient used in the process (i.e., the batch quantity) given in grams. In Example 13 the active ingredient is acetaminophen. Each chewable gel unit formed in accordance with Example 13 has an active strength of acetaminophen of about 160 mg. Each chewable gel unit formed by the process of Example 13 has a mass of about 3,667 mg. Five hundred (500) chewable gel units are formed by the process of Example 13; however, as should be understood by those having ordinary skill in the art, the principles of Example 13 can be used to make more or less chewable gel units by proportionally increasing or decreasing the amount of ingredients as necessary to produce the desired quantity of chewable gel units.

TABLE 13

| Ingredient Name | Batch Quantity |
| --- | --- |
| Acetaminophen | 80.000 |
| Bitter blocker powder | 6.653 |
| Carrageenan | 46.200 |
| Citric acid anhydrous | 3.500 |
| Color agent (FD&C yellow) | 0.050 |
| Corn syrup (liquid glucose) | 659.644 |
| Flavor agent (cool mint flavor) | 0.087 |
| Flavor agent (orange flavor) | 0.867 |
| HP.beta.CD | 200.000 |
| Maltitol solution | 197.378 |
| Neotame | 0.578 |
| Pregelatinized starch (starch 1500) | 30.000 |
| Purified water | 554.750 |
| Sodium chloride | 9.240 |
| Sucralose | 9.240 |
| Sucrose | 297.925 |
| Trisodium citrate | 7.390 |

Procedure—Example 13

Step 1: Add about 51.9% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. to form a homogenous mixture.

Step 3: Mix the batch quantities of carrageenan and trisodium citrate, and about 36.3% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 63.7% of the batch quantity of sucrose to the gel mixture of Step 5 while maintaining the temperature of the mixture in the range of about 90° C. to about 105° C.

Step 7: Add about 46.0% of the batch quantity of purified water to a container. Slowly add the batch quantity of HP.beta.CD to the purified water under continuous stirring until a clear solution is formed.

Step 8: Add the batch quantity of acetaminophen to the solution of Step 7 under continuous stirring until a clear solution is formed and heat to a temperature in the range of about 70° C. to about 80° C.

Step 9: Combine the solution of Step 8 and the gel mixture of Step 6 under stirring and maintain the temperature of the mixture in the range of about 90° C. to about 105° C. until the total solid content of the mixture raises to about 74% w/w or about 74 brix.

Step 10: Add about 2.1% of the batch quantity of purified water and the batch quantities of the flavor agents and the color agent in a container under stirring until a clear solution is formed.

Step 11: Add the solution of Step 10 to the gel mixture formed in Step 9 under stirring while maintaining the temperature of the mixture in the range of about 90° C. to about 105° C. to form a gummy mixture.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch and citric acid anhydrous until a homogenous blend is formed.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 14

A process for making chewable gel units in accordance with certain aspects of the present invention is provided in Example 14 below. The ingredients corresponding to Example 14 are tabulated in Table 14 with the amount of each ingredient used in the process (i.e., the batch quantity) given in grams. In Example 14 the active ingredient is guaifenesin. Each chewable gel unit formed in accordance with Example 14 has an active strength of guaifenesin of about 100 mg. Each chewable gel unit formed by the process of Example 14 has a mass of about 4,088 mg. Six hundred (600) chewable gel units are formed by the process of Example 14; however, as should be understood by those having ordinary skill in the art, the principles of Example 14 can be used to make more or less chewable gel units by proportionally increasing or decreasing the amount of ingredients as necessary to produce the desired quantity of chewable gel units.

TABLE 14

| Ingredient Name | Batch Quantity |
| --- | --- |
| Guaifenesin | 60.000 |
| Bitter blocker powder | 11.400 |
| Carrageenan | 60.000 |
| Citric acid anhydrous | 4.800 |
| Corn syrup (liquid glucose) | 720.000 |
| Flavor agent (tutti frutti flavor) | 3.000 |
| HP.beta.CD | 210.000 |
| Magnesium stearate | 4.800 |
| Maltitol solution | 240.000 |
| Neotame | 0.600 |
| Pregelatinized starch (starch 1500) | 43.200 |
| Purified water | 840.000 |
| Sodium chloride | 7.200 |
| Sucralose | 12.000 |
| Sucrose | 588.000 |
| Trisodium citrate | 7.800 |

Procedure—Example 14

Step 1: Add about 40.5% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. to form a homogenous mixture.

Step 3: Mix the batch quantities of carrageenan and trisodium citrate, and about 32.7% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 67.3% of the batch quantity of sucrose to the gel mixture of Step 5 while maintaining the temperature of the mixture in the range of about 90° C. to about 105° C.

Step 7: Add about 46.4% of the batch quantity of purified water to a container. Slowly add the batch quantity of HP.beta.CD to the purified water under continuous stirring until a clear solution is formed.

Step 8: Add the batch quantity of guaifenesin to the solution of Step 7 under continuous stirring until a clear solution is formed.

Step 9: Combine the solution of Step 8 and the gel mixture formed in Step 6 under stirring and maintain the temperature of the mixture in the range of about 90° C. to about 105° C. until the total solid content of the mixture raises to about 74% w/w or about 74 brix.

Step 10: Add about 13.1% of the batch quantity of purified water and the batch quantity of the flavor agent to a container under stirring until a clear solution is formed.

Step 11: Combine the solution of Step 10 and the gel mixture of Step 9 under stirring while maintaining the temperature of the mixture in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 15

A process for making chewable gel units in accordance with certain aspects of the present invention is provided in Example 15 below. The ingredients corresponding to Example 15 are tabulated in Table 15 with the amount of each ingredient used in the process (i.e., the batch quantity) given in grams. In Example 15 the active ingredient is phenylephrine HCl. Each chewable gel unit formed in accordance with Example 15 has an active strength of phenylephrine HCl of about 10 mg. Each chewable gel unit formed by the process of Example 15 has a mass of about 2,550 mg. Two hundred (200) chewable gel units are formed by the process of Example 15; however, as should be understood by those having ordinary skill in the art, the principles of Example 15 can be used to make more or less chewable gel units by proportionally increasing or decreasing the amount of ingredients as necessary to produce the desired quantity of chewable gel units.

TABLE 15

| Ingredient Name | Batch Quantity |
|---|---|
| Phenylephrine HCl | 2.000 |
| Bitter blocker powder | 1.800 |
| Carrageenan | 12.400 |
| Citric acid anhydrous | 1.000 |
| Corn syrup (liquid glucose) | 202.400 |
| Flavor agent (tutti frutti flavor) | 0.550 |
| HP.beta.CD | 9.600 |
| Maltitol solution | 42.000 |
| Neotame | 0.250 |
| Pregelatinized starch (starch 1500) | 9.000 |
| Purified water | 175.000 |
| Sodium chloride | 2.500 |
| Sucralose | 2.500 |
| Sucrose | 122.000 |
| Trisodium citrate | 2.000 |

Procedure—Example 15

Step 1: Add about 57.1% of the batch quantity of purified water to a main manufacturing vessel. Slowly add and dissolve the batch quantities of sucralose, neotame, bitter blocker powder, and sodium chloride under continuous stirring until a clear solution is formed.

Step 2: Add the batch quantity of corn syrup to the solution of Step 1 under continuous stirring while heating the mixture to a temperature in the range of about 50° C. to about 55° C. to form a homogenous mixture.

Step 3: Mix the batch quantities of carrageenan and trisodium citrate, and about 32.8% of the batch quantity of sucrose until a homogenous blend is formed.

Step 4: Add the blend of Step 3 to the mixture of Step 2 under continuous stirring while maintaining the temperature of the mixture in the range of about 50° C. to about 55° C. until a homogenous gel is formed.

Step 5: Heat the gel of Step 4 to a temperature in the range of about 90° C. to about 105° C. until a thick gel mixture is observed.

Step 6: Add the batch quantity of maltitol solution and about 67.2% of the batch quantity of sucrose to the gel mixture of Step 5 while maintaining the temperature of the mixture in the range of about 90° C. to about 105° C.

Step 7: Add about 28.6% of the batch quantity of purified water to a container. Slowly add the batch quantity of HP.beta.CD to the purified water under continuous stirring until a clear solution is formed.

Step 8: Add the batch quantity of phenylephrine HCl to the solution of Step 7 under continuous stirring until a clear solution is formed.

Step 9: Combine the solution of Step 8 and the gel mixture formed in Step 6 under stirring and maintain the temperature of the mixture in the range of about 90° C. to about 105° C. until the total solid content of the mixture raises to about 74% w/w or about 74 brix.

Step 10: Add about 14.3% of the batch quantity of purified water and the batch quantity of the flavor agent to a container under stirring until a clear solution is formed.

Step 11: Combine the solution of Step 10 and the gel mixture formed in Step 9 under stirring while maintaining the temperature of the mixture in the range of about 90° C. to about 105° C. to form a gummy mixture.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch and citric acid anhydrous until a homogenous blend is formed.

Step 14: Polish the chewable gel units of Step 12 with the blend of Step 13 for approximately 5 to about 10 minutes to form polished chewable gel units.

Step 15: Store the chewable gel units of Step 14 for curing at a temperature in the range of about 25° C. to about 35° C. for 5 to 7 days.

Step 16: Transfer the chewable gel units of Step 15 into suitable packaging.

Example 16

A process for making chewable gel units in accordance with certain aspects of the present invention is provided in Example 16 below. The ingredients corresponding to Example 16 are tabulated in Table 16 with the amount of each ingredient used in the process (i.e., the batch quantity) given in grams. In Example 16 the active ingredient is acetaminophen. Each chewable gel unit formed in accordance with Example 16 has an active strength of acetaminophen of about 160 mg. Each chewable gel unit formed by the process of Example 16 has a mass of about 4,600 mg. One thousand (1,000) chewable gel units are formed by the process of Example 16; however, as should be understood by those having ordinary skill in the art, the principles of Example 16 can be used to make more or less chewable gel units by proportionally increasing or decreasing the amount of ingredients as necessary to produce the desired quantity of chewable gel units.

TABLE 16

| Ingredient Name | Batch Quantity |
| --- | --- |
| Acetaminophen | 161.560 |
| Bitter blocker powder | 26.490 |
| Carrageenan | 130.000 |
| Color agent (FD&C red #40) | 0.010 |
| Corn syrup (liquid glucose) | 1900.000 |
| Flavor agent (orange flavor) | 2.500 |
| HP.beta.CD | 400.000 |
| Maltitol solution | 516.000 |
| Neotame | 1.000 |
| Pregelatinized starch (starch 1500) | 100.000 |
| Purified water | 1640.000 |
| Sodium chloride | 26.000 |
| Sucralose | 26.000 |
| Sucrose | 900.000 |
| Trisodium citrate | 22.000 |

Procedure—Example 16

Step 1: Add about 97.5% of the batch quantity of purified water to a container. Slowly add the batch quantity of HP.beta.CD to the purified water under continuous stirring until a clear solution is formed.

Step 2: Add the batch quantity of acetaminophen to the solution of Step 1 under continuous stirring until a clear solution is formed and heat to a temperature in the range of about 70° C. to about 80° C.

Step 3: Slowly add and dissolve the batch quantities of sucralose, neotame, bitter blocker powder, and sodium chloride in the solution of Step 2 under continuous stirring until a clear solution is formed.

Step 4: Add the batch quantity of corn syrup to the solution of Step 3 under continuous stirring while maintaining the temperature of the mixture in the range of about 50° C. to about 55° C. to form a homogenous mixture.

Step 5: Mix the batch quantities of carrageenan and trisodium citrate, and about 44.4% of the batch quantity of sucrose until a homogenous blend is formed.

Step 6: Add the blend of Step 5 to the mixture of Step 4 under continuous stirring while maintaining the temperature of the mixture in the range of about 50° C. to about 55° C. until a homogenous gel is formed.

Step 7: Heat the gel of Step 6 to a temperature in the range of about 90° C. to about 105° C. until a thick gel mixture is observed.

Step 8: Add the batch quantity of maltitol solution and about 55.6% of the batch quantity of sucrose to the gel mixture of Step 7 while maintaining the temperature of the mixture in the range of about 90° C. to about 105° C.

Step 9: Maintain the temperature of the gel mixture of Step 8 in the range of about 90° C. to about 105° C. until the total solid content of the mixture raises to about 74% w/w or about 74 brix.

Step 10: Add about 2.5% of the batch quantity of purified water and the batch quantities of the flavor agent and the color agent to a container under stirring until a clear solution is formed.

Step 11: Add the solution of Step 10 to the gel mixture formed in Step 9 under stirring while maintaining the temperature of the mixture in the range of about 90° C. to about 105° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Polish the chewable gel units of Step 12 with the batch quantity of pregelatinized starch for approximately 5 to about 10 minutes to form polished chewable gel units.

Step 14: Store the chewable gel units of Step 13 for curing at a temperature in the range of about 25° C. to about 35° C. for 5 to 7 days.

Step 15: Transfer the chewable gel units of Step 14 into suitable packaging.

Example 17

A process for making chewable gel units in accordance with certain aspects of the present invention is provided in Example 17 below. The ingredients corresponding to Example 17 are tabulated in Table 17 with the amount of each ingredient used in the process (i.e., the batch quantity) given in grams. In Example 17 the active ingredient is diphenhydramine HCl. Each chewable gel unit formed in accordance with Example 17 has an active strength of diphenhydramine HCl of about 25 mg. Each chewable gel unit formed by the process of Example 17 has a mass of about 4,090 mg. Eight hundred (800) chewable gel units are formed by the process of Example 17; however, as should be understood by those having ordinary skill in the art, the principles of Example 17 can be used to make more or less chewable gel units by proportionally increasing or decreasing the amount of ingredients as necessary to produce the desired quantity of chewable gel units.

TABLE 17

| Ingredient Name | Batch Quantity |
| --- | --- |
| Diphenhydramine HCl | 20.000 |
| Bitter blocker powder | 12.000 |
| Carrageenan | 80.000 |
| Citric acid anhydrous | 6.400 |
| Color agent (FD&C red #40) | 0.130 |
| Corn syrup (liquid glucose) | 1280.000 |
| Flavor agent (strawberry flavor) | 8.000 |
| HP.beta.CD | 80.000 |
| Magnesium stearate | 8.000 |
| Maltitol solution | 259.870 |
| Neotame | 0.800 |
| Pregelatinized starch (starch 1500) | 57.600 |
| Purified water | 1120.000 |
| Sodium chloride | 12.000 |
| Sucralose | 11.200 |
| Sucrose | 784.000 |
| Trisodium citrate | 12.000 |

Procedure—Example 17

Step 1: Add about 17.9% of the batch quantity of purified water to a container. Slowly add the batch quantity of HP.beta.CD to the purified water under continuous stirring until a clear solution is formed.

Step 2: Add the batch quantity of diphenhydramine HCl to the solution of Step 1 under continuous stirring until a clear solution is formed.

Step 3: Add about 77.7% of the batch quantity of purified water to the solution of Step 3 and slowly add the batch quantities of sucralose, neotame, bitter blocker powder, and sodium chloride thereto under continuous stirring until a clear solution is formed.

Step 4: Add the batch quantity of corn syrup to the solution of Step 3 under continuous stirring while heating the mixture to a temperature in the range of about 50° C. to about 55° C. to form a homogenous mixture.

Step 5: Mix the batch quantities of carrageenan, trisodium citrate, and sucrose until a homogenous blend is formed.

Step 6: Add the blend of Step 5 to the mixture of Step 4 under continuous stirring while maintaining the temperature of the mixture in the range of about 50° C. to about 55° C. until a homogenous gel is formed.

Step 7: Heat the gel of Step 6 to a temperature in the range of about 90° C. to about 105° C. until a thick gel mixture is observed.

Step 8: Add the batch quantity of maltitol solution to the gel mixture of Step 7 while maintaining the temperature of the mixture in the range of about 90° C. to about 105° C.

Step 9: Maintain the temperature of the gel mixture formed in Step 8 in the range of about 90° C. to about 105° C. until the total solid content of the mixture raises to about 74% w/w or about 74 brix.

Step 10: Add about 4.4% of the batch quantity of purified water and the batch quantities of the flavor agent and the color agent to a container under stirring until a clear solution is formed.

Step 11: Add the solution of Step 10 to the gel mixture formed in Step 9 under stirring while maintaining the temperature of the mixture in the range of about 90° C. to about 105° C. to form a gummy mixture.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Collect the chewable gel units of Step 14 on curing trays and store for curing at a temperature in the range of about 25° C. to about 35° C. for 5 to 7 days.

Step 16: Transfer the chewable gel units of Step 15 into suitable packaging.

Example 18

A process for making chewable gel units in accordance with certain aspects of the present invention is provided in Example 18 below. The ingredients corresponding to Example 18 are tabulated in Table 18 with the amount of each ingredient used in the process (i.e., the batch quantity) given in kilograms. In Example 18 the active ingredient is diphenhydramine HCl. Each chewable gel unit formed in accordance with Example 18 has an active strength of diphenhydramine HCl of about 25 mg. Each chewable gel unit formed by the process of Example 18 has a mass of about 3,600 mg. Ninety thousand (90,000) chewable gel units are formed by the process of Example 18; however, as should be understood by those having ordinary skill in the art, the principles of Example 18 can be used to make more or less chewable gel units by proportionally increasing or decreasing the amount of ingredients as necessary to produce the desired quantity of chewable gel units.

TABLE 18

| Ingredient Name | Batch Quantity |
| --- | --- |
| Diphenhydramine HCl | 2.250 |
| Bitter blocker powder | 1.350 |
| Carrageenan | 9.000 |
| Citric acid anhydrous | 1.080 |
| Color agent (FD&C red #40) | 0.009 |
| Corn syrup (liquid glucose) | 144.000 |
| Flavor agent (tutti frutti flavor) | 0.630 |
| HP.beta.CD | 9.000 |
| Magnesium stearate | 1.350 |
| Maltitol solution | 29.240 |
| Neotame | 0.090 |
| Pregelatinized starch (starch 1500) | 9.720 |
| Purified water | 136.000 |
| Sodium chloride | 1.350 |
| Sucralose | 1.260 |
| Sucrose | 88.470 |
| Trisodium citrate | 1.350 |

Procedure—Example 18

Step 1: Add about 97.8% of the batch quantity of purified water to a container. Slowly add the batch quantity of HP.beta.CD to the purified water under continuous stirring until a clear solution is formed.

Step 2: Add the batch quantity of diphenhydramine HCl to the solution of Step 1 under continuous stirring until a clear solution is formed and heat to a temperature in the range of about sixty degrees Celsius (60° C.) to about 70° C.

Step 3: Slowly add the batch quantities of sucralose, neotame, bitter blocker powder, and sodium chloride to the solution of Step 2 under continuous stirring until a clear solution is formed.

Step 4: Add the batch quantity of corn syrup to the solution of Step 3 under continuous stirring while maintaining the temperature of the mixture in the range of about 50° C. to about 55° C. to form a homogenous mixture.

Step 5: Mix the batch quantities of carrageenan and trisodium citrate, and about 11.3% of the batch quantity of sucrose until a homogenous blend is formed.

Step 6: Add the blend of Step 5 to the mixture of Step 4 under continuous stirring while maintaining the temperature of the mixture in the range of about 50° C. to about 55° C. until a homogenous gel is formed.

Step 7: Heat the gel of Step 6 to a temperature in the range of about 90° C. to about 105° C. until a thick gel mixture is observed.

Step 8: Add the batch quantity of maltitol solution and about 88.7% of the batch quantity of sucrose to the gel mixture formed in Step 7 while maintaining the temperature of the mixture in the range of about 90° C. to about 105° C.

Step 9: Maintain the temperature of the gel mixture formed in Step 8 in the range of about 90° C. to about 105° C. until the total solid content of the mixture raises to about 74% w/w or about 74 brix.

Step 10: Add about 2.2% of the batch quantity of purified water and the batch quantities of the flavor agent and the color agent to a container under stirring until a clear solution is formed.

Step 11: Add the solution of Step 10 to the gel mixture formed in Step 9 under stirring while maintaining the temperature of the mixture in the range of about 80° C. to about 90° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Collect the chewable gel units of Step 14 on curing trays and store for curing at a temperature in the range of about 25° C. to about 35° C. for three (3) to five (5) days.

Step 16: Transfer the chewable gel units of Step 15 into suitable packaging.

Example 19

A process for making chewable gel units in accordance with certain aspects of the present invention is provided in Example 19 below. The ingredients corresponding to Example 19 are tabulated in Table 19 with the amount of each ingredient used in the process (i.e., the batch quantity) given in grams. In Example 19 the active ingredient is dimenhydrinate. Each chewable gel unit formed in accordance with Example 19 has an active strength of dimenhydrinate of about 50 mg. Each chewable gel unit formed by the process of Example 19 has a mass of about 4,390 mg. One thousand (1,000) chewable gel units are formed by the process of Example 19; however, as should be understood by those having ordinary skill in the art, the principles of Example 19 can be used to make more or less chewable gel units by proportionally increasing or decreasing the amount of ingredients as necessary to produce the desired quantity of chewable gel units.

TABLE 19

| Ingredient Name | Batch Quantity |
|---|---|
| Dimenhydrinate | 50.000 |
| Bitter blocker powder | 23.900 |
| Carrageenan | 130.000 |
| Citric acid anhydrous | 8.000 |
| Color agent (FD&C yellow #6) | 0.100 |
| Corn syrup (liquid glucose) | 1800.000 |
| Flavor agent (orange flavor) | 6.000 |
| HP.beta.CD | 400.000 |
| Magnesium stearate | 10.000 |
| Maltitol solution | 526.000 |
| Neotame | 1.000 |
| Pregelatinized starch (starch 1500) | 72.000 |
| Purified water | 1640.000 |
| Sodium chloride | 26.000 |
| Sucralose | 25.000 |
| Sucrose | 850.000 |
| Trisodium citrate | 22.000 |

Procedure—Example 19

Step 1: Add about 91.5% of the batch quantity of purified water to a container. Slowly add the batch quantity of HP.beta.CD to the purified water under continuous stirring until a clear solution is formed.

Step 2: Add the batch quantity of dimenhydrinate to the solution of Step 1 under continuous stirring until a clear solution is formed.

Step 3: Slowly add and dissolve the batch quantities of sucralose, neotame, bitter blocker powder, and sodium chloride in the solution of Step 2 under continuous stirring to form a clear solution.

Step 4: Add the batch quantity of corn syrup to the solution of Step 3 under continuous stirring while heating the mixture to a temperature in the range of about 55° C. to about 60° C. to form a homogenous mixture.

Step 5: Mix the batch quantities of carrageenan and trisodium citrate, and about 41.2% of the batch quantity of sucrose until a homogenous blend is formed.

Step 6: Add the blend of Step 5 to the mixture of Step 4 under continuous stirring while maintaining the temperature of the mixture in the range of about 50° C. to about 55° C. until a homogenous gel is formed.

Step 7: Heat the gel of Step 6 to a temperature in the range of about 90° C. to about 95° C. until a thick gel mixture is formed.

Step 8: Add the batch quantity of maltitol solution and about 58.8% of the batch quantity of sucrose to the gel mixture of Step 7 while maintaining the temperature of the mixture in the range of about 90° C. to about 95° C.

Step 9: Maintain the temperature of the gel mixture formed in Step 8 in the range of about 90° C. to about 105° C. until the total solid content of the mixture raises to about seventy percent by weight (70% w/w) or about seventy brix (70 brix).

Step 10: Add about 8.5% of the batch quantity of purified water and the batch quantities of the flavor agent and the color agent to a container under stirring until a clear solution is formed.

Step 11: Add the solution of Step 10 to the gel mixture formed in Step 9 under stirring while maintaining the temperature of the mixture in the range of about 80° C. to about 90° C. to form a gummy mixture.

Step 12: Transfer the gummy mixture of Step 11 to a product mold. Allow the gummy mixture to cool at room temperature for about 10 to about 15 minutes and then remove the individual chewable gel units from the mold.

Step 13: Mix the batch quantities of pregelatinized starch, citric acid anhydrous, and magnesium stearate until a homogenous blend is formed.

Step 14: Polish the chewable gel units of Step 12 with the blend of Step 13 for approximately 5 to about 10 minutes to form polished chewable gel units.

Step 15: Collect the chewable gel units of Step 14 on curing trays and store for curing at a temperature in the range of about 25° C. to about 35° C. for 3 to 5 days.

Step 16: Transfer the chewable gel units of Step 15 into suitable packaging.

Example 20

A process for making chewable gel units in accordance with certain aspects of the present invention is provided in Example 20 below. The ingredients corresponding to Example 20 are tabulated in Table 20 with the amount of each ingredient used in the process (i.e., the batch quantity) given in grams. In Example 20 the active ingredient is dextromethorphan HBr. Each chewable gel unit formed in accordance with Example 20 has an active strength of dextromethorphan HBr of about 15 mg. Each chewable gel unit formed by the process of Example 20 has a mass of about 2,300 mg. One thousand (1,000) chewable gel units are formed by the process of Example 20; however, as should be understood by those having ordinary skill in the art, the principles of Example 20 can be used to make more or less chewable gel units by proportionally increasing or decreasing the amount of ingredients as necessary to produce the desired quantity of chewable gel units.

TABLE 20

| Ingredient Name | Batch Quantity |
| --- | --- |
| Dextromethorphan HBr | 15.760 |
| Bitter blocker powder | 10.000 |
| Carrageenan | 66.000 |
| Color agent (FD&C yellow #5) | 0.030 |
| Corn syrup (liquid glucose) | 975.000 |
| Flavor agent (sweet grape flavor) | 2.000 |
| HP.beta.CD | 187.000 |
| Maltitol solution | 210.000 |
| Neotame | 1.000 |
| Pregelatinized starch (starch 1500) | 55.000 |
| Purified water | 900.000 |
| Sodium chloride | 10.000 |
| Sucralose | 12.000 |
| Sucrose | 600.210 |
| Trisodium citrate | 11.000 |

Procedure—Example 20

Step 1: Add about 94.4% of the batch quantity of purified water to a container. Slowly add the batch quantity of HP.beta.CD to the purified water under continuous stirring until a clear solution is formed.

Step 2: Add the batch quantity of dextromethorphan HBr to the solution of Step 1 under continuous stirring until a clear solution is formed.

Step 3: Slowly add the batch quantities of sucralose, neotame, bitter blocker powder, and sodium chloride to the solution of Step 2 under continuous stirring until a clear solution is formed.

Step 4: Add the batch quantity of corn syrup to the solution of Step 3 under continuous stirring while heating the mixture to a temperature in the range of about 50° C. to about 55° C. until a homogenous mixture is formed.

Step 5: Mix the batch quantities of carrageenan and trisodium citrate, and about 8.3% of the batch quantity of sucrose until a homogenous blend is formed.

Step 6: Add the blend of Step 5 to the mixture of Step 4 under continuous stirring while maintaining the temperature of the mixture in the range of about 50° C. to about 55° C. until a homogenous gel is formed.

Step 7: Heat the gel of Step 6 to a temperature in the range of about 90° C. to about 105° C. until a thick gel mixture is observed.

Step 8: Add the batch quantity of maltitol solution and about 91.7% of the batch quantity of sucrose to the gel mixture of Step 7 while maintaining the temperature of the mixture in the range of about 90° C. to about 105° C.

Step 9: Maintain the temperature of the gel mixture formed in Step 8 in the range of about 90° C. to about 105° C. until the total solid content of the mixture raises to about 70% w/w or about 70 brix.

Step 10: Add about 5.6% of the batch quantity of purified water and the batch quantities of the flavor agent and the color agent to a container under stirring until a clear solution is formed.

Step 11: Add the solution of Step 10 to the gel mixture formed in Step 9 under stirring while maintaining the temperature of the mixture in the range of about 90° C. to about 95° C. until a gummy mixture is formed.

Step 12: Transfer the gummy mixture of Step 11 to a product mold. Allow the gummy mixture to cool at room temperature for about 10 to about 15 minutes and then remove the individual chewable gel units from the mold.

Step 13: Polish the chewable gel units of Step 12 with the batch quantity of pregelatinized starch for approximately 5 to about 10 minutes to form polished chewable gel units.

Step 14: Collect the chewable gel units of Step 13 on curing trays and store for curing at a temperature in the range of about 25° C. to about 35° C. for 3 to 5 days.

Step 15: Transfer the chewable gel units of Step 14 into suitable packaging.

Example 21

A process for making chewable gel units in accordance with certain aspects of the present invention is provided in Example 21 below. The ingredients corresponding to Example 21 are tabulated in Table 21 with the amount of each ingredient used in the process (i.e., the batch quantity) given in grams. In Example 21 the active ingredient is dextromethorphan HBr. Each chewable gel unit formed in accordance with Example 21 has an active strength of dextromethorphan HBr of about 30 mg. Each chewable gel unit formed by the process of Example 21 has a mass of about 4,600 mg. One hundred fifty (150) chewable gel units are formed by the process of Example 21; however, as should be understood by those having ordinary skill in the art, the principles of Example 21 can be used to make more or less chewable gel units by proportionally increasing or decreasing the amount of ingredients as necessary to produce the desired quantity of chewable gel units.

TABLE 21

| Ingredient Name | Batch Quantity |
|---|---|
| Dextromethorphan HBr | 4.730 |
| Bitter blocker powder | 3.660 |
| Carrageenan | 18.000 |
| Color agent (FD&C yellow #5) | 0.010 |
| Corn syrup (liquid glucose) | 283.800 |
| Flavor agent (sweet grape flavor) | 0.900 |
| HP.beta.CD | 75.000 |
| Maltitol solution | 75.000 |
| Neotame | 0.150 |
| Pregelatinized starch (starch 1500) | 15.000 |
| Purified water | 240.000 |
| Sodium chloride | 3.750 |
| Sucralose | 4.500 |
| Sucrose | 150.000 |
| Trisodium citrate | 3.000 |

Procedure—Example 21

Step 1: Add about 91.7% of the batch quantity of purified water to a container. Slowly add the batch quantity of HP.beta.CD to the purified water under continuous stirring until a clear solution is formed.

Step 2: Add the batch quantity of dextromethorphan HBr to the solution of Step 1 under continuous stirring until a clear solution is formed.

Step 3: Slowly add and dissolve the batch quantities of sucralose, neotame, bitter blocker powder, and sodium chloride in the solution of Step 2 under continuous stirring to form a clear solution.

Step 4: Add the batch quantity of corn syrup to the solution of Step 3 under continuous stirring while heating the mixture to a temperature in the range of about 55° C. to about 60° C. to form a homogenous mixture.

Step 5: Mix the batch quantities of carrageenan and trisodium citrate, and about 8.3% of the batch quantity of sucrose until a homogenous blend is formed.

Step 6: Add the blend of Step 5 to the mixture of Step 4 under continuous stirring while maintaining the temperature of the mixture in the range of about 50° C. to about 60° C. until a homogenous gel is formed.

Step 7: Heat the gel of Step 6 to a temperature in the range of about 90° C. to about 105° C. until a thick gel mixture is formed.

Step 8: Add the batch quantity of maltitol solution and about 91.7% of the batch quantity of sucrose to the gel mixture of Step 7 while maintaining the temperature of the mixture in the range of about 90° C. to about 105° C.

Step 9: Maintain the temperature of the gel mixture formed in Step 8 in the range of about 90° C. to about 105° C. until the total solid content of the mixture raises to about 70% w/w or about 70 brix.

Step 10: Add about 8.3% of the batch quantity of purified water and the batch quantities of the flavor agent and the color agent to a container under stirring until a clear solution is formed.

Step 11: Add the solution of Step 10 to the gel mixture formed in Step 9 under stirring while maintaining the temperature of the mixture in the range of about 90° C. to about 95° C. to form a gummy mixture.

Step 12: Transfer the gummy mixture of Step 11 to a product mold. Allow the gummy mixture to cool at room temperature for about 10 to about 15 minutes and then remove the individual chewable gel units from the mold.

Step 13: Polish the chewable gel units of Step 12 with the batch quantity of pregelatinized starch for approximately 5 to about 10 minutes to form polished chewable gel units.

Step 14: Collect the chewable gel units of Step 13 on curing trays and store for curing at a temperature in the range of about 25° C. to about 35° C. for 3 to 5 days.

Step 15: Transfer the chewable gel units of Step 14 into suitable packaging.

Example 22

A process for making chewable gel units in accordance with certain aspects of the present invention is provided in Example 22 below. The ingredients corresponding to Example 22 are tabulated in Table 22 with the amount of each ingredient used in the process (i.e., the batch quantity) given in grams. In Example 22 the active ingredient is diphenhydramine HCl. Each chewable gel unit formed in accordance with Example 22 has an active strength of diphenhydramine HCl of about 25 mg. Each chewable gel unit formed by the process of Example 22 has a mass of about 3,600 mg. Two hundred fifty (250) chewable gel units are formed by the process of Example 22; however, as should be understood by those having ordinary skill in the art, the principles of Example 22 can be used to make more or less chewable gel units by proportionally increasing or decreasing the amount of ingredients as necessary to produce the desired quantity of chewable gel units.

TABLE 22

| Ingredient Name | Batch Quantity |
|---|---|
| Diphenhydramine HCl | 6.250 |
| Bitter blocker powder | 3.750 |
| Carrageenan | 25.000 |
| Citric acid anhydrous | 2.030 |
| Color agent (FD&C red #40) | 0.030 |
| Corn syrup (liquid glucose) | 400.000 |
| Ethanol | 18.750 |
| Flavor agent (tutti frutti flavor) | 1.750 |
| HP.beta.CD | 50.000 |
| Magnesium stearate | 2.030 |
| Maltitol solution | 81.230 |
| Mono-diglycerides | 6.250 |
| Neotame | 0.250 |
| Pregelatinized starch (starch 1500) | 18.450 |
| Purified water | 325.000 |
| Sodium chloride | 3.750 |
| Sucralose | 3.500 |
| Sucrose | 245.750 |
| Trisodium citrate | 3.750 |

Procedure—Example 22

Step 1: Add the batch quantities of ethanol and diphenhydramine HCl to a container under continuous stirring while heating the mixture to a temperature in the range of about 70° C. to about 80° C. until a clear solution is formed.

Step 2: Add the batch quantity of mono-diglycerides to the solution of Step 1 under continuous stirring while maintaining the temperature of the mixture in the range of about 70° C. to about 80° C. until a clear solution is formed.

Step 3: Add about 6.2% of the batch quantity of purified water to the solution of Step 3 under continuous stirring while maintaining the temperature of the mixture in the range of about 70° C. to about 80° C. until a clear solution is formed.

Step 4: Add about 87.7% of the batch quantity of purified water to a container. Slowly add the batch quantity of HP.beta.CD to the purified water under continuous stirring until a clear solution is formed.

Step 5: Slowly add the batch quantities of sucralose, neotame, bitter blocker powder, and sodium chloride to the solution of Step 4 under continuous stirring until a clear solution is formed.

Step 6: Add the batch quantity of corn syrup to the solution of Step 5 under continuous stirring while heating the mixture to a temperature above about 50° C. to form a homogenous mixture.

Step 7: Combine the solution of Step 3 and the mixture of Step 6 under continuous stirring while maintaining the temperature of the mixture above about 70° C. until a homogenous gel is formed.

Step 8: Mix the batch quantities of carrageenan and trisodium citrate, and about 10.2% of the batch quantity of sucrose until a homogenous blend is formed.

Step 9: Add the blend of Step 8 to the gel of Step 7 under continuous stirring while maintaining the temperature of the mixture above seventy-five degrees Celsius (75° C.) until a homogenous gel is formed.

Step 10: Heat the gel of Step 9 to a temperature in the range of about 85° C. to about one hundred degrees Celsius (100° C.) until a thick gel mixture is observed.

Step 11: Add the batch quantity of maltitol solution and about 89.8% of the batch quantity of sucrose to the gel mixture of Step 10 while heating the mixture to a temperature in the range of about 95° C. to about 105° C.

Step 12: Maintain the temperature of the gel mixture formed in Step 11 in the range of about 95° C. to about 105° C. until the total solid content of the mixture raises to about 70% w/w or about 70 brix.

Step 13: Add about 6.1% of the batch quantity of purified water and the batch quantities of the flavor agent and the color agent to a container under stirring until a clear solution is formed.

Step 14: Add the solution of Step 13 to the gel mixture formed in Step 12 under stirring while maintaining the temperature of the mixture in the range of about 80° C. to about 90° C. until a gummy mixture is formed.

Step 15: Transfer the gummy mixture of Step 14 to a product mold. Allow the gummy mixture to cool at room temperature for about 10 to about 15 minutes and then remove the individual chewable gel units from the mold.

Step 16: Mix the batch quantities of pregelatinized starch, citric acid anhydrous, and magnesium stearate until a homogenous blend is formed.

Step 17: Polish the chewable gel units of Step 15 with the blend of Step 16 for approximately 5 to about 10 minutes to form polished chewable gel units.

Step 18: Store the polished chewable gel units of Step 17 for curing at a temperature in the range of about 25° C. to about 35° C. for 5 to 7 days.

Step 19: Transfer the cured chewable gel units of Step 18 into suitable packaging.

Example 23

A process for making chewable gel units in accordance with certain aspects of the present invention is provided in Example 23 below. The ingredients corresponding to Example 23 are tabulated in Table 23 with the amount of each ingredient used in the process (i.e., the batch quantity) given in grams. In Example 23 the active ingredient is loratadine. Each chewable gel unit formed in accordance with Example 23 has an active strength of loratadine of about 10 mg. Each chewable gel unit formed by the process of Example 23 has a mass of about 3,700 mg. One thousand (1,000) chewable gel units are formed by the process of Example 23; however, as should be understood by those having ordinary skill in the art, the principles of Example 23 can be used to make more or less chewable gel units by proportionally increasing or decreasing the amount of ingredients as necessary to produce the desired quantity of chewable gel units.

TABLE 23

| Ingredient Name | Batch Quantity |
| --- | --- |
| Loratadine | 10.000 |
| Bitter blocker powder | 14.600 |
| Carrageenan | 100.000 |
| Citric acid anhydrous | 5.000 |
| Color agent (FD&C yellow #5) | 1.000 |
| Corn syrup (liquid glucose) | 1300.000 |
| Ethanol | 55.000 |
| Flavor agent (sweet grape flavor) | 3.400 |
| HP.beta.CD | 240.000 |
| Maltitol solution | 540.000 |
| Neotame | 1.000 |
| Pregelatinized starch (starch 1500) | 80.000 |
| Purified water | 1350.000 |
| Sucralose | 20.000 |
| Sucrose | 920.000 |
| Trisodium citrate | 40.000 |

Procedure—Example 23

Step 1: Add the batch quantities of ethanol and loratadine to a container under continuous stirring until a clear solution is formed.

Step 2: Add about 7.4% of the batch quantity of purified water to the solution of Step 1 under continuous stirring while heating the mixture to a temperature in the range of about 70° C. to about 80° C. until a clear solution is formed.

Step 3: Add about 18.5% of the batch quantity of purified water to a container. Slowly add the batch quantities of HP.beta.CD, citric acid anhydrous, and sucralose to the purified water under continuous stirring while heating the mixture to a temperature in the range of about 70° C. to about 80° C. until a clear solution is formed.

Step 4: Combine the solution of Step 2 and the solution of Step 3 under continuous stirring while maintaining the temperature of the mixture in the range of about 70° C. to about 80° C. to evaporate ethanol from the solution.

Step 5: Add about 66.7% of the batch quantity of purified water to a container. Slowly add and dissolve the batch quantities of neotame and bitter blocker powder under continuous stirring until a clear solution is formed.

Step 6: Add the batch quantity of corn syrup to the solution of Step 5 under continuous stirring while heating the mixture to a temperature in the range of about 55° C. to about 60° C. to form a homogenous mixture.

Step 7: Mix the batch quantities of carrageenan and trisodium citrate, and about 34.8% of the batch quantity of sucrose until a homogenous blend is formed.

Step 8: Add the blend of Step 7 to the mixture of Step 6 under continuous stirring while maintaining the temperature of the mixture in the range of about 50° C. to about 60° C. until a homogenous gel is formed.

Step 9: Add the batch quantity of maltitol solution and about 65.2% of the batch quantity of sucrose to the gel of Step 8 and heat to a temperature in the range of about 85° C. to about 95° C.

Step 10: Combine the solution of Step 4 and the gel mixture formed in Step 9 under stirring while heating the mixture to a temperature in the range of about 95° C. to about 105° C. until a thick gel mixture is formed.

Step 11: Add about 7.4% of the batch quantity of purified water and the batch quantities of the flavor agent and the color agent to a container under stirring until a clear solution is formed.

Step 12: Add the solution of Step 11 to the gel mixture of Step 10 under stirring while maintaining the temperature of the mixture in the range of about 95° C. to about 105° C.

Step 13: Maintain the temperature of the gel mixture formed in Step 12 in the range of about 95° C. to about 105° C. until the total solid content of the mixture raises to about seventy-two percent by weight (72% w/w) or about seventy-two brix (72 brix) to form a gummy mixture.

Step 14: Transfer the gummy mixture of Step 13 to a product mold. Allow the gummy mixture to cool at room temperature for about 10 to about 15 minutes and then remove the individual chewable gel units from the mold.

Step 15: Delump the batch quantity of pregelatinized starch using a #40 mesh to form a homogenous powder.

Step 16: Polish the chewable gel units of Step 14 with the powder of Step 15 for approximately 5 to about 10 minutes to form polished chewable gel units.

Step 17: Store the polished chewable gel units of Step 16 for curing at a temperature in the range of about 35° C. to about forty-three degrees Celsius (43° C.) for 3 to 5 days.

Step 18: Transfer the cured chewable gel units of Step 17 into suitable packaging.

Example 24

A process for making chewable gel units in accordance with certain aspects of the present invention is provided in Example 24 below. The ingredients corresponding to Example 24 are tabulated in Table 24, with the amount of each ingredient used in the process (i.e., the batch quantity) given in grams. In Example 24, the active ingredient is acetaminophen. Each chewable gel unit formed in accordance with Example 24 has an active strength of acetaminophen of about 325 mg. Each chewable gel unit formed by the process of Example 24 has a mass of about 4,600 mg. Two hundred (200) chewable gel units are formed by the process of Example 24; however, as should be understood by those having ordinary skill in the art, the principles of Example 24 can be used to make more or less chewable gel units by proportionally increasing or decreasing the amount of ingredients as necessary to produce the desired quantity of chewable gel units.

TABLE 24

| Ingredient Name | Batch Quantity |
| --- | --- |
| Acetaminophen | 65.000 |
| Bitter blocker powder | 5.300 |
| Carrageenan | 26.000 |
| Color agent (FD&C yellow #6) | 0.010 |
| Corn syrup (liquid glucose) | 346.100 |
| Flavor agent (orange flavor) | 1.500 |
| HP.beta.CD | 80.000 |
| Maltitol solution | 103.200 |
| Neotame | 0.200 |
| Polyethylene glycol 400 (PEG 400) | 115.000 |
| Povidone (K30) | 23.000 |
| Pregelatinized starch (starch 1500) | 20.000 |
| Propylene glycol | 10.900 |

TABLE 24-continued

| Ingredient Name | Batch Quantity |
| --- | --- |
| Purified water | 200.000 |
| Sodium chloride | 5.200 |
| Sucralose | 5.200 |
| Sucrose | 160.000 |
| Trisodium citrate | 4.400 |

Procedure—Example 24

Step 1: Add the batch quantities of polyethylene glycol 400 and propylene glycol to a container under continuous stirring while heating the mixture to a temperature in the range of about 70° C. to about 80° C. until a clear solution is formed.

Step 2: Add the batch quantity of povidone K-30 to the solution of Step 1 under continuous stirring while maintaining the temperature of the mixture in the range of about 70° C. to about 80° C. until a clear solution is formed.

Step 3: Add the batch quantity of acetaminophen to the solution of Step 2 under continuous stirring while maintaining the temperature of the mixture in the range of about 70° C. to about 80° C. until a clear solution is formed.

Step 4: Add about 95.0% of the batch quantity of purified water to a container. Slowly add the batch quantity of HP.beta.CD to the purified water under continuous stirring until a clear solution is formed.

Step 5: Slowly add and dissolve the batch quantities of sucralose, neotame, bitter blocker powder, and sodium chloride in the solution of Step 4 under continuous stirring to form a clear solution.

Step 6: Add the batch quantity of corn syrup to the solution of Step 5 under continuous stirring while heating the mixture to a temperature above about 50° C. to form a homogenous mixture.

Step 7: Combine the solution of Step 3 and the mixture of Step 6 under continuous stirring while heating the mixture to a temperature above about 70° C. until a homogenous mixture is formed.

Step 8: Mix the batch quantities of carrageenan and trisodium citrate, and about 16.3% of the batch quantity of sucrose until a homogenous blend is formed.

Step 9: Combine the blend of Step 8 and the mixture of Step 7 under continuous stirring while heating the mixture to a temperature above 75° C. until a homogenous gel is formed.

Step 10: Heat the gel of Step 9 to a temperature in the range of about 85° C. to about 100° C. until a thick gel mixture is observed.

Step 11: Add the batch quantity of maltitol solution and about 83.7% of the batch quantity of sucrose to the gel mixture of Step 10 while heating the mixture to a temperature in the range of about 95° C. to about 105° C.

Step 12: Maintain the temperature of the gel mixture formed in Step 11 in the range of about 95° C. to about 105° C. until the total solid content of the mixture raises to about eighty percent by weight (80% w/w) or about eighty brix (80 brix).

Step 13: Add about 5.0% of the batch quantity of purified water and the batch quantities of the flavor agent and the color agent to a container under stirring until a clear solution is formed.

Step 14: Add the solution of Step 13 to the gel mixture formed in Step 12 under continuous stirring while maintaining the temperature of the mixture in the range of about 80° C. to about 90° C. to form a gummy mixture.

Step 15: Transfer the gummy mixture of Step 14 to a product mold. Allow the gummy mixture to cool at room temperature for about 10 to about 15 minutes and then remove the individual chewable gel units from the mold.

Step 16: Delump the batch quantity of pregelatinized starch using a #40 mesh to form a homogenous powder.

Step 17: Polish the chewable gel units of Step 15 with the powder of Step 16 for approximately 5 to about 10 minutes to form polished chewable gel units.

Step 18: Store the polished chewable gel units of Step 17 on curing trays and store for curing at a temperature in the range of about 25° C. to about 35° C. for 3 to 5 days.

Step 19: Transfer the cured chewable gel units of Step 18 into suitable packaging.

Example 25

A process for making chewable gel units in accordance with certain aspects of the present invention is provided in Example 25 below. The ingredients corresponding to Example 25 are tabulated in Table 25 with the amount of each ingredient used in the process (i.e., the batch quantity) given in grams. In Example 25 the active ingredient is dextromethorphan HBr. Each chewable gel unit formed in accordance with Example 25 has an active strength of dextromethorphan HBr of about 30 mg. Each chewable gel unit formed by the process of Example 25 has a mass of about 4,600 mg. Two hundred (200) chewable gel units are formed by the process of Example 25; however, as should be understood by those having ordinary skill in the art, the principles of Example 25 can be used to make more or less chewable gel units by proportionally increasing or decreasing the amount of ingredients as necessary to produce the desired quantity of chewable gel units.

TABLE 25

| Ingredient Name | Batch Quantity |
| --- | --- |
| Dextromethorphan HBr | 6.300 |
| Bitter blocker powder | 4.880 |
| Carrageenan | 24.000 |
| Color agent (FD&C yellow #5) | 0.020 |
| Corn syrup (liquid glucose) | 378.400 |
| Ethanol | 11.000 |
| Flavor agent (sweet grape flavor) | 1.200 |
| HP.beta.CD | 100.000 |
| Maltitol solution | 100.000 |
| Neotame | 0.200 |
| Povidone (K30) | 3.000 |
| Pregelatinized starch (starch 1500) | 20.000 |
| Purified water | 309.000 |
| Sodium chloride | 5.000 |
| Sucralose | 6.000 |
| Sucrose | 200.000 |
| Trisodium citrate | 5.000 |

Procedure—Example 25

Step 1: Add the batch quantities of ethanol and dextromethorphan HBr to a container under continuous stirring while heating to a temperature in the range of about 70° C. to about 80° C. until a clear solution is formed.

Step 2: Add the batch quantity of povidone K-30 and about 5.0% of the batch quantity of purified water to the solution of Step 1 under continuous stirring while maintaining the temperature of the mixture in the range of about 70° C. to about 80° C. until a clear solution is formed.

Step 3: Add about 88.5% of the batch quantity of purified water to a container. Slowly add the batch quantity of HP.beta.CD to the purified water under continuous stirring until a clear solution is formed.

Step 4: Slowly add and dissolve the batch quantities of sucralose, neotame, bitter blocker powder, and sodium chloride in the solution of Step 3 under continuous stirring to form a clear solution.

Step 5: Add the batch quantity of corn syrup to the solution of Step 4 under continuous stirring while heating the mixture to a temperature above about 50° C. to form a homogenous mixture.

Step 6: Combine the solution of Step 2 and the mixture of Step 5 under continuous stirring while heating the mixture to a temperature above about 70° C. until a homogenous mixture is formed.

Step 7: Mix the batch quantities of carrageenan and trisodium citrate, and about 10.0% of the batch quantity of sucrose until a homogenous blend is formed.

Step 8: Add the blend of Step 7 to the mixture of Step 6 under continuous stirring while maintaining the temperature of the mixture above 75° C. until a homogenous gel is formed.

Step 9: Continue heating the gel of Step 8 to a temperature in the range of about 85° C. to about 100° C. until a thick gel mixture is observed.

Step 10: Add the batch quantity of maltitol solution and about 90.0% of the batch quantity of sucrose to the gel mixture of Step 9 while maintaining the temperature of the mixture in the range of about 95° C. to about 105° C.

Step 11: Maintain the temperature of the gel mixture formed in Step 10 in the range of about 95° C. to about 105° C. until the total solid content of the mixture raises to about 70% w/w or about 70 brix.

Step 12: Add about 6.5% of the batch quantity of purified water and the batch quantities of the flavor agent and the color agent to a container under stirring until a clear solution is formed.

Step 13: Add the solution of Step 12 in the gel mixture formed in Step 11 under stirring while maintaining the temperature of the mixture in the range of about 80° C. to about 90° C. until a gummy mixture is formed.

Step 14: Transfer the gummy mixture of Step 13 to a product mold. Allow the gummy mixture to cool at room temperature for about 10 to about 15 minutes and then remove the individual chewable gel units from the mold.

Step 15: Delump the batch quantity of pregelatinized starch using a #40 mesh to form a homogenous powder.

Step 16: Polish the chewable gel units of Step 14 with the powder of Step 15 for approximately 5 to about 10 minutes to form polished chewable gel units.

Step 17: Store the polished chewable gel units of Step 16 for curing at a temperature in the range of about 25° C. to about 35° C. for 3 to 5 days.

Step 18: Transfer the cured chewable gel units of Step 17 into suitable packaging.

Example 26

A process for making chewable gel units in accordance with certain aspects of the present invention is provided in Example 26 below. The ingredients corresponding to Example 26 are tabulated in Table 26 with the amount of each ingredient used in the process (i.e., the batch quantity) given in grams. In Example 26 the active ingredient is acetaminophen. Each chewable gel unit formed in accordance with Example 26 has an active strength of acetaminophen of about 325 mg. Each chewable gel unit formed by the process of Example 26 has a mass of about 4,600 mg. Two hundred (200) chewable gel units are formed by the process of Example 26; however, as should be understood by those having ordinary skill in the art, the principles of Example 26 can be used to make more or less chewable gel units by proportionally increasing or decreasing the amount of ingredients as necessary to produce the desired quantity of chewable gel units.

TABLE 26

| Ingredient Name | Batch Quantity |
| --- | --- |
| Acetaminophen | 65.000 |
| Bitter blocker powder | 5.300 |
| Carrageenan | 26.000 |
| Color agent (FD&C yellow #6) | 0.010 |
| Corn syrup (liquid glucose) | 346.100 |
| Flavor agent (orange flavor) | 1.500 |
| HP.beta.CD | 80.000 |
| Maltitol solution | 103.200 |
| Neotame | 0.200 |
| Polyethylene glycol 400 (PEG 400) | 115.000 |
| Povidone (K30) | 23.000 |
| Pregelatinized starch (starch 1500) | 20.000 |
| Propylene glycol | 10.900 |
| Purified water | 200.000 |
| Sodium chloride | 5.200 |
| Sucralose | 5.200 |
| Sucrose | 160.000 |
| Trisodium citrate | 4.400 |

Procedure—Example 26

Step 1: Add the batch quantities of polyethylene glycol 400 and propylene glycol to a container under continuous stirring while heating the mixture to a temperature in the range of about 70° C. to about 80° C. until a clear solution is formed.

Step 2: Add the batch quantity of povidone K-30 to the solution of Step 1 under continuous stirring while maintaining the temperature of the mixture in the range of about 70° C. to about 80° C. until a clear solution is formed.

Step 3: Add the batch quantity of acetaminophen to the solution of Step 2 under continuous stirring while maintaining the temperature of the mixture in the range of about 70° C. to about 80° C. until a clear solution is formed.

Step 4: Add about 95.0% of the batch quantity of purified water to the solution of Step 3 and slowly add the batch quantity of HP.beta.CD thereto under continuous stirring until a clear solution is formed.

Step 5: Slowly add the batch quantities of sucralose, neotame, bitter blocker powder, and sodium chloride to the solution of Step 4 under continuous stirring until a clear solution is formed.

Step 6: Add the batch quantities of corn syrup and maltitol to the solution of Step 5 under continuous stirring while heating the mixture to a temperature above about 50° C. to form a homogenous mixture.

Step 7: Mix the batch quantities of carrageenan and trisodium citrate, and about 16.3% of the batch quantity of sucrose until a homogenous blend is formed.

Step 8: Add the blend of Step 7 to the mixture of Step 6 under continuous stirring while maintaining the temperature of the mixture above 75° C. until a homogenous gel is formed.

Step 9: Heat the gel of Step 8 to a temperature in the range of about 85° C. to about 100° C. until a thick gel mixture is observed.

Step 10: Add about 83.7% of the batch quantity of sucrose to the gel mixture of Step 9 and heat the mixture to a temperature in the range of about 95° C. to about 105° C.

Step 11: Maintain the temperature of the gel mixture formed in Step 10 in the range of about 95° C. to about 105° C. until the total solid content of the mixture raises to about eighty percent by weight (80% w/w) or about eighty brix (80 brix).

Step 12: Add about 5.0% of the batch quantity of purified water and the batch quantities of the flavor agent and the color agent to a container under stirring until a clear solution is formed.

Step 13: Add the solution of Step 12 to the gel mixture formed in Step 11 under stirring while maintaining the temperature of the mixture in the range of about 80° C. to about 90° C. until a gummy mixture is formed.

Step 14: Transfer the gummy mixture of Step 13 to a product mold. Allow the gummy mixture to cool at room temperature for about 10 to about 15 minutes and then remove the individual chewable gel units from the mold.

Step 15: Delump the batch quantity of pregelatinized starch using a #40 mesh to form a homogenous powder.

Step 16: Polish the chewable gel units of Step 14 with the powder of Step 15 for approximately 5 to about 10 minutes to form polished chewable gel units.

Step 17: Store the polished chewable gel units of Step 16 for curing at a temperature in the range of about 25° C. to about 35° C. for 3 to 5 days.

Step 18: Transfer the cured chewable gel units of Step 17 into suitable packaging.

Example 27

A process for making chewable gel units in accordance with certain aspects of the present invention is provided in Example 27 below. The ingredients corresponding to Example 27 are tabulated in Table 27 with the amount of each ingredient used in the process (i.e., the batch quantity) given in grams. In Example 27 the active ingredient is diphenhydramine HCl. Each chewable gel unit formed in accordance with Example 27 has an active strength of diphenhydramine HCl of about 25 mg. Each chewable gel unit formed by the process of Example 27 has a mass of about 3,600 mg. One hundred (100) chewable gel units are formed by the process of Example 27; however, as should be understood by those having ordinary skill in the art, the principles of Example 27 can be used to make more or less chewable gel units by proportionally increasing or decreasing the amount of ingredients as necessary to produce the desired quantity of chewable gel units.

TABLE 27

| Ingredient Name | Batch Quantity |
| --- | --- |
| Diphenhydramine HCl | 2.5 |
| Bitter blocker powder | 1.5 |
| Carrageenan | 10 |
| Citric acid anhydrous | 0.8 |
| Color agent (FD&C red #40) | 0.01 |
| Corn syrup (liquid glucose) | 160 |
| Ethanol | 7.5 |
| Flavor agent (tutti frutti flavor) | 0.7 |
| HP.beta.CD | 10 |

TABLE 27-continued

| Ingredient Name | Batch Quantity |
|---|---|
| Magnesium stearate | 1 |
| Maltitol solution | 32.49 |
| Neotame | 0.1 |
| Pregelatinized starch (starch 1500) | 7.2 |
| Purified water | 130 |
| Sodium chloride | 1.5 |
| Sucralose | 1.4 |
| Sucrose | 98.3 |
| Trisodium citrate | 1.5 |

Procedure—Example 27

Step 1: Add the batch quantities of ethanol and diphenhydramine HCl to a container under continuous stirring while heating the mixture to a temperature in the range of about 70° C. to about 80° C. until a clear solution is formed.

Step 2: Add about 6.2% of the batch quantity of purified water to the solution of Step 1 under continuous stirring while maintaining the temperature of the mixture in the range of about 70° C. to about 80° C. until a clear solution is formed.

Step 3: Add about 87.7% of the batch quantity of purified water to a container. Slowly add the batch quantity of HP.beta.CD to the purified water under continuous stirring until a clear solution is formed.

Step 4: Slowly add and dissolve the batch quantities of sucralose, neotame, bitter blocker powder, and sodium chloride in the solution of Step 3 under continuous stirring to form a clear solution.

Step 5: Add the batch quantity of corn syrup to the solution of Step 4 under continuous stirring while heating the mixture to a temperature above about 50° C. to form a homogenous mixture.

Step 6: Combine the solution of Step 2 and the mixture of Step 5 under continuous stirring while maintaining the temperature of the mixture above about 70° C. until a homogenous mixture is formed.

Step 7: Mix the batch quantities of carrageenan and trisodium citrate, and about 10.2% of the batch quantity of sucrose until a homogenous blend is formed.

Step 8: Add the blend of Step 7 to the mixture of Step 6 under continuous stirring while heating the mixture to a temperature above 75° C. until a homogenous gel is formed.

Step 9: Continue heating the gel of Step 8 to a temperature in the range of about 85° C. to about 100° C. until a thick gel mixture is observed.

Step 10: Add the batch quantity of maltitol solution and about 89.8% of the batch quantity of sucrose to the gel mixture of Step 9 while heating the mixture to a temperature in the range of about 95° C. to about 105° C.

Step 11: Maintain the temperature of the gel mixture of Step 10 in the range of about 95° C. to about 105° C. until the total solid content of the mixture raises to about 70% w/w or about 70 brix.

Step 12: Add about 6.1% of the batch quantity of purified water and the batch quantities of the flavor agent and the color agent to a container under stirring until a clear solution is formed.

Step 13: Add the solution of Step 12 to the gel mixture of Step 11 under stirring while maintaining a temperature of the mixture in the range of about 80° C. to about 90° C. to form a gummy mixture.

Step 14: Transfer the gummy mixture of Step 13 to a product mold. Allow the gummy mixture to cool at room temperature for about 10 to about 15 minutes and then remove the individual chewable gel units from the mold.

Step 15: Delump the batch quantities of pregelatinized starch, citric acid anhydrous, and magnesium stearate using a #40 mesh to form a homogenous blend.

Step 16: Polish the chewable gel units of Step 14 with the blend of Step 15 for approximately 5 to about 10 minutes to form polished chewable gel units.

Step 17: Store the polished chewable gel units of Step 16 for curing at a temperature in the range of about 25° C. to about 35° C. for 3 to 5 days.

Step 18: Transfer the chewable gel units of Step 17 into suitable packaging.

Example 28 ingredients corresponding to Example 28 are tabulated in Table 28, with the amount of each ingredient given in respective percent-by-weight (% w/w).

TABLE 28

| Ingredient Name | Quantity (% w/w) |
|---|---|
| Acetaminophen | 2.86 |
| FD&C Red 40 | 0.1 |
| HP.beta.CD | 8.54 |
| Glycerin | 4.11 |
| PEG 400 | 1.23 |
| Strawberry Flavor | 0.49 |
| Gelatin | 13.55 |
| Light Mineral Oil | 0.18 |
| Citric acid | 0.8 |
| Maltitol solution | 47.96 |
| PVA | 0.49 |
| PVP K30 | 0.49 |
| Dextrose | 1.04 |
| Sucralose | 0.56 |
| Purified Water | 17.58 |
| TOTAL | 100 |

Procedure—Example 28

STEP I: add about half the quantity of purified water into a container and heat to about sixty-five degrees Celsius (65° C.), then add and dissolve the quantities of acetaminophen and HP.beta.CD under stirring, until clear solution is observed.

STEP II: add the remaining quantity of purified water to a separate container and heat to about eighty-five degrees Celsius (85° C.), then add and dissolve the quantities of PVA and PVP K30 under stirring, until clear solution is observed.

STEP III: combine the mixtures from STEP II and STEP I under continuous stirring. Add and disperse the quantity of gelatin under continuous stirring for at least about ten (10) minutes, maintain temperature at about eighty-five degrees Celsius (85° C.).

STEP IV: add and mix the quantity of Lycasin 80-55 into contents of STEP III. Add and dissolve quantities of dextrose and sucralose with continuous stirring.

STEP V: combine and mix the batch quantities of glycerin, mineral oil, PEG 400, strawberry flavor, and FD&C Red 40 in a separate container.

STEP VI: combine the mixture of STEP V and the mixture of STEP IV. Add and dissolve the quantity of citric acid under continuous stirring until a homogenous solution obtained.

STEP VII: transfer the gummy mixture from STEP VI to a product mold, allow the gummy mixture to stand for about fifteen (15) to about forty-five (45) minutes before removing the gummy dosage forms from the mold.

Example 29 ingredients corresponding to Example 29 are tabulated in Table 29, with the amount of each ingredient given in respective percent-by-weight (% w/w).

TABLE 29

| Ingredient Name | Quantity (% w/w) |
|---|---|
| Diphenhydramine Hydrochloride | 0.52 |
| FD&C Red 40 | 0.1 |
| HP.beta.CD | 10 |
| Glycerin | 4.11 |
| PEG 400 | 1.23 |
| Strawberry Flavor | 0.49 |
| Gelatin | 12.5 |
| Mineral Oil | 0.18 |
| Citric acid | 0.8 |
| Maltitol solution | 49.98 |
| PVA | 0.49 |
| PVP K-30 | 0.49 |
| Dextrose | 1.04 |

TABLE 29-continued

| Ingredient Name | Quantity (% w/w) |
|---|---|
| Sucralose | 0.56 |
| Purified Water | 17.57 |
| TOTAL | 100 |

Procedure—Example 29

STEP I: add about half of the quantity of purified water to a container and heat to about sixty-five degrees Celsius (65° C.). Add the quantities of diphenhydramine hydrochloride and HP.beta.CD to the purified water under stirring until clear solution is observed.

STEP II: add the remaining batch quantity of purified water into a separate container and heat to about eighty-five degrees Celsius (85° C.). Add and disperse the batch quantities of PVA and PVP K-30 under stirring to until clear solution is observed.

STEP III: combine the contents of STEP II and STEP I under continuous stirring. Add and disperse the batch quantity of gelatin under continuous stirring for approximately ten (10) minutes, maintaining temperature at about eighty-five degrees Celsius (85° C.).

STEP IV: add and mix the batch quantity of maltitol solution into contents of STEP III. Add and dissolve the batch quantities of dextrose and sucralose with continuous stirring.

STEP V: combine and mix batch quantities of glycerin, mineral oil, PEG 400, strawberry flavor, and FD&C Red 40 in a separate container.

STEP VI: combine contents from STEP V and STEP IV. Add and dissolve the batch quantity of citric acid under continuous stirring until a homogenous solution obtained.

STEP VII: transfer the gummy mixture from STEP VI to a product mold, cool to room temperature, and remove the gummy from the mold after cooling for about thirty to forty-five (30-45) minutes.

Example 30 ingredients corresponding to Example 30 are tabulated in Table 30, with the batch quantity amount of each ingredient given grams (g).

TABLE 30

| Ingredient Name | Ingredient Type | Batch Quantity (g) |
|---|---|---|
| Diphenhydramine hydrochloride | active ingredient | 514.8 |
| Sodium chloride | tonicity modifying agent | 330 |
| Trisodium citrate | buffering agent | 264 |
| Bubble gum flavor | flavor | 33 |
| Carrageenan | gelling agent | 1650 |
| HP.beta.CD | complexing agent | 1273 |
| Maltitol solution | non-crystallizing polyol solution | 5544 |
| Bitter blocker powder | taste enhancing agent | 238 |
| Corn syrup | taste enhancing agent/filler | 26730 |
| Neotame | taste enhancing agent | 33 |
| Sucralose | taste enhancing agent | 330 |
| Sugar | taste enhancing agent/filler | 15840 |
| Purified water | water | 23100 |
| TOTAL | | 75880 |

Procedure—Example 30: a twelve and one-half milligram (12.5 mg) diphenhydramine hydrochloride translucent gummy pharmaceutical dosage form composition and procedure:

STEP I: add about two thousand grams (2000 g) of purified water to a container. Slowly add the batch quantity of HP.beta.CD to the purified water under continuous stirring for approximately thirty (30) minutes.

STEP II: add the batch quantity of diphenhydramine hydrochloride to the mixture of STEP I under continuous stirring, a clear solution should be observed after approximately fifteen (15) minutes.

STEP III: add about twenty thousand five hundred grams (20500 g) of purified water to a container. Slowly add the batch quantities of sodium chloride, bitter blocker powder, sucralose, and neotame under stirring for approximately fifteen (15) minutes until clear solution observed.

STEP IV: add the batch quantity of corn syrup to the solution of STEP III under stirring for approximately ten (10) minutes and heat to a temperature in the range of about fifty degrees Celsius (50° C.) to about fifty-five degrees Celsius (55° C.).

STEP V: create a dry mix blend by combining the batch quantity of carrageenan, the batch quantity of trisodium citrate, and about two thousand grams (2000 g) sugar and mix for approximately ten (10) minutes.

STEP VI: add the dry mix blend from STEP V to the heated mixture of STEP IV under stirring and heat the mixture a temperature in the range of about fifty degrees Celsius (50° C.) to about fifty-five degrees Celsius (55° C.) under constant stirring.

STEP VII: heat the gummy mixture from STEP VI to about ninety a temperature in the range of about ninety degrees Celsius (90° C.) to about one hundred five degrees Celsius (105° C.), add the batch quantity of maltitol solution and the remaining batch quantity of sugar, and continue heating the mixture to a temperature in the range of about ninety degrees Celsius (90° C.) to about one hundred five degrees Celsius (105° C.) for approximately ninety (90) minutes until the total solid content raises to about seventy-four percent-by-weight (74% w/w) or about seventy-four brix (74 Brix).

STEP VIII: combine the solution of STEP II and the mixture of STEP VII under stirring and maintain a temperature in the range of about ninety degrees Celsius (90° C.) to about one hundred five degrees Celsius (105° C.) until total solid content raises to about seventy-four percent-by-weight (74% w/w) or about seventy-four brix (74 Brix).

STEP IX: add and dissolve the batch quantity of bubble gum flavor to the remaining batch quantity of purified water to a container.

STEP X: combine the solution of STEP IX to mixture of STEP VIII under stirring and maintain a temperature in the range of about ninety-five degrees Celsius (95° C.) to about one hundred five degrees Celsius (105° C.).

STEP XI: transfer the gummy mixture from STEP X to a product mold, cool to room temperature, and remove the gummy from the mold after cooling for about ten (10) to about fifteen (15) minutes.

Example 31

Ingredients corresponding to Example 31 are tabulated in Table 31, with the batch quantity amount of each ingredient given grams (g).

TABLE 31

| Ingredient Name | Batch Quantity (g) |
| --- | --- |
| Diphenhydramine hydrochloride | 468 |
| Sodium chloride | 300 |
| Trisodium citrate | 240 |
| Pink color | 60 |
| Bubble gum flavor | 60 |
| Carrageenan | 1500 |
| Maltitol solution | 5040 |
| Bitter blocker | 216 |
| Corn syrup | 24300 |
| Neotame | 30 |
| Sucralose | 300 |

TABLE 31-continued

| Ingredient Name | Batch Quantity (g) |
| --- | --- |
| Sugar | 15220 |
| Purified water | 21000 |
| TOTAL | 68734 |

Procedure—Example 31: a twelve and one-half milligram (12.5 mg) diphenhydramine hydrochloride translucent chewable pharmaceutical dosage form composition and procedure:

STEP I: add nineteen thousand and five-hundred grams (19,500 g) of purified water to a container. Slowly add the batch quantities of sodium chloride, bitter blocker powder, sucralose, and neotame under stirring for approximately fifteen (15) minutes until clear solution observed.

STEP II: add the batch quantity corn syrup to the solution of STEP I under stirring for approximately ten (10) minutes and heat a temperature in the range of about fifty degrees Celsius (50° C.) to about fifty-five degrees Celsius (55° C.).

STEP III: prepare a dry mix blend by combining the batch quantity of carrageenan, the batch quantity of trisodium citrate, and two thousand grams (2000 g) of sugar and mix for approximately ten (10) minutes.

STEP IV: add the dry mix blend from STEP III to the heated solution of STEP II under stirring.

STEP V: heat the gummy mixture from STEP IV, while stirring to a temperature in the range of about ninety degrees Celsius (90° C.) to about one hundred five degrees Celsius (105° C.).

STEP VI: add the batch quantity of maltitol solution and fifteen thousand two hundred twenty (15,220 g) of sugar to the gummy mixture of STEP V under stirring; and continue heating the gummy mixture to a temperature in the range of about ninety degrees Celsius (90° C.) to about one hundred five degrees Celsius (105° C.) until total solid content raises to about seventy-four percent-by-weight (74% w/w) or about seventy-four brix (74 Brix).

STEP VII: in a container, add and dissolve the batch quantities of diphenhydramine hydrochloride, bubble gum flavor, and pink color in about one thousand five hundred (1500 grams) of purified water.

STEP VIII: combine the mixtures of STEP VI to mixture of STEP VII under stirring and maintain a temperature in the range of about ninety-five degrees Celsius (95° C.) to about one hundred five degrees Celsius (105° C.).

STEP IX: transfer the gummy mixture from STEP VIII to a product mold, cool to room temperature, and remove the gummy from the mold after cooling for about for about ten (10) to about fifteen (15) minutes.

Example 32 ingredients corresponding to Example 32 are tabulated in Table 32, with the amount of each ingredient given in respective percent-by-weight (% w/w).

TABLE 32

| Ingredient Name | Batch Quantity (g) |
| --- | --- |
| Acetaminophen | 15.00 |
| Sodium chloride | 1.50 |
| Trisodium citrate | 1.20 |

TABLE 32-continued

| Ingredient Name | Batch Quantity (g) |
|---|---|
| FD&C Yellow | 0.30 |
| HP.beta.CD | 37.50 |
| Pineapple flavor | 1.50 |
| Carrageenan | 7.50 |
| Maltitol solution | 12.87 |
| Bitter blocker | 1.08 |
| Corn syrup | 121.50 |
| Neotame | 0.15 |
| Sucralose | 1.50 |
| Sugar | 38.17 |
| Purified water | 105.00 |
| TOTAL | 344.77 |

Procedure—Example 32

STEP I: add purified water to a container; add the batch quantities of HP.beta.CD and acetaminophen under stirring for approximately fifteen (15) minutes.

STEP II: heat the mixture from STEP I to a temperature in the range of about fifty degrees Celsius (50° C.) to about fifty-five degrees Celsius (55° C.) while stirring; clear solution observed after approximately fifteen (15) minutes;

STEP III: add purified water to a container; add the batch quantities of sodium chloride, sucralose, neotame, and bitter blocker under stirring; clear solution observed after approximately fifteen (15) minutes;

STEP IV: add the batch quantity of corn syrup to the solution of STEP III under stirring; a temperature in the range of about fifty degrees Celsius (50° C.) to about fifty-five degrees Celsius (55° C.) while stirring; clear solution observed.

STEP V: prepare a dry mix blend by combining the batch quantity of carrageenan, the batch quantity of trisodium citrate, and 10 grams (10 g) of sugar and mix for approximately ten (10) minutes.

STEP VI: add the dry mix blend from STEP V to the heated solution of STEP IV under constant stirring for approximately twenty (20) minutes;

STEP VII: heat the gummy mixture from STEP VI to a temperature in the range of about ninety degrees Celsius (90° C.) to about ninety-five degrees Celsius (95° C.); add the batch quantity of maltitol solution and the remaining batch quantity of sugar; heat the gummy mixture to and maintain a temperature in the range of about one hundred degrees Celsius (100° C.) to about one hundred five degrees Celsius (105° C.) for approximately ninety (90) minutes until the total solid content raises to seventy-four percent (74% w/w) or about seventy-four brix (74 Brix)

STEP VIII: combine the solution of STEP I and the gummy mixture of STEP VII under stirring; maintain a temperature in the range of about ninety-five degrees Celsius (95° C.) to about one hundred five degrees Celsius (105° C.) until the total solid content is about seventy-four percent-by-weight (74% w/w) or about seventy-four brix (74 Brix).

STEP IX: transfer the gummy mixture from STEP VIII to a product mold, cool to room temperature, and remove the gummy from the mold after cooling for about fifteen (15) to twenty (20) minutes.

The chewable gel units were subjected to several quantitative and qualitative tests. The tests and the findings thereof are discussed and summarized in the paragraphs and tables below. For purposes of Tables D1-D42, the following table headings are to be interpreted as follows: "Ex #" means the Example number whereby the texted chewable gel was formed; "SD" means the duration of time, provided in number of days, that the chewable gel(s) was stored, relative to the curing step provided in the corresponding Example, prior to testing; "ST" means the temperature, provided in degrees Celsius, at which the chewable gel(s) was stored; and "SRH" means the relative humidity, provided in percentage, in which the chewable gel(s) was stored. Other heading definitions are provided where necessary.

The results of a product characterization analysis performed on the chewable gel units formed in accordance with the Examples provided herein are summarized in Tables D1-D7. Table D1 provides information pertaining to the product characterization analysis of the chewable gel units formed in accordance with the corresponding Examples provided therein shortly after the curing step. In each instance, the chewable gels referenced in Table D1 were translucent.

TABLE D1

| Ex # | Shape | Dimensions (mm) | Color |
|---|---|---|---|
| 2 | Bear | 20 × 12 × 7 (L × W × H) | Light yellow/brown |
| 4 | Rectangular | 18 × 11 × 9.2 (L × W × H) | Light yellow/brown |
| 6 | Bear | 20 × 12 × 7 | Light red |
| 6 | Rectangular | 18 × 11 × 9.2 | Light yellow/brown |
| 7 | Rectangular | 18 × 11 × 9.2 | Light yellow/brown |
| 9 | Cylindrical | 16 × 12.3 (L × W) | Light yellow/brown |
| 10 | Cylindrical | 16 × 12.3 | Light yellow/brown |
| 11 | Bear | 20 × 12 × 7 | Light yellow/brown |
| 12 | Bear | 20 × 12 × 7 | Light yellow/brown |
| 13 | Cylindrical | 16 × 12.3 | Orange |
| 14 | Cylindrical | 16 × 12.3 | Light yellow/brown |
| 15 | Rectangular | 20 × 10 × 13 | Light yellow/brown |
| 16 | Cylindrical | 16.62 × 16.04 | Orange |
| 18 | Rectangular | 20 × 10 × 12 | Light red |
| 19 | Rectangular | 20 × 10 × 14 | Orange |
| 20 | Rectangular | 18 × 10 × 10 | Light yellow/green |
| 21 | Rectangular | 20 × 10 × 15 | Light yellow/green |
| 22 | Rectangular | 20 × 10 × 12 | Light red |
| 23 | Rectangular | 20 × 10 × 13 | Light yellow/green |
| 24 | Rectangular | 20 × 10 × 15 | Orange |
| 25 | Rectangular | 20 × 10 × 15 | Light yellow/green |
| 26 | Rectangular | 20 × 10 × 15 | Orange |
| 27 | Rectangular | 20 × 10 × 12 | Light red |

Table D2 provides information pertaining to the product characterization analysis of the chewable gel units formed in accordance with the corresponding Examples provided therein after being stored for thirty (30) days at a temperature of forty degrees Celsius (40° C.) and seventy-five percent (75%). In each instance, the chewable gels referenced in Table D2 were translucent.

TABLE D2

| Ex # | Shape | Dimensions (mm) | Color |
|---|---|---|---|
| 4 | Rectangular | 18 × 11 × 9.2 (L × W × H) | Light yellow/brown |
| 7 | Rectangular | 18 × 11 × 9.2 | Light yellow/brown |
| 9 | Cylindrical | 16 × 12.3 (L × W) | Light yellow/brown |
| 10 | Cylindrical | 16 × 12.3 | Light yellow/brown |
| 13 | Cylindrical | 16 × 12.3 | Orange |
| 14 | Cylindrical | 16 × 12.3 | Light yellow/brown |
| 16 | Cylindrical | 16.60 × 16.02 | Orange |

TABLE D2-continued

| Ex # | Shape | Dimensions (mm) | Color |
|---|---|---|---|
| 18 | Rectangular | 20 × 10 × 12 | Light red |
| 19 | Rectangular | 20 × 10 × 14 | Orange |

Table D3 provides information pertaining to the product characterization analysis of the chewable gel units formed in accordance with the corresponding Examples provided therein after being stored for thirty (30) days at a temperature of 25° C. and a relative humidity of 60%. In each instance, the chewable gels referenced in Table D3 were translucent.

TABLE D3

| Ex # | Shape | Dimensions (mm) | Color |
|---|---|---|---|
| 4 | Rectangular | 18 × 11 × 9.2 (L × W × H) | Light yellow/brown |
| 7 | Rectangular | 18 × 11 × 9.2 | Light yellow/brown |
| 13 | Cylindrical | 16 × 12.3 (L × W) | Orange |

Table D4 provides information pertaining to the product characterization analysis of the chewable gel units formed in accordance with the corresponding Examples provided therein after being stored for ninety (90) days at a temperature of 40° C. and a relative humidity of 75%. In each instance, the chewable gels referenced in Table D4 were translucent.

TABLE D4

| Ex # | Shape | Dimensions (mm) | Color |
|---|---|---|---|
| 4 | Rectangular | 18 × 11 × 9.2 (L × W × H) | Light yellow/brown |
| 7 | Rectangular | 18 × 11 × 9.2 | Light yellow/brown |
| 9 | Cylindrical | 16 × 12.3 (L × W) | Light yellow/brown |
| 10 | Cylindrical | 16 × 12.3 | Light yellow/brown |
| 13 | Cylindrical | 16 × 12.3 | Orange |
| 14 | Cylindrical | 16 × 12.3 | Light yellow/brown |
| 16 | Cylindrical | 16.61 × 16.04 | Orange |
| 18 | Rectangular | 20 × 10 × 12 | Light red |
| 19 | Rectangular | 20 × 10 × 14 | Orange |

Table D5 provides information pertaining to the product characterization analysis of the chewable gel units formed in accordance with the corresponding Examples provided therein after being stored for ninety (90) days at a temperature of 25° C. and a relative humidity of 60%. In each instance, the chewable gels referenced in Table D5 were translucent.

TABLE D5

| Ex # | Shape | Dimensions (mm) | Color |
|---|---|---|---|
| 4 | Rectangular | 18 × 11 × 9.2 (L × W × H) | Light yellow/brown |
| 7 | Rectangular | 18 × 11 × 9.2 | Light yellow/brown |
| 9 | Cylindrical | 16 × 12.3 (L × W) | Light yellow/brown |
| 10 | Cylindrical | 16 × 12.3 | Light yellow/brown |
| 13 | Cylindrical | 16 × 12.3 | Orange |
| 14 | Cylindrical | 16 × 12.3 | Light yellow/brown |
| 16 | Cylindrical | 16.60 × 16.02 | Orange |
| 18 | Rectangular | 20 × 10 × 12 | Light red |
| 19 | Rectangular | 20 × 10 × 14 | Orange |

Table D6 provides information pertaining to the product characterization analysis of the chewable gel units formed in accordance with the corresponding Examples provided therein after being stored for one hundred eighty (180) days at a temperature of 40° C. and a relative humidity of 75%. In each instance, the chewable gels referenced in Table D6 were translucent.

TABLE D6

| Ex # | Shape | Dimensions (mm) | Color |
|---|---|---|---|
| 7 | Rectangular | 18 × 11 × 9.2 (L × W × H) | Light yellow/brown |
| 9 | Cylindrical | 16 × 12.3 (L × W) | Light yellow/brown |
| 10 | Cylindrical | 16 × 12.3 | Light yellow/brown |
| 13 | Cylindrical | 16 × 12.3 | Orange |
| 14 | Cylindrical | 16 × 12.3 | Light yellow/brown |
| 16 | Cylindrical | 16.60 × 16.02 | Orange |

Table D7 provides information pertaining to the product characterization analysis of the chewable gel units formed in accordance with the corresponding Examples provided therein after being stored for one hundred eighty (180) days at a temperature of 25° C. and a relative humidity of 60%. In each instance, the chewable gels referenced in Table D7 were translucent.

TABLE D7

| Ex # | Shape | Dimensions (mm) | Color |
|---|---|---|---|
| 7 | Rectangular | 18 × 11 × 9.2 (L × W × H) | Light yellow/brown |
| 9 | Cylindrical | 16 × 12.3 (L × W) | Light yellow/brown |
| 10 | Cylindrical | 16 × 12.3 | Light yellow/brown |
| 13 | Cylindrical | 16 × 12.3 | Orange |
| 14 | Cylindrical | 16 × 12.3 | Light yellow/brown |
| 16 | Cylindrical | 16.65 × 16.05 | Orange |
| 16 | Cylindrical | 16.60 × 16.00 | Orange |

A texture analysis was performed using a CT3 Texture Analyzer (Brookfield Engineering) configured as provided in Table D8. Texture parameters derived from the texture analysis are provided in Tables D9-D14, including values for: average hardness cycle 1 ("AHC1") given in grams; average adhesiveness ("AAd") given in millijoules; average fracturability with 1% load sensitivity ("AF1") given in grams; average hardness cycle 2 ("AHC2") given in grams; average cohesiveness ("ACo") given in millimeters; average springiness ("ASp") given in millimeters; average gumminess ("AGu") given in grams; and average chewiness ("ACh") given in millijoules. Additional details relating to the foregoing parameters and texture analyzer can be found in the Operating Instructions for the CT3 Texture Analyzer (Manual No. M08-372-F1116), which is incorporated herein by reference in its entirety. It should be understood that the present invention is not limited to parameters measured by a specific instrument and that other instruments may be used without departing from the spirit of the present invention.

TABLE D8

| Target | 6.0 mm |
|---|---|
| Hold time | 0 sec |
| Trigger load | 2 g |
| Test Speed | 2.00 mm/sec |
| Return speed | 2.0 mm/s |
| Number of cycles | 2 |
| Target Type | Distance |
| Recovery | 0 seconds |
| Same Trigger | TRUE |
| Pretest speed | 2.00 mm/sec |
| Data rate | 20.00 points/sec |
| Probe | TA 9 |
| Fixture | TA-STF |
| Load Cell | 25000 g |

Table D9 provides information pertaining to the dissolution analysis of the chewable gel units formed in accordance with the corresponding Examples provided therein shortly after the curing step. Table D9 includes values for: average hardness cycle 1 ("AHC1") given in grams; average adhesiveness ("AAd") given in millijoules; average fracturability with 1% load sensitivity ("AF1") given in grams; and average hardness cycle 2 ("AHC2") given in grams.

TABLE D9

| Ex # | AHC1 | AAd | AF1 | AHC2 |
|---|---|---|---|---|
| 4 | 170 | 0.2 | 4 | 154 |
| 6 | 170 | 0.2 | 4 | 154 |
| 9 | 224 | 0.3 | 26 | 198 |
| 13 | 24.8 | 0.18 | 12 | 17.6 |
| 16 | 88 | 0.17 | 8 | 88 |
| 18 | 170.67 | 0.43 | 13.33 | 130.67 |
| 21 | 91.33 | 0.13 | 5.33 | 79.33 |
| 22 | 131.33 | 0.17 | 8.67 | 98.67 |
| 23 | 144.67 | 0.23 | 13.33 | 109.33 |
| 24 | 156 | 0.1 | 14 | 131.33 |
| 25 | 175.33 | 0.1 | 9.33 | 152.67 |
| 26 | 88 | 0.17 | 8 | 88 |
| 26 | 148.67 | 0.23 | 8 | 122 |
| 26 | 85.33 | 0.13 | 4.67 | 75.33 |
| 27 | 142 | 0.13 | 11.33 | 112 |

Table D10 provides information pertaining to the dissolution analysis of the chewable gel units formed in accordance with the corresponding Examples provided therein after being stored for a number of days at a temperature of 40° C. and a relative humidity of 75%. Table D10 includes values for: average hardness cycle 1 ("AHC1") given in grams; average adhesiveness ("AAd") given in millijoules; average fracturability with 1% load sensitivity ("AF1") given in grams; and average hardness cycle 2 ("AHC2") given in grams.

TABLE D10

| Ex # | SD | AHC1 | AAd | AF1 | AHC2 |
|---|---|---|---|---|---|
| 4 | 30 | 128 | 0.1 | 12 | 116 |
| 7 | 30 | 134 | 0.3 | 2 | 122 |
| 7 | 90 | 150 | 0.2 | 10 | 130 |
| 9 | 30 | 214 | 0.1 | 30 | 194 |
| 16 | 180 | 148.67 | 0.23 | 8 | 122 |

Table D11 provides information pertaining to the dissolution analysis of the chewable gel units formed in accordance with the corresponding Examples provided therein after being stored for a number of days at a temperature of 25° C. and a relative humidity of 60%. Table D11 includes values for: average hardness cycle 1 ("AHC1") given in grams; average adhesiveness ("AAd") given in millijoules; average fracturability with 1% load sensitivity ("AF1") given in grams; and average hardness cycle 2 ("AHC2") given in grams.

TABLE D11

| Ex # | SD | AHC1 | AAd | AF1 | AHC2 |
|---|---|---|---|---|---|
| 4 | 30 | 142 | 0.2 | 10 | 108 |
| 7 | 30 | 414 | 1.5 | 414 | 322 |
| 16 | 180 | 85.33 | 0.13 | 4.67 | 75.33 |

Table D12 provides information pertaining to the dissolution analysis of the chewable gel units formed in accordance with the corresponding Examples provided therein shortly after the curing step. Table D12 includes values for: average cohesiveness ("ACo") given in millimeters; average springiness ("ASp") given in millimeters; average gumminess ("AGu") given in grams; and average chewiness ("ACh") given in millijoules.

TABLE D12

| Ex # | ACo | ASp | AGu | ACh |
|---|---|---|---|---|
| 4 | 0.58 | 4.47 | 98 | 4.3 |
| 6 | 0.58 | 4.47 | 98 | 4.3 |
| 9 | 0.71 | 5.28 | 159 | 8.2 |
| 13 | 0.39 | 4.91 | 9.8 | 0.48 |
| 16 | 0.7 | 4.35 | 61.33 | 2.6 |
| 18 | 0.47 | 5.01 | 80.33 | 3.97 |
| 21 | 0.49 | 3.81 | 44.33 | 1.67 |
| 22 | 0.32 | 3.59 | 42.67 | 1.5 |
| 23 | 0.29 | 3.55 | 33.33 | 1.47 |
| 24 | 0.49 | 4.63 | 76 | 3.47 |
| 25 | 0.54 | 4.76 | 94.67 | 4.47 |
| 26 | 0.7 | 4.35 | 61.33 | 2.6 |
| 26 | 0.45 | 4.29 | 67 | 2.93 |
| 26 | 0.61 | 5.49 | 51.67 | 2.77 |
| 27 | 0.42 | 4.83 | 59.67 | 2.8 |

Table D13 provides information pertaining to the dissolution analysis of the chewable gel units formed in accordance with the corresponding Examples provided therein after being stored for a number of days at a temperature of 25° C. and a relative humidity of 60%. Table D13 includes values for: average cohesiveness ("ACo") given in millimeters; average springiness ("ASp") given in millimeters; average gumminess ("AGu") given in grams; and average chewiness ("ACh") given in millijoules.

TABLE D13

| Ex # | SD | ACo | ASp | AGu | ACh |
|---|---|---|---|---|---|
| 4 | 30 | 0.46 | 4.85 | 65 | 3.1 |
| 7 | 30 | 0.51 | 6.39 | 210 | 13.1 |
| 16 | 180 | 0.61 | 5.49 | 51.67 | 2.77 |

Table D14 provides information pertaining to the dissolution analysis of the chewable gel units formed in accordance with the corresponding Examples provided therein after being stored for a number of days at a temperature of 40° C. and a relative humidity of 75%. Table D14 includes values for: average cohesiveness ("ACo") given in millimeters; average springiness ("ASp") given in millimeters; average gumminess ("AGu") given in grams; and average chewiness ("ACh") given in millijoules.

TABLE D14

| Ex # | SD | ACo | ASp | AGu | ACh |
|---|---|---|---|---|---|
| 4 | 30 | 0.66 | 5.24 | 85 | 4.4 |
| 7 | 30 | 0.65 | 4.12 | 86 | 3.5 |
| 7 | 90 | 0.46 | 4.6 | 70 | 3.1 |
| 9 | 30 | 0.65 | 6.69 | 140 | 9.2 |
| 16 | 180 | 0.45 | 4.29 | 67 | 2.93 |

Figure 1:
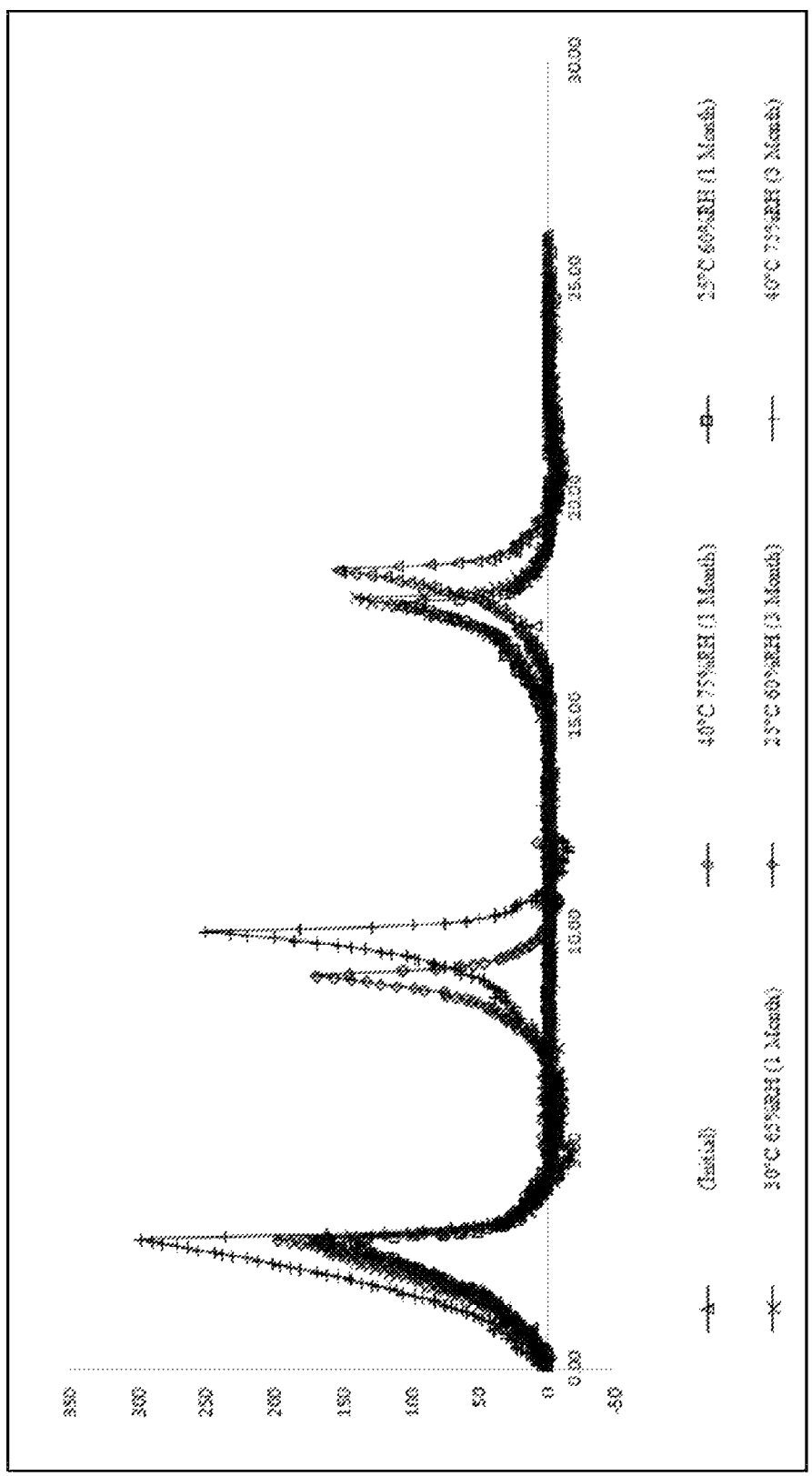
FIG. 1 is a chart showing the texture profiles (load in grams vs. time in seconds) for the chewable gel units formed in accordance with Example 4.

FIG. 1 illustrates texture analysis load peaks registered at 3-different points and performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 4 after being stored for various durations and under various conditions as indicated in the chart legend.

Figure 2:
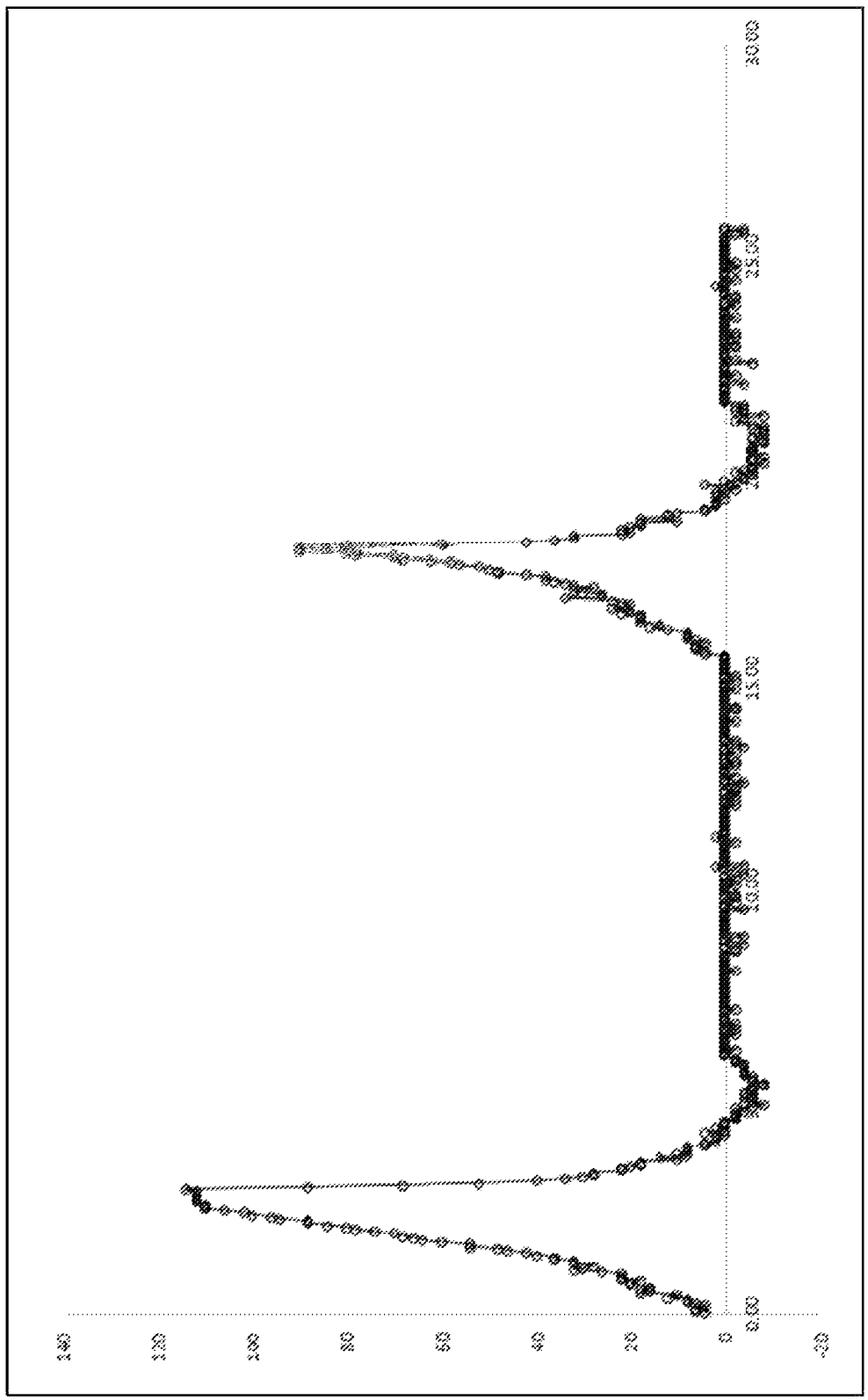
FIG. 2 is a chart showing the texture profiles (load in grams vs. time in seconds) for the chewable gel units formed in accordance with Example 6.

FIG. 2 illustrates texture analysis load peaks registered at approximately around 3-seconds and 18-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 6 and stored for 0-days relative to the curing step.

Figure 3:
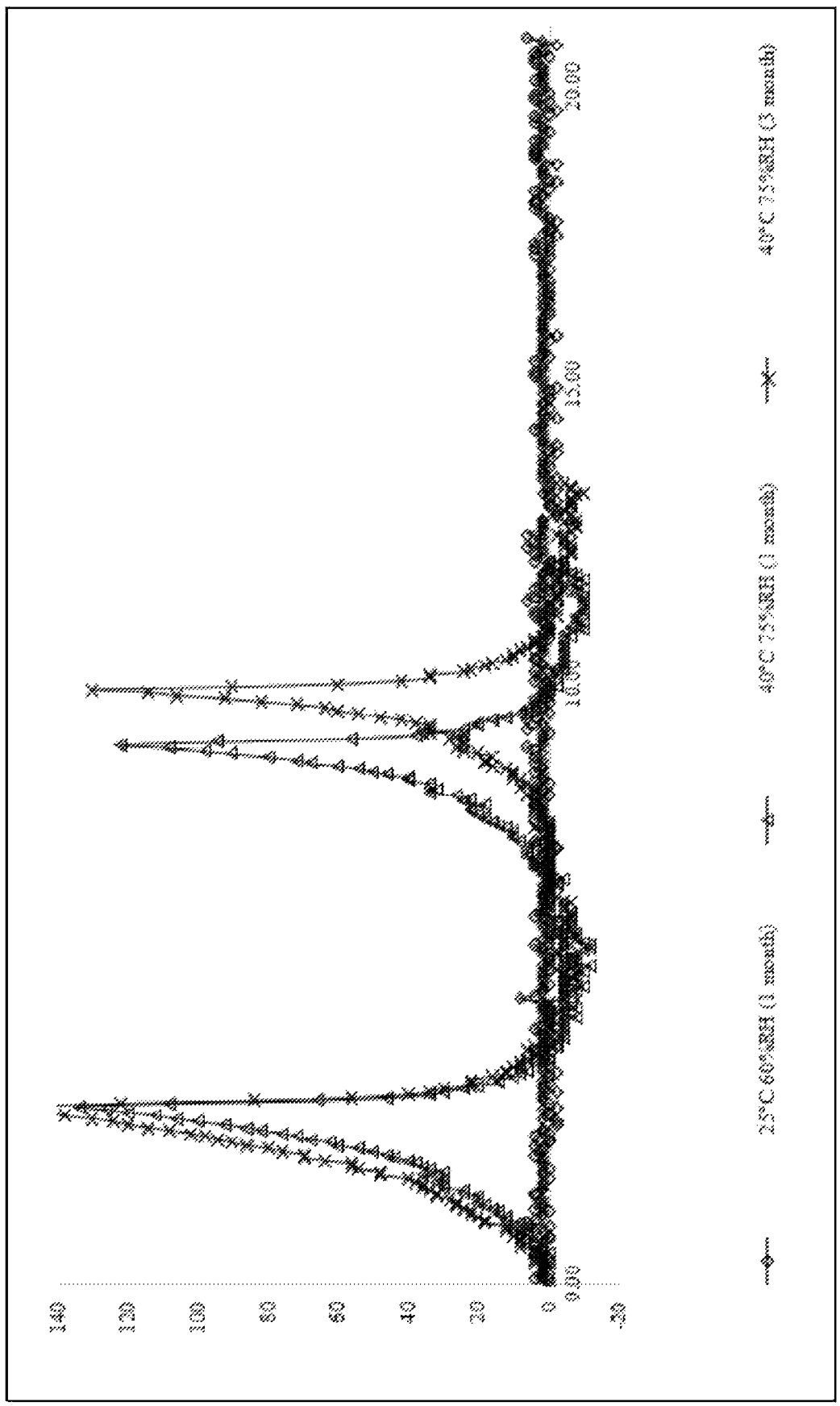
FIG. 3 is a chart showing the texture profiles (load in grams vs. time in seconds) for the chewable gel units formed in accordance with Example 7.

FIG. 3 illustrates texture analysis load peaks registered at 2-different points and performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 7 after being stored for various durations and under various conditions as indicated in the chart legend.

Figure 4:
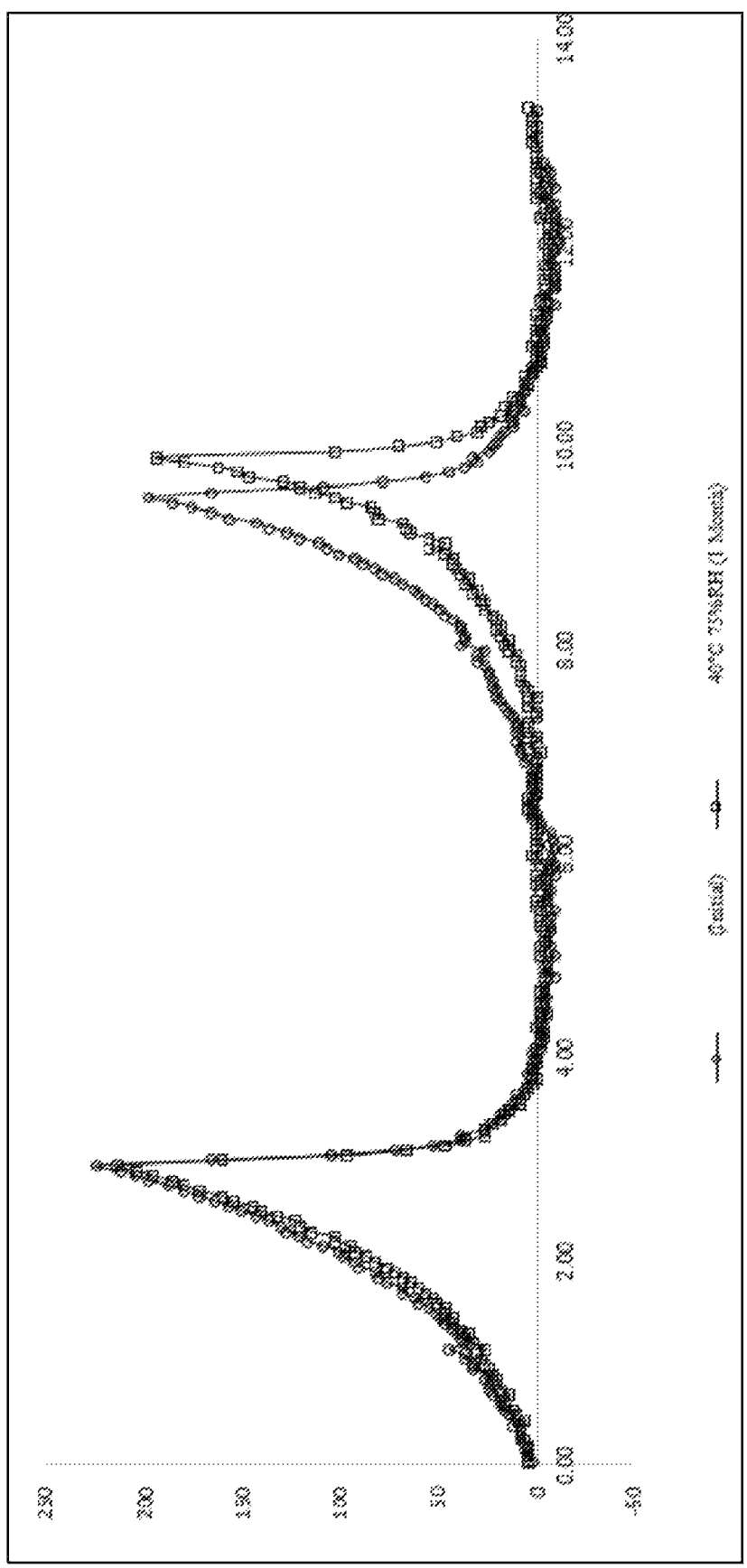
FIG. 4 is a chart showing the texture profiles (load in grams vs. time in seconds) for the chewable gel units formed in accordance with Example 9.

FIG. 4 illustrates texture analysis load peaks registered at 2-different points and performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 9 after being stored for various durations and under various conditions as indicated in the chart legend.

Figure 5:
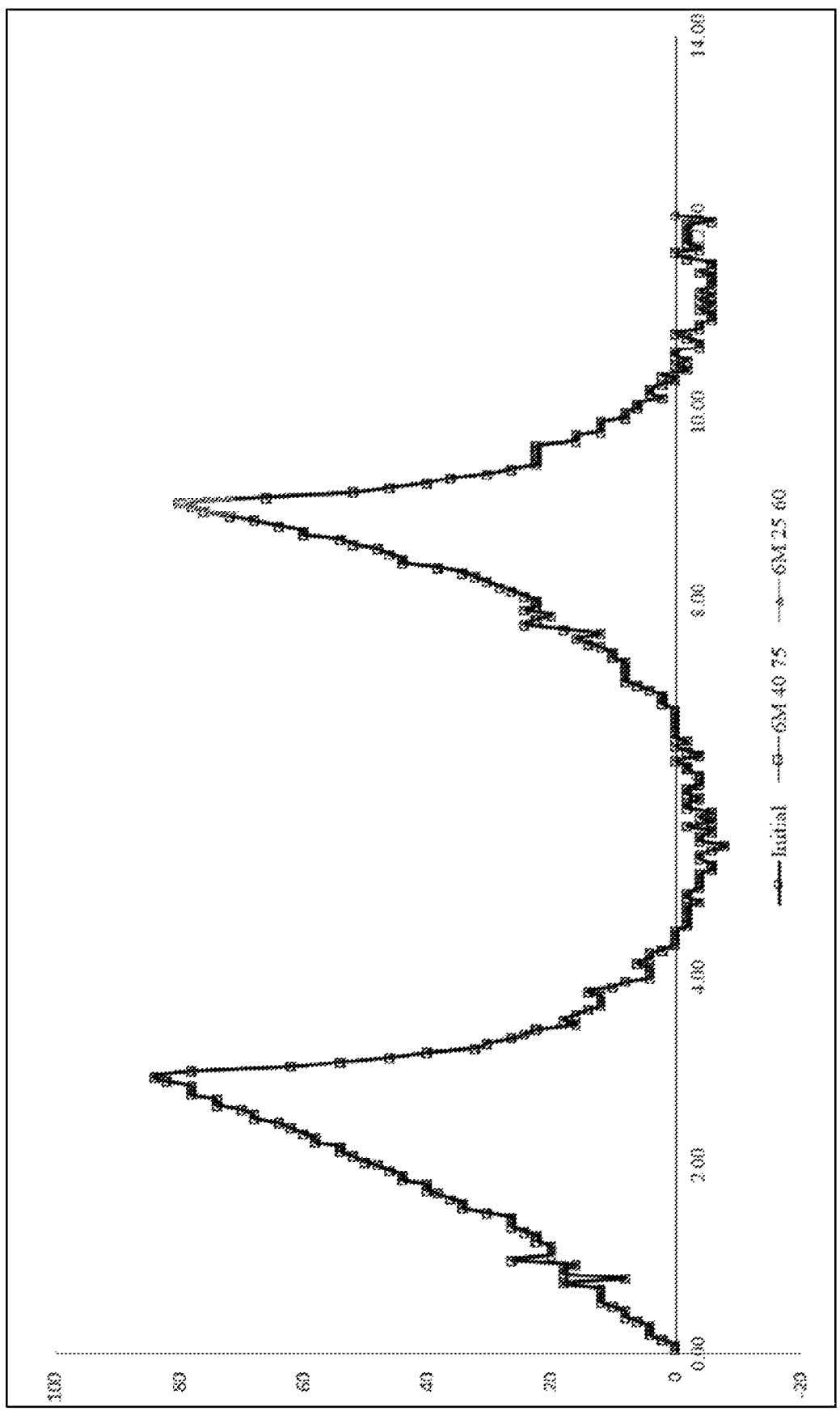
FIG. 5 is a chart showing the texture profiles (load in grams vs. time in seconds) for the chewable gel units formed in accordance with Example 16.

FIG. 5 illustrates texture analysis load peaks registered at 2-different points and performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 16 after being stored for various durations and under various conditions as indicated in the chart legend.

Figure 6:
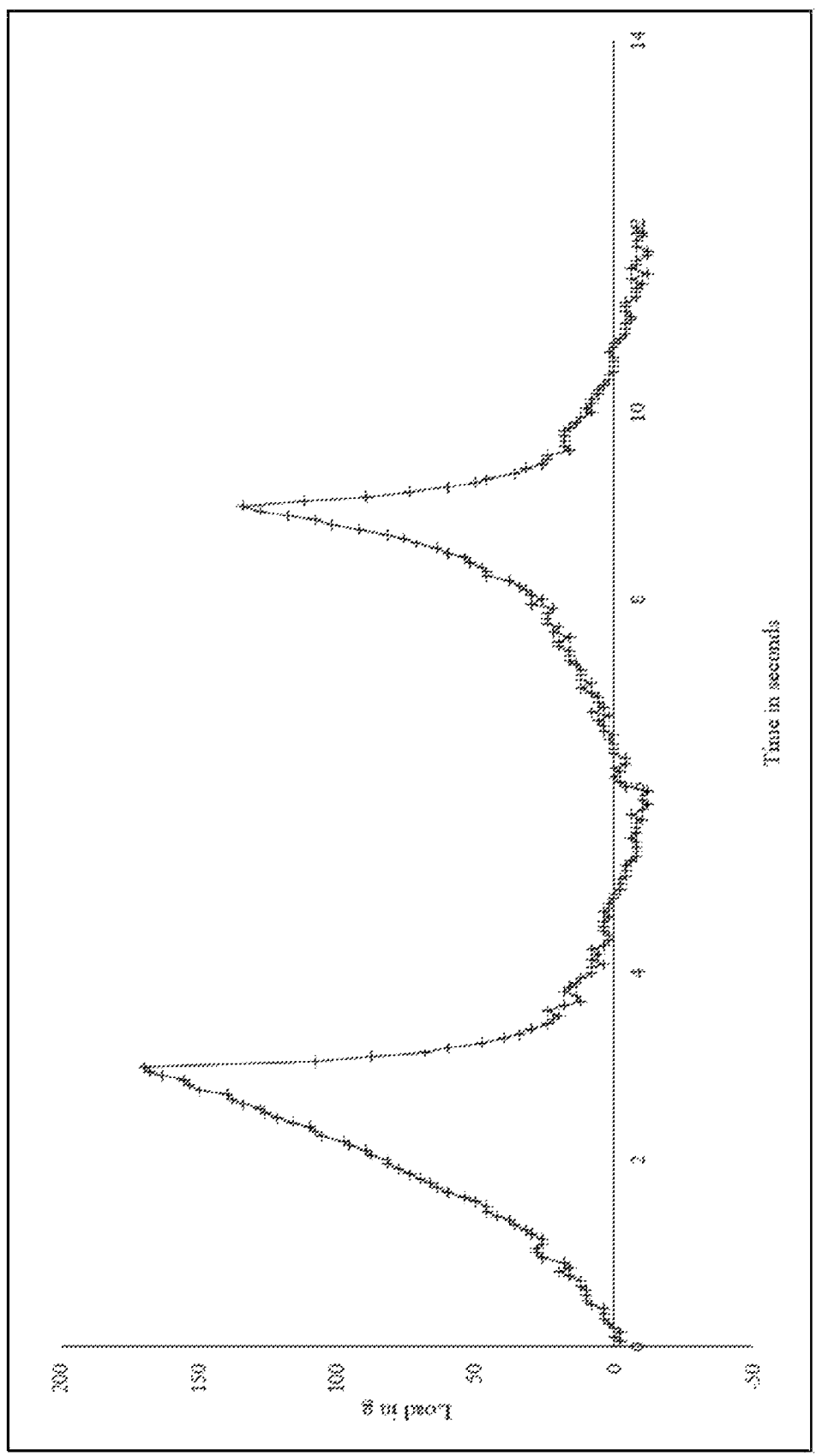
FIG. 6 is a chart showing the texture profiles (load in grams vs. time in seconds) for the chewable gel units formed in accordance with Example 18.

FIG. 6 illustrates texture analysis load peaks registered at approximately 3-seconds and 9-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 18 and stored for 0-days relative to the curing step.

Figure 7:
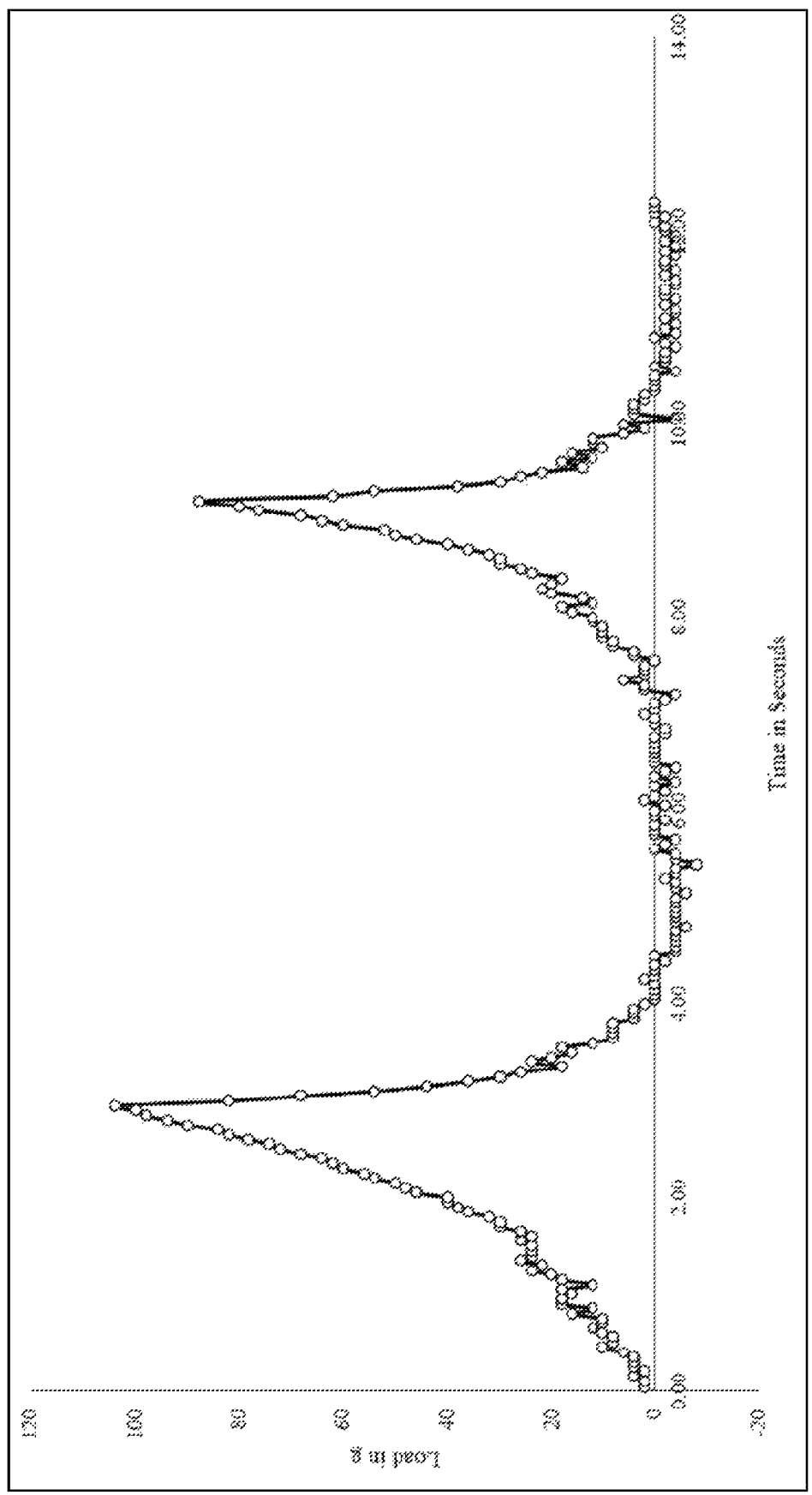
FIG. 7 is a chart showing the texture profiles (load in grams vs. time in seconds) for the chewable gel units formed in accordance with Example 21.

FIG. 7 illustrates texture analysis load peaks registered at approximately 3-seconds and 9-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 21 and stored for 0-days relative to the curing step.

Figure 8:
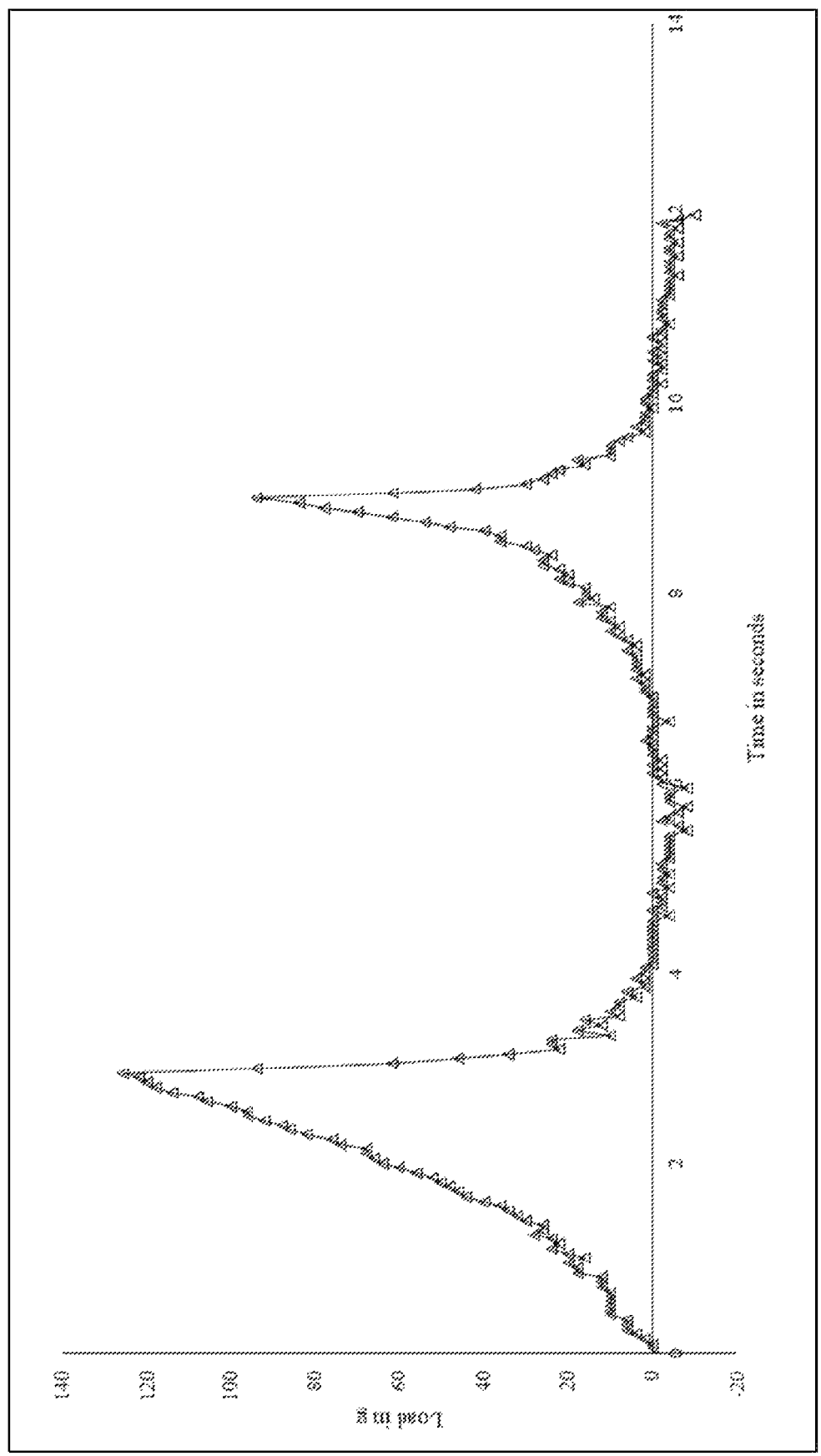
FIG. 8 is a chart showing the texture profiles (load in grams vs. time in seconds) for the chewable gel units formed in accordance with Example 22.

FIG. 8 illustrates texture analysis load peaks registered at approximately 3-seconds and 9-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 22 and stored for 0-days relative to the curing step.

Figure 9:
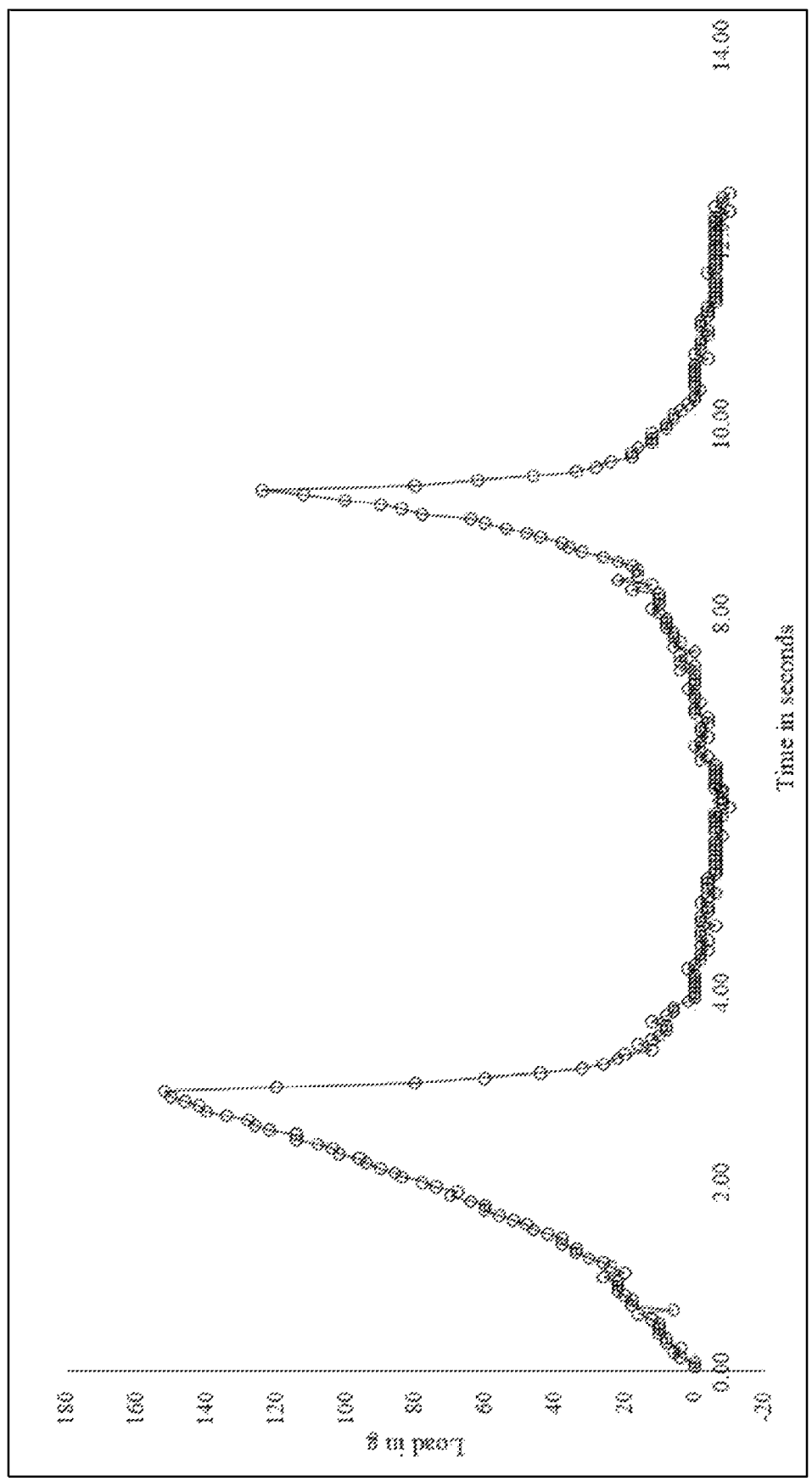
FIG. 9 is a chart showing the texture profiles (load in grams vs. time in seconds) for the chewable gel units formed in accordance with Example 23.

FIG. 9 illustrates texture analysis load peaks registered at approximately 3-seconds and 9-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 23 and stored for 0-days relative to the curing step.

Figure 10:
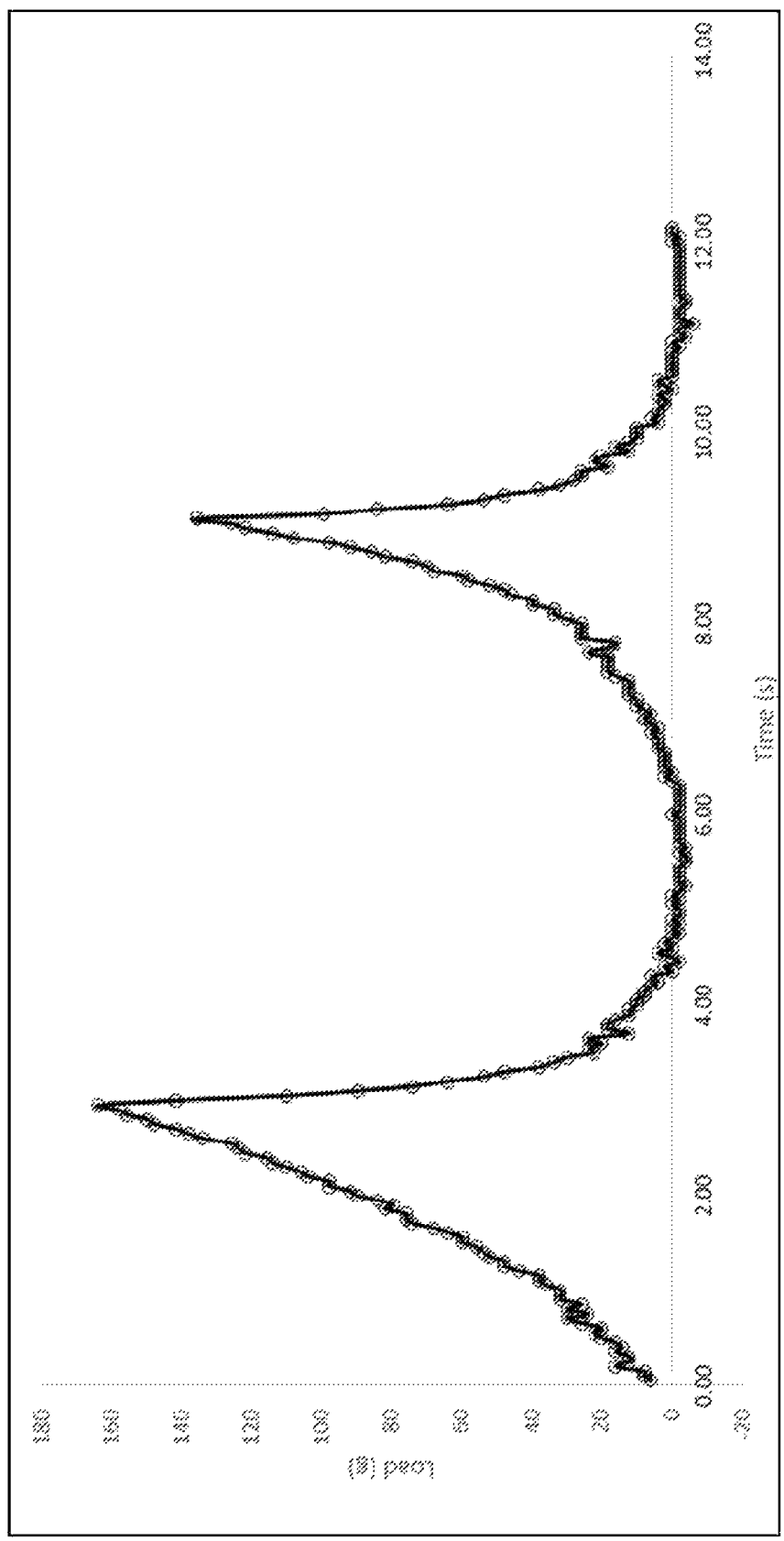
FIG. 10 is a chart showing the texture profiles (load in grams vs. time in seconds) for the chewable gel units formed in accordance with Example 24.

FIG. 10 illustrates texture analysis load peaks registered at approximately 3-seconds and 9-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 24 and stored for 0-days relative to the curing step.

Figure 11:
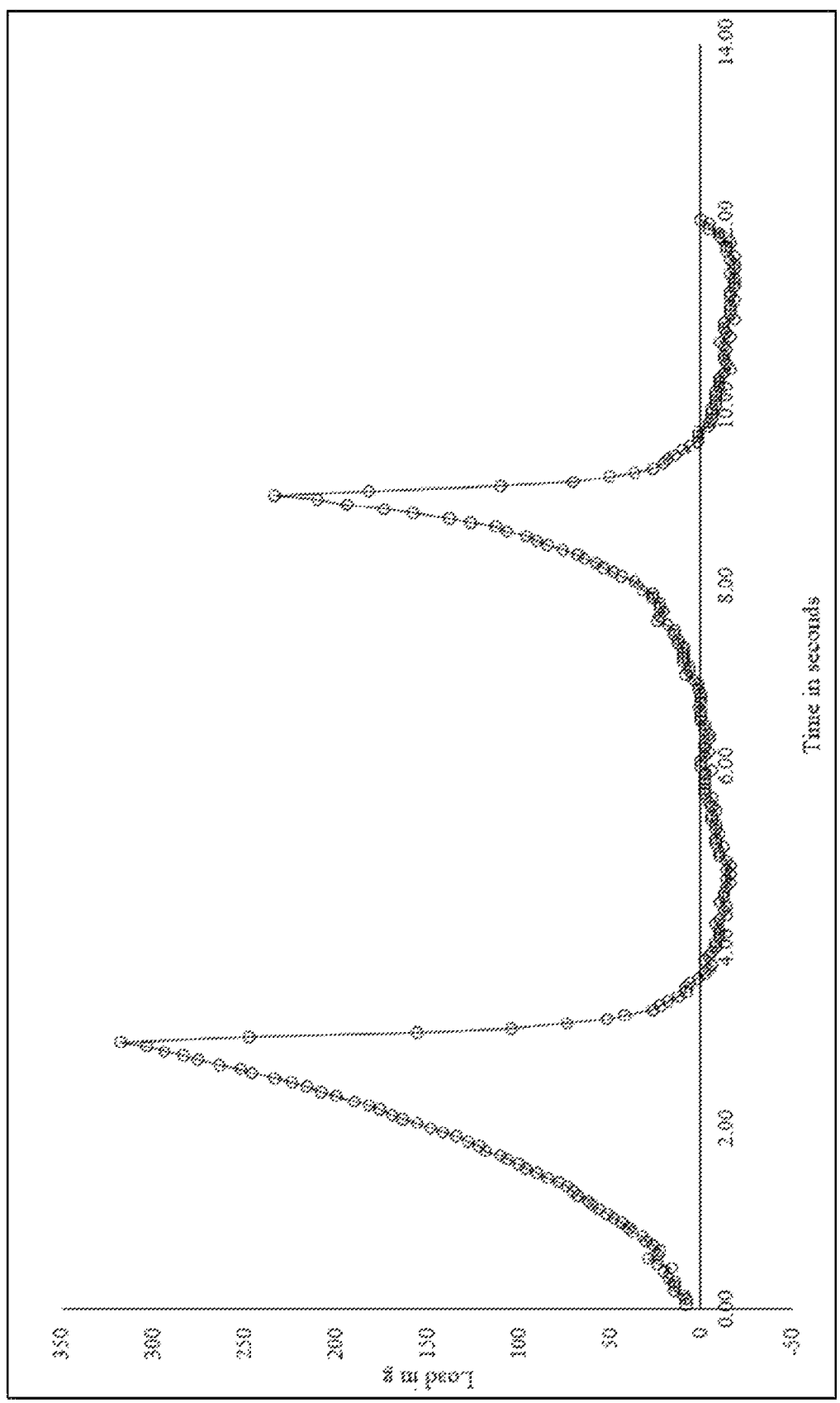
FIG. 11 is a chart showing the texture profiles (load in grams vs. time in seconds) for the chewable gel units formed in accordance with Example 25.

FIG. 11 illustrates texture analysis load peaks registered at approximately 3-seconds and 9-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 25 and stored for 0-days relative to the curing step.

Figure 12:
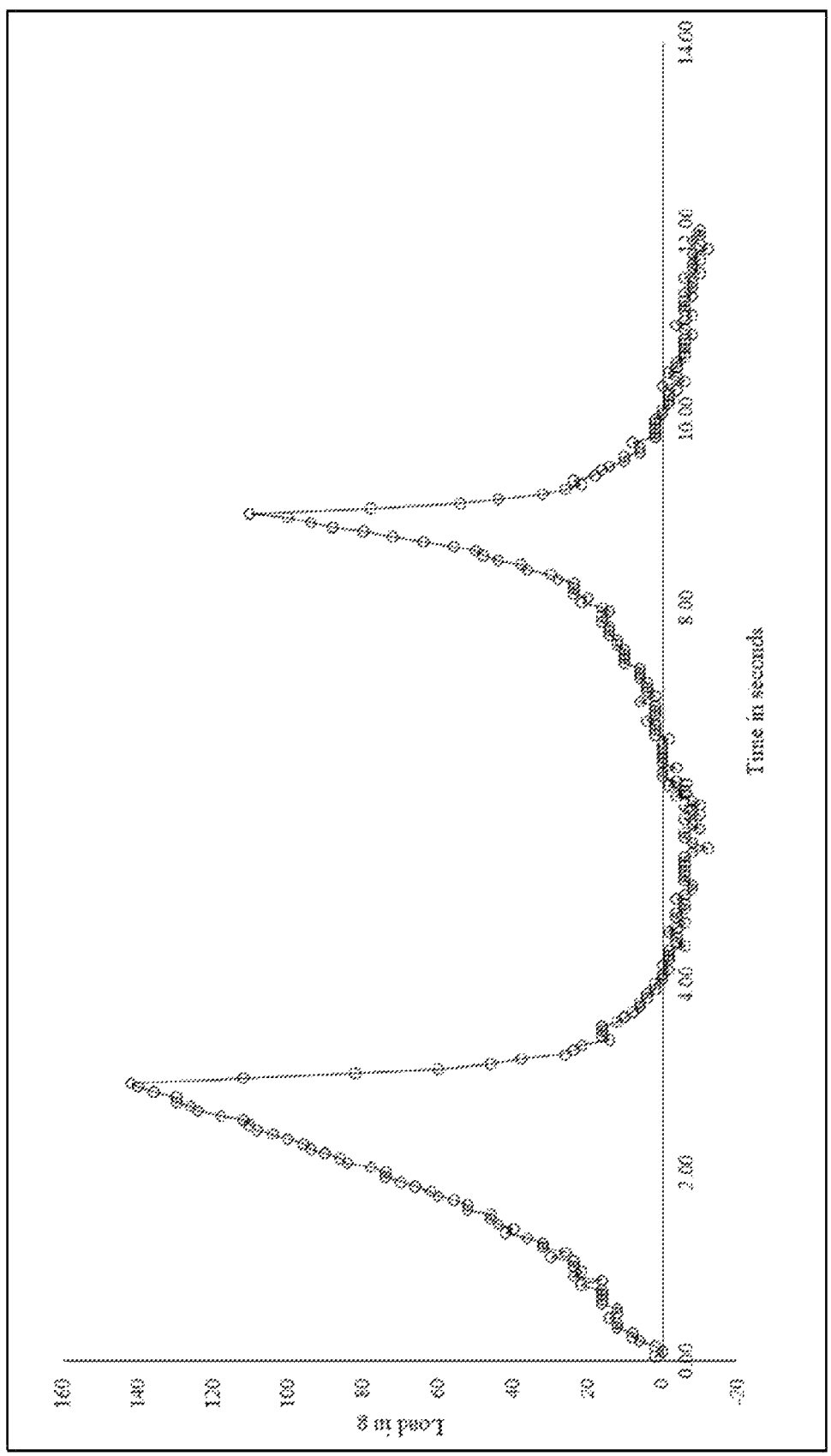
FIG. 12 is a chart showing the texture profiles (load in grams vs. time in seconds) for the chewable gel units formed in accordance with Example 27.
Figure 13:
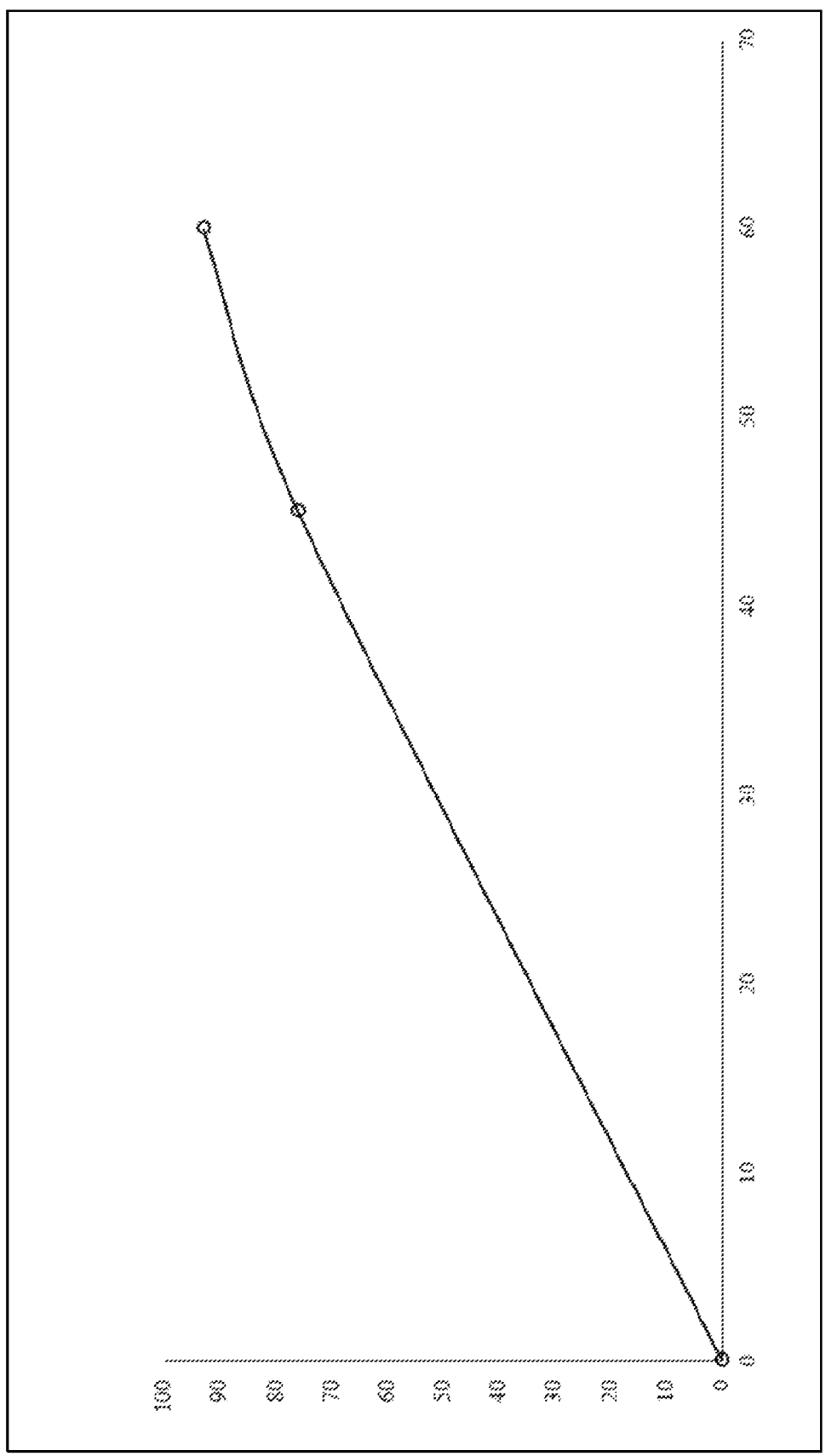
FIG. 13 is a chart showing the dissolution profile (% cumulative average drug released vs. time in minutes) of chewable gel units formed in accordance with Example 1.
Figure 14:
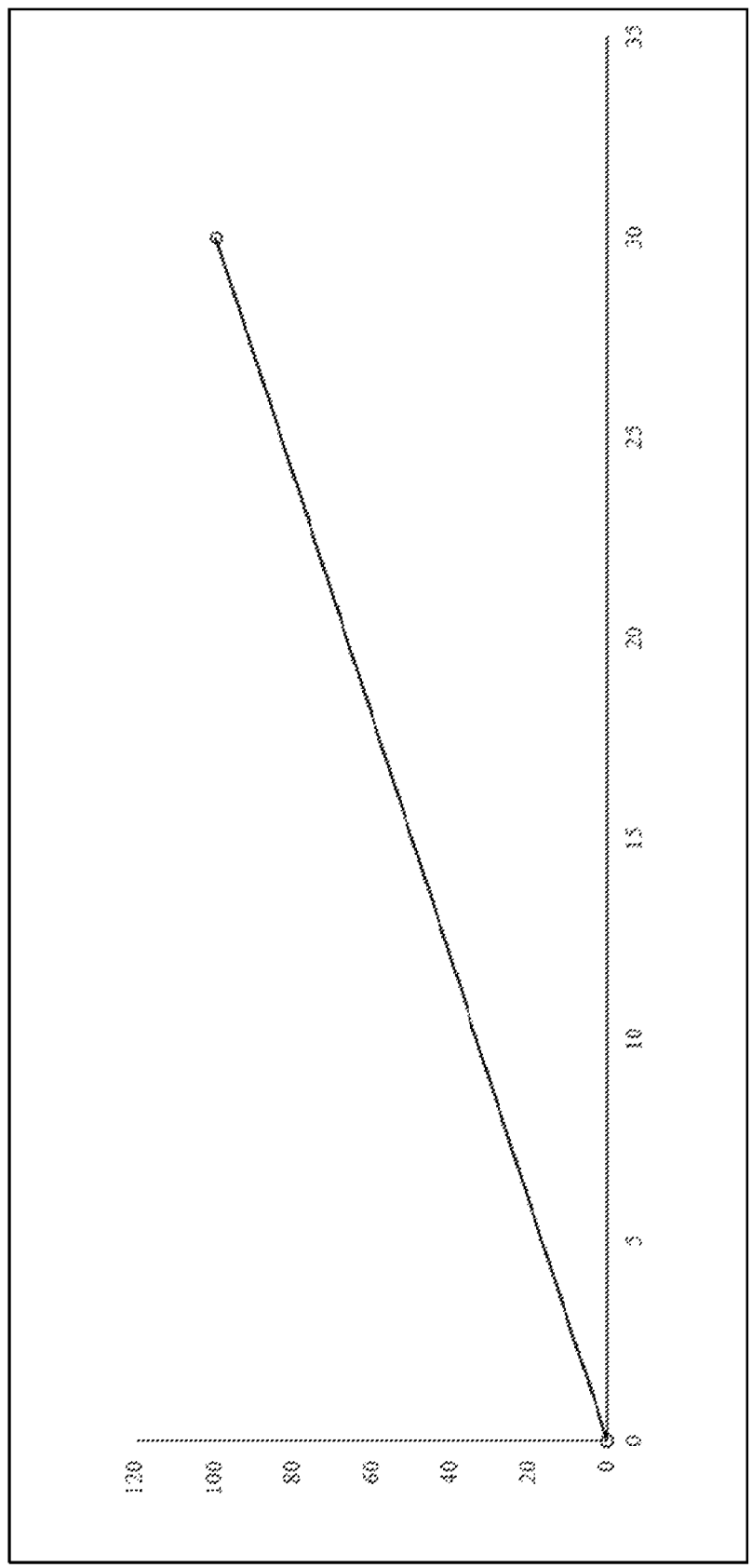
FIG. 14 is a chart showing the dissolution profile (% cumulative average drug released vs. time in minutes) of chewable gel units formed in accordance with Example 2.
Figure 15:
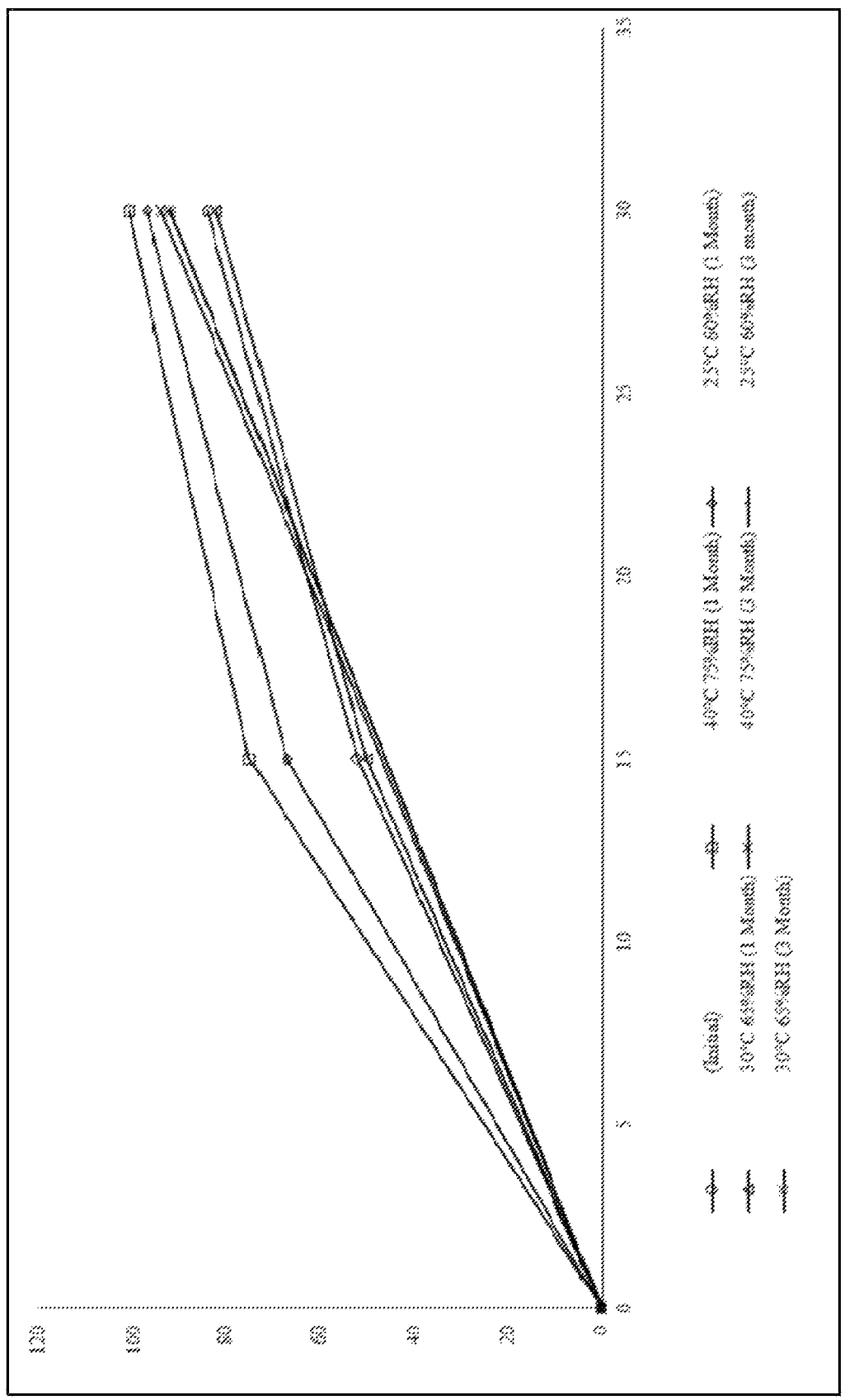
FIG. 15 is a chart showing comparative dissolution profiles (% cumulative average drug released vs. time in minutes) of chewable gel units formed in accordance with Example 4 after being stored for various durations and under various conditions.
Figure 16:
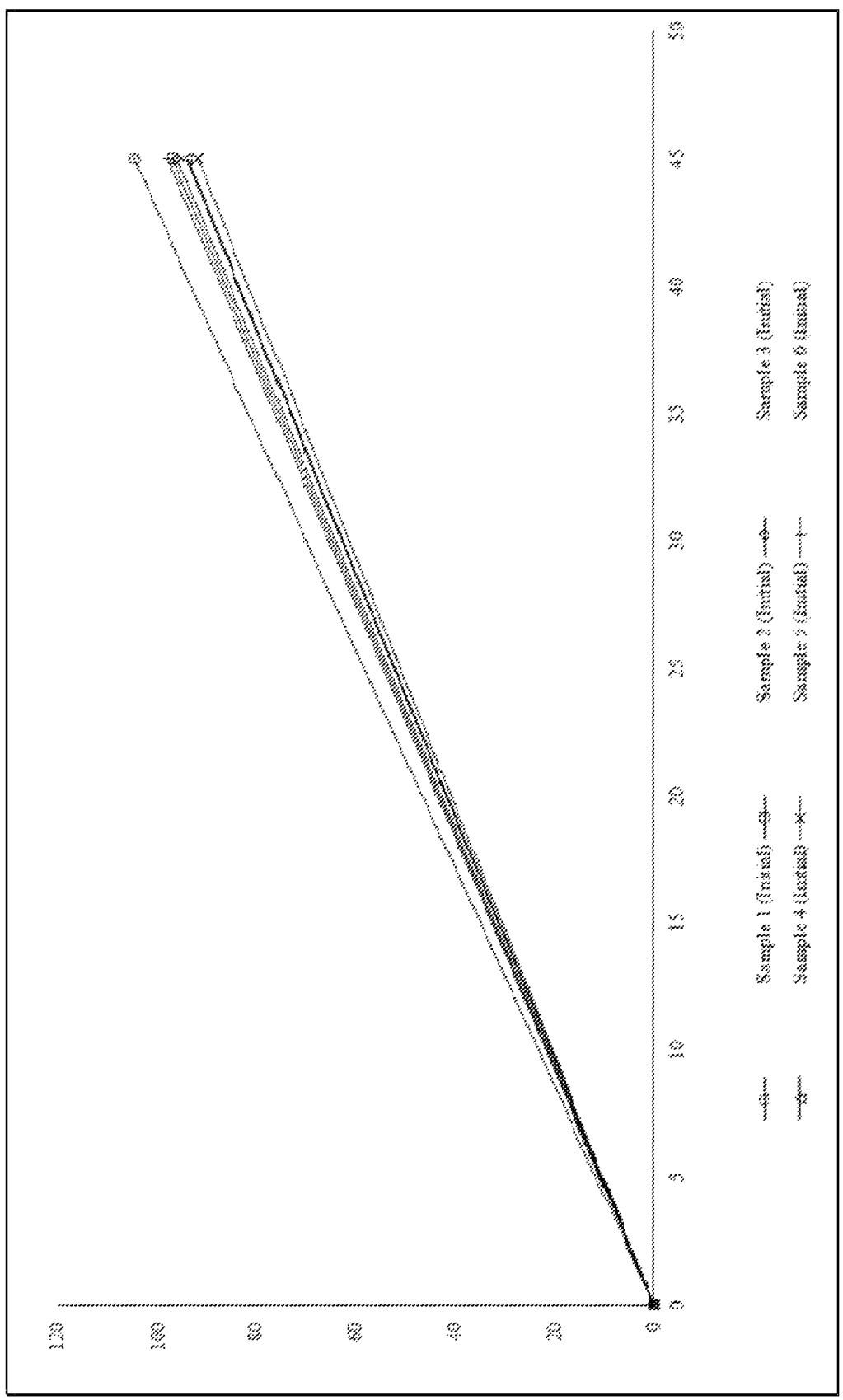
FIG. 16 is a chart showing the dissolution profile (% cumulative average drug released vs. time in minutes) of chewable gel units formed in accordance with Example 5.
Figure 17:
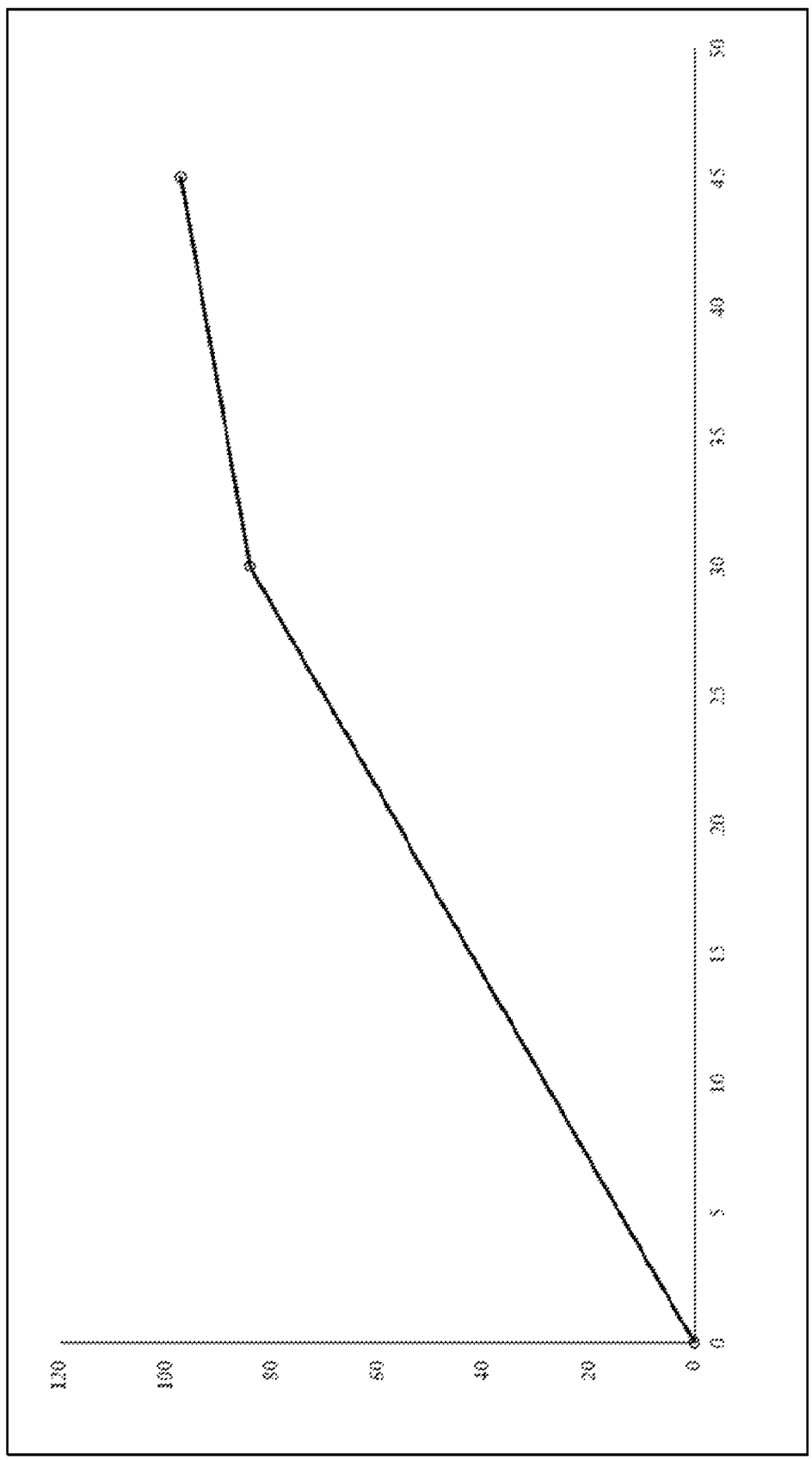
FIG. 17 is a chart showing the dissolution profile (% cumulative average drug released vs. time in minutes) of chewable gel units formed in accordance with Example 6.
Figure 18:
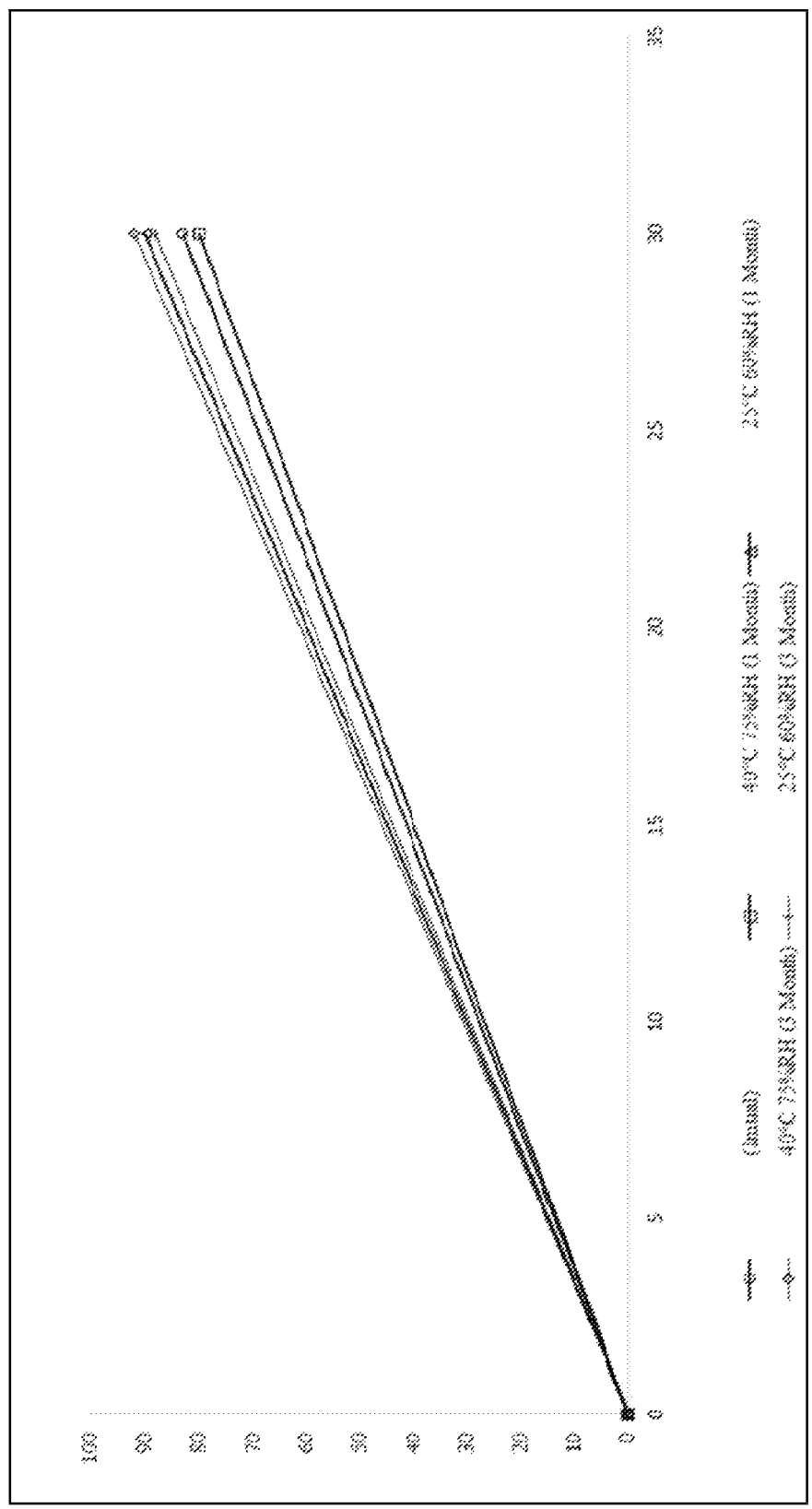
FIG. 18 is a chart showing comparative dissolution profiles (% cumulative average drug released vs. time in minutes) of chewable gel units formed in accordance with Example 7 after being stored for various durations and under various conditions.
Figure 19:
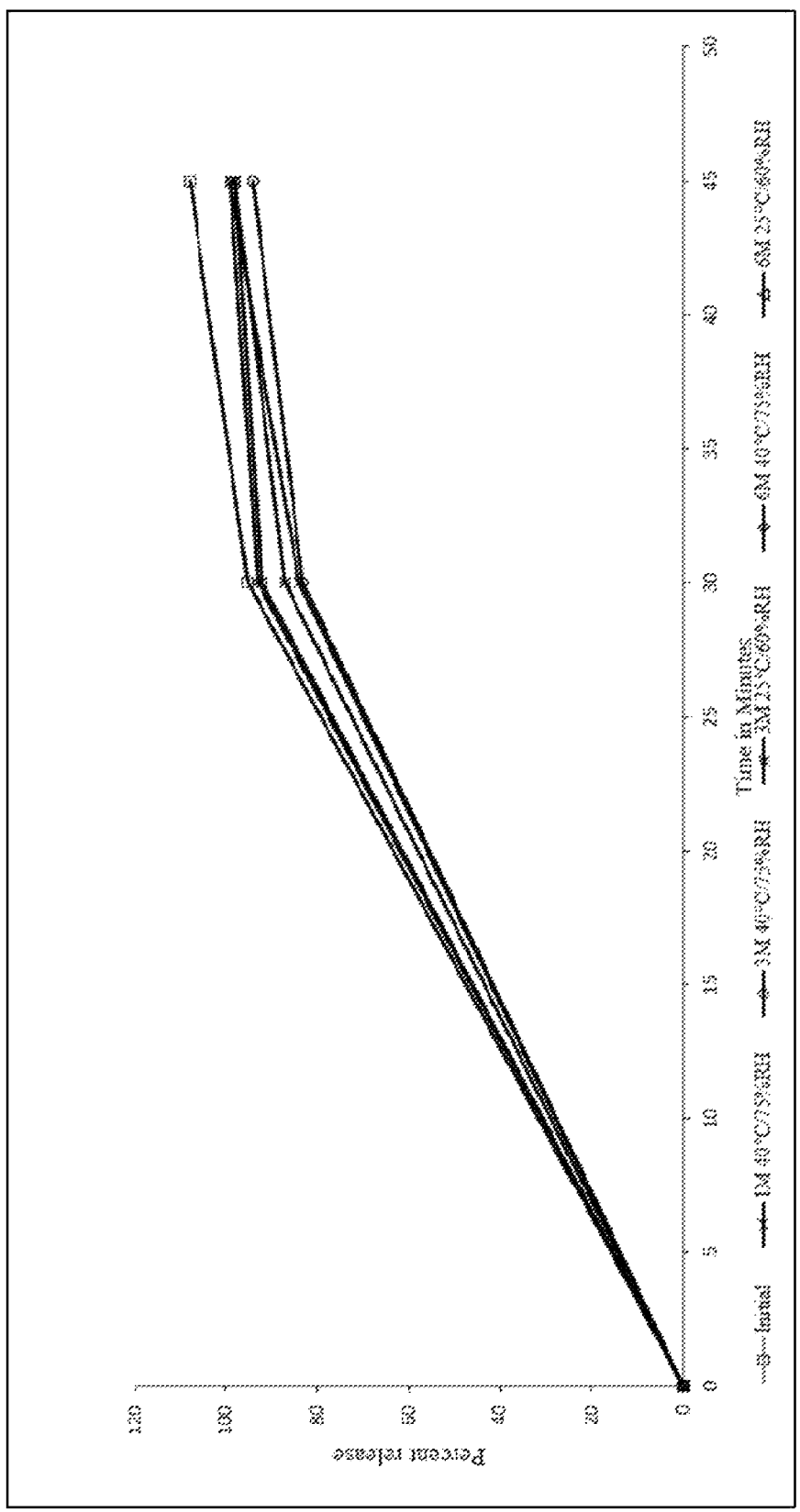
FIG. 19 is a chart showing comparative dissolution profiles (% cumulative average drug released vs. time in minutes) of chewable gel units formed in accordance with Example 9 after being stored for various durations and under various conditions.
Figure 20:
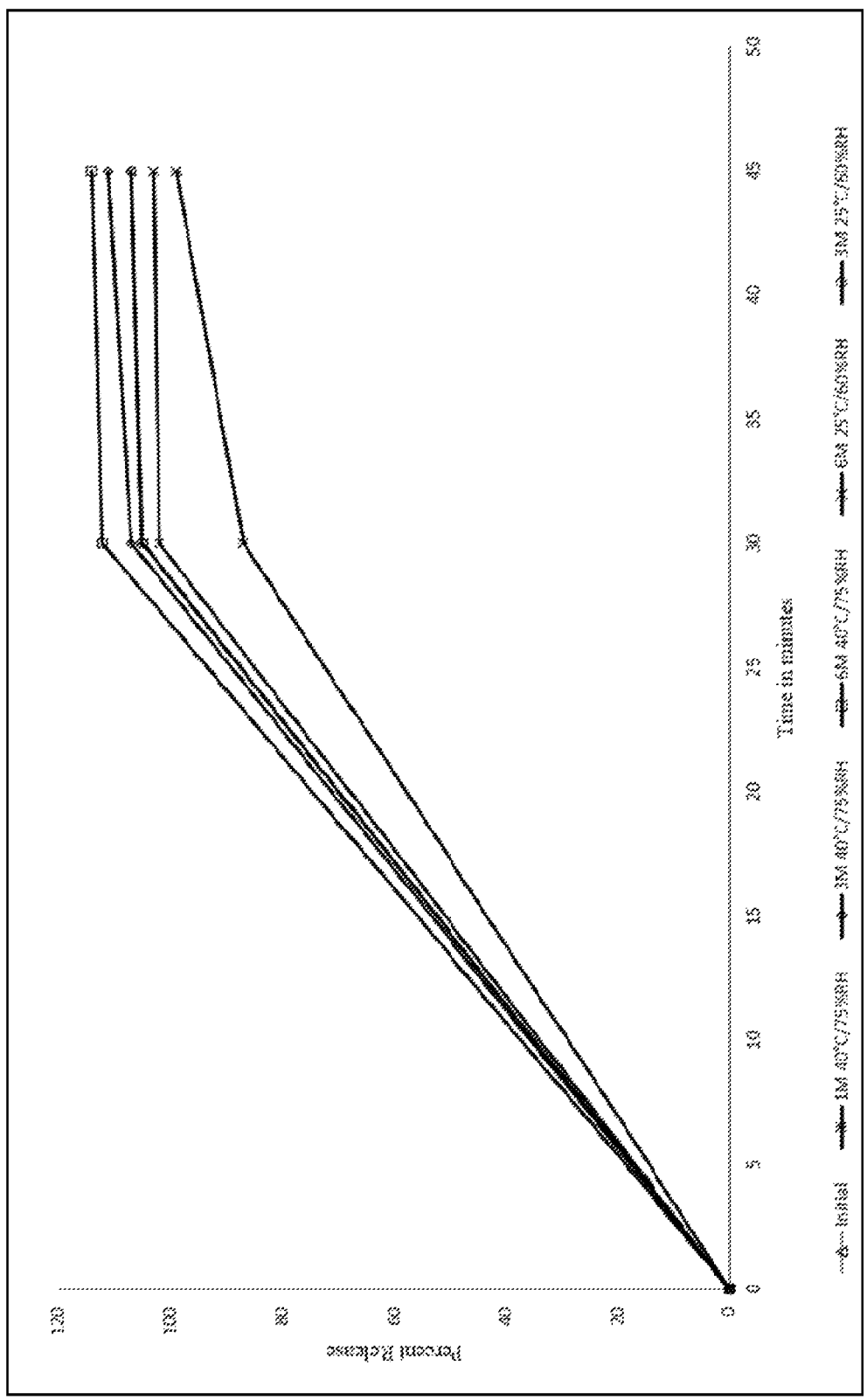
FIG. 20 is a chart showing comparative dissolution profiles (% cumulative average drug released vs. time in minutes) of chewable gel units formed in accordance with Example 10 after being stored for various durations and under various conditions.
Figure 21:
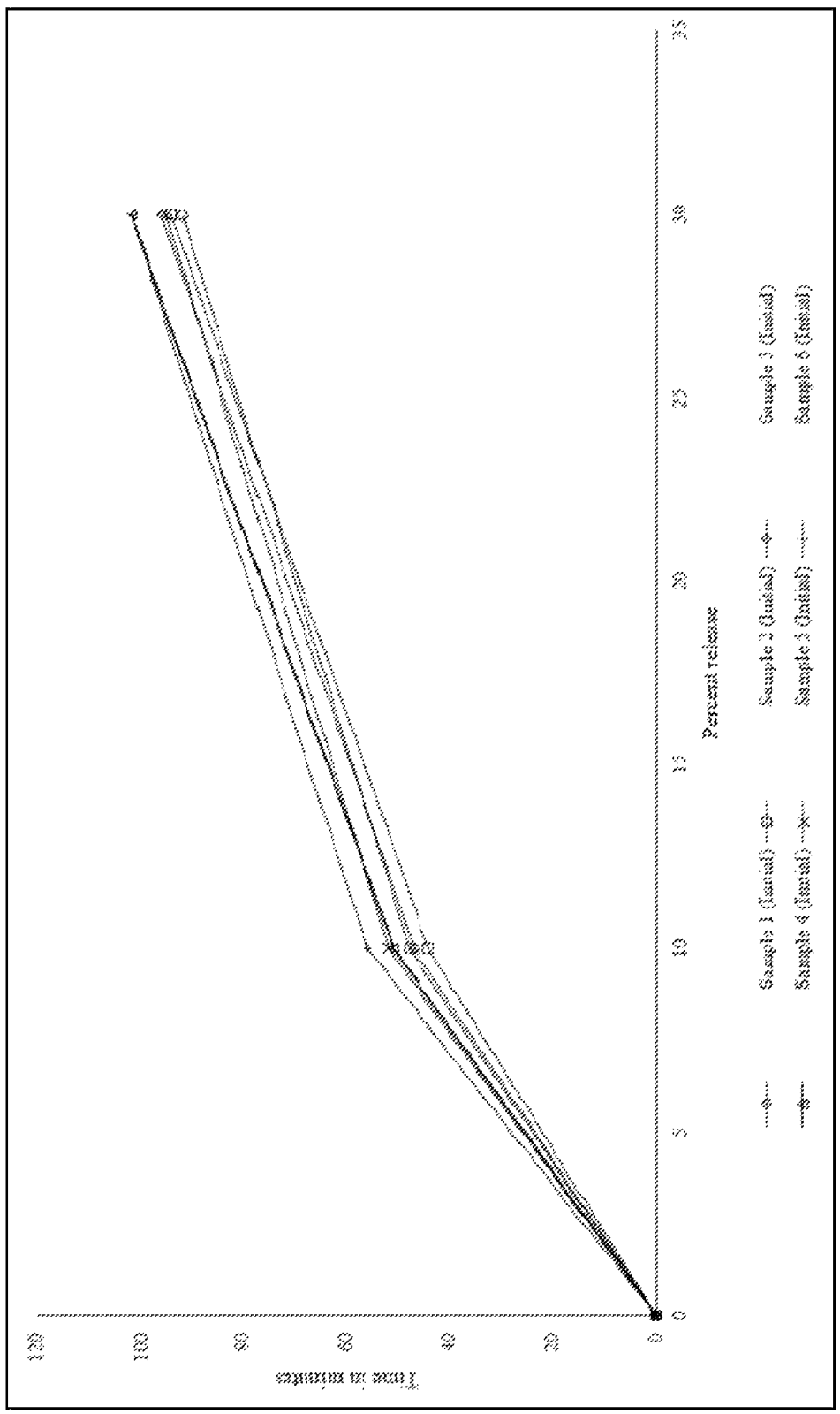
FIG. 21 is a chart showing the dissolution profile (% cumulative average drug released vs. time in minutes) of chewable gel units formed in accordance with Example 11.
Figure 22:
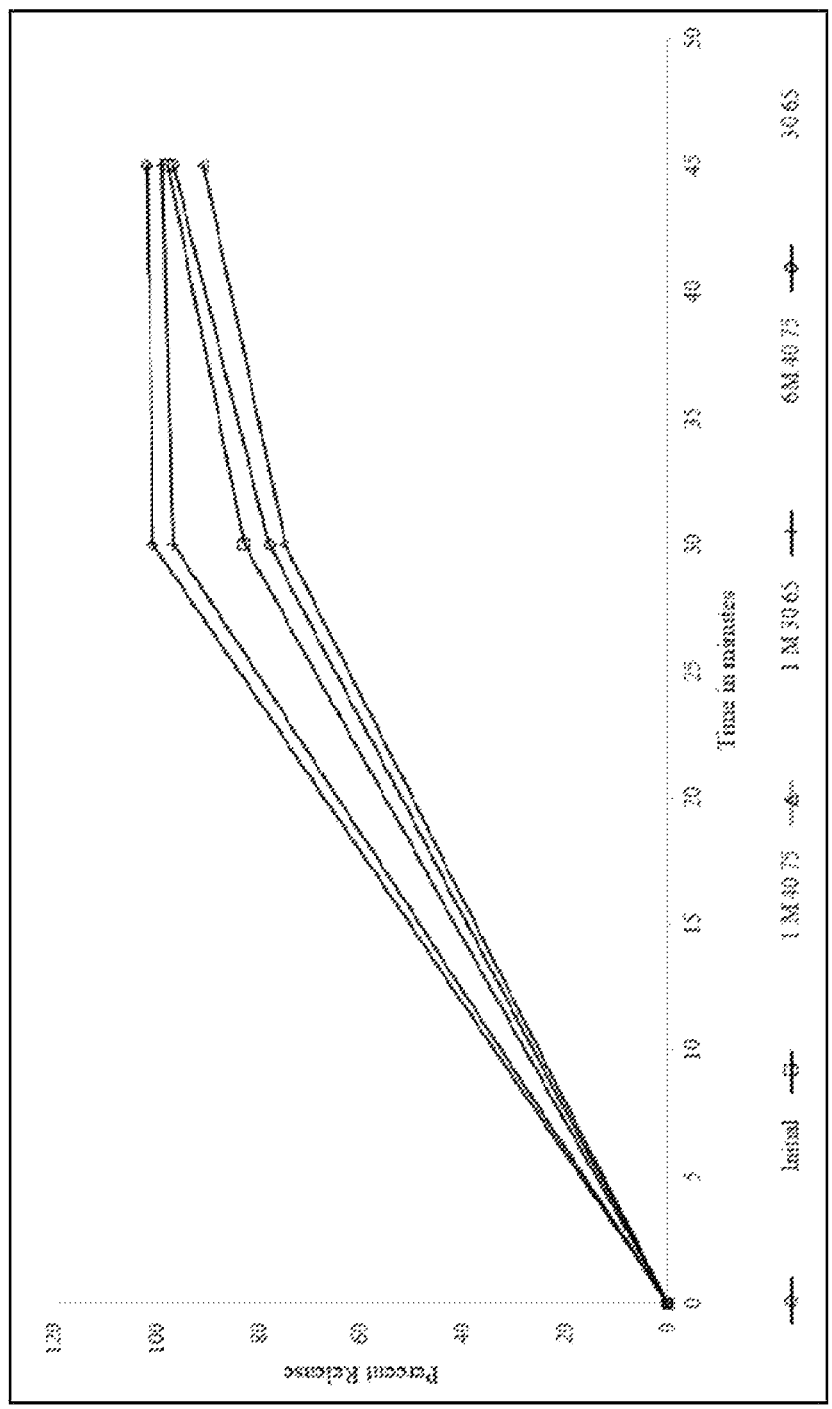
FIG. 22 is a chart showing comparative dissolution profiles (% cumulative average drug released vs. time in minutes) of chewable gel units formed in accordance with Example 13 after being stored for various durations and under various conditions.

FIG. 12 illustrates texture analysis load peaks registered at approximately 3-seconds and 9-seconds performed using TA9 probe, TA-STF fixture, 25,000-gram load cell, 5-gram trigger load over 6-millimeters, 2-millimeter per second pretest speed, and a data rate of twenty points per second (20 points/second) for the chewable gels formed in accordance with Example 27 and stored for 0-days relative to the curing step.

A pH value determination of the chewable gel units manufactured in accordance with the Examples provided herein was performed in accordance with U.S. Pharmacopeia General Chapter <2> Oral drug products—product quality tests, using a two percent (2%) solution of respective chewable gel units.

Table D15 provides information pertaining to the pH value determination of the chewable gel units formed in accordance with the corresponding Examples provided therein shortly after the curing step.

TABLE D15

| Ex # | SD | pH |
|---|---|---|
| 2 | 0 | 4.2 |
| 4 | 0 | 6.24 |
| 6 | 0 | 6.24 |
| 7 | 0 | 5.84 |
| 9 | 0 | 5.99 |
| 10 | 0 | 6.75 |
| 11 | 0 | 5.74 |
| 13 | 0 | 6.1 |
| 14 | 0 | 5.97 |
| 14 | 0 | 6.14 |
| 16 | 0 | 6.6 |
| 17 | 0 | 6.03 |
| 18 | 0 | 6.78 |
| 19 | 0 | 6.52 |
| 20 | 0 | 6.94 |
| 21 | 0 | 6.89 |

Table D16 provides information pertaining to the pH value determination of the chewable gel units formed in accordance with the corresponding Examples provided therein after being stored for a number of days at a temperature of 25° C. and a relative humidity of 60%.

TABLE D16

| Ex # | SD | pH |
|---|---|---|
| 4 | 30 | 6.15 |
| 4 | 90 | 6.67 |
| 7 | 30 | 6.07 |
| 9 | 180 | 8 |
| 10 | 90 | 6.35 |
| 10 | 180 | 6.27 |
| 13 | 90 | 6.38 |
| 14 | 90 | 6.21 |
| 14 | 180 | 6.28 |
| 16 | 90 | 6.84 |
| 16 | 180 | 6.69 |
| 16 | 180 | 6.66 |
| 17 | 90 | 5.98 |
| 17 | 180 | 5.99 |
| 18 | 90 | 6.74 |
| 19 | 90 | 6.28 |

Table D17 provides information pertaining to the pH value determination of the chewable gel units formed in accordance with the corresponding Examples provided therein after being stored for a number of days at a temperature of 40° C. and a relative humidity of 75%.

TABLE D17

| Ex # | SD | pH |
|---|---|---|
| 4 | 30 | 6.31 |
| 4 | 90 | 6.43 |
| 7 | 30 | 6.23 |
| 9 | 180 | 8.2 |
| 10 | 30 | 6.36 |
| 10 | 90 | 6.19 |
| 10 | 180 | 5.99 |
| 13 | 30 | 6.19 |
| 13 | 90 | 6.54 |
| 14 | 30 | 6.31 |
| 14 | 90 | 5.88 |
| 14 | 180 | 5.9 |
| 16 | 30 | 6.64 |
| 16 | 90 | 6.63 |
| 16 | 180 | 6.43 |
| 17 | 30 | 6.09 |
| 17 | 90 | 6.09 |
| 17 | 180 | 6.12 |
| 18 | 30 | 6.7 |
| 18 | 90 | 6.51 |
| 19 | 30 | 6.45 |
| 19 | 90 | 6.6 |

Table D18 provides information pertaining to the pH value determination of the chewable gel units formed in accordance with the corresponding Examples provided therein after being stored for a number of days at a temperature of 30° C. and a relative humidity of 65%.

TABLE D18

| Ex # | SD | pH |
|---|---|---|
| 4 | 30 | 6.33 |
| 4 | 90 | 6.51 |
| 13 | 30 | 6.22 |
| 13 | 90 | 6.4 |

A loss-on-drying analysis of the chewable gel units manufactured in accordance with the Examples provided herein was performed in accordance with U.S. Pharmacopeia General Chapter <731> Loss on Drying. Table D19 provides information pertaining to the loss-on-drying analysis of the chewable gel units formed in accordance with the corresponding Examples provided therein shortly after the curing step. Table D19 includes values for percentage of mass loss ("LoD") given in percent and the temperature (in degrees Celsius) at which the chewable gels were heated ("TH").

TABLE D19

| Ex # | SD | TH | LoD |
|---|---|---|---|
| 4 | 0 | 95 | 5.74% |
| 6 | 0 | 95 | 5.74% |
| 7 | 0 | 95 | 6.10% |
| 9 | 0 | 95 | 5.60% |
| 10 | 0 | 105 | 3.60% |
| 11 | 0 | 95 | 13.61% |
| 13 | 0 | 95 | 8.00% |
| 14 | 0 | 95 | 15.78% |
| 16 | 0 | 105 | 11.30% |
| 17 | 0 | 105 | 12.86% |
| 18 | 0 | 105 | 10.50% |
| 19 | 0 | 105 | 9.41% |
| 20 | 0 | 105 | 7.80% |
| 21 | 0 | 105 | 12.20% |

Table D20 provides information pertaining to the loss-on-drying analysis of the chewable gel units formed in accordance with the corresponding Examples provided therein after being stored for a number of days at a temperature of 25° C. and a relative humidity of 60%. Table D20 includes values for percentage of mass loss ("LoD") given in percent and the temperature (in degrees Celsius) at which the chewable gels were heated ("TH").

TABLE D20

| Ex # | SD | TH | LoD |
|---|---|---|---|
| 4 | 30 | 95 | 9.21% |
| 4 | 90 | 95 | 9.74% |
| 7 | 30 | 95 | 6.30% |
| 9 | 180 | 95 | 8.00% |
| 10 | 90 | 105 | 11.12% |
| 10 | 180 | 105 | 8.80% |
| 13 | 90 | 95 | 12.70% |
| 14 | 90 | 95 | 10.16% |
| 14 | 180 | 95 | 10.40% |
| 16 | 90 | 105 | 12.20% |
| 16 | 180 | 105 | 10.07% |
| 16 | 180 | 105 | 10.51% |
| 17 | 90 | 105 | 9.00% |
| 17 | 180 | 105 | 8.10% |
| 18 | 90 | 105 | 10.15% |
| 19 | 90 | 105 | 8.90% |

Table D21 provides information pertaining to the loss-on-drying analysis of the chewable gel units formed in accordance with the corresponding Examples provided therein after being stored for a number of days at a temperature of 40° C. and a relative humidity of 75%. Table D21 includes values for percentage of mass loss ("LoD") given in percent and the temperature (in degrees Celsius) at which the chewable gels were heated ("TH").

TABLE D21

| Ex # | SD | TH | LoD |
|---|---|---|---|
| 4 | 30 | 95 | 10.17% |
| 4 | 90 | 95 | 10.59% |

TABLE D21-continued

| Ex # | SD | TH | LoD |
|---|---|---|---|
| 7 | 30 | 95 | 6.50% |
| 9 | 180 | 95 | 8.20% |
| 10 | 30 | 105 | 7.40% |
| 10 | 90 | 105 | 10.40% |
| 10 | 180 | 105 | 7.80% |
| 13 | 30 | 95 | 5.58% |
| 13 | 90 | 95 | 10.90% |
| 14 | 30 | 95 | 9.00% |
| 14 | 90 | 95 | 9.56% |
| 14 | 180 | 95 | 10.30% |
| 16 | 30 | 105 | 9.00% |
| 16 | 90 | 105 | 12.00% |
| 16 | 180 | 105 | 10.57% |
| 17 | 30 | 105 | 8.50% |
| 17 | 90 | 105 | 8.90% |
| 17 | 180 | 105 | 9.50% |
| 18 | 30 | 105 | 6.90% |
| 18 | 90 | 105 | 9.94% |
| 19 | 30 | 105 | 9.25% |
| 19 | 90 | 105 | 9.40% |

Table D22 provides information pertaining to the loss-on-drying analysis of the chewable gel units formed in accordance with the corresponding Examples provided therein after being stored for a number of days at a temperature of 30° C. and a relative humidity of 60%. Table D22 includes values for percentage of mass loss ("LoD") given in percent and the temperature (in degrees Celsius) at which the chewable gels were heated ("TH").

TABLE D22

| Ex # | SD | TH | LoD |
|---|---|---|---|
| 4 | 30 | 95 | 11.57% |
| 4 | 90 | 95 | 9.53% |
| 13 | 30 | 95 | 7.17% |
| 13 | 90 | 95 | 11.60% |

An impurity analysis of the chewable gel units manufactured in accordance with the Examples provided herein was performed. Table D23 provides information pertaining to the impurity analysis of the chewable gel units formed in accordance with the corresponding Examples provided therein shortly after the curing step. Table D23 includes values for: assay percentage ("Asy %"); highest impurity percentage ("HIP %"); and percentage of total impurity ("TI %"). As used in Table D23, "ND" means none detected.

TABLE D23

| Ex # | Asy % | HIP % | TI % |
|---|---|---|---|
| 2 | 111.8 | ND | ND |
| 4 | 105 | 0.3 | 0.55 |
| 6 | 105 | 0.3 | 0.55 |
| 7 | 112.4 | ND | ND |
| 9 | 108.7 | 0.06 | 0.06 |
| 9 | 108.7 | 0.06 | 0.06 |
| 10 | 104.2 | 0.22 | 0.47 |
| 11 | 102.3 | 0 | 0 |
| 13 | 108 | 0.07 | 0.07 |
| 14 | 114.8 | ND | ND |
| 15 | 97.5 | ND | ND |
| 16 | 100.9 | ND | ND |
| 18 | 95.2 | 0.14 | 0.36 |
| 19 | 100.2 | 0.09 | 0.19 |
| 20 | 95.7 | — | — |
| 21 | 103.9 | — | — |

Table D24 provides information pertaining to the impurity analysis of the chewable gel units formed in accordance with the corresponding Examples provided therein after being stored for a number of days at a temperature of 25° C. and a relative humidity of 60%. Table D24 includes values for: assay percentage ("Asy %"); highest impurity percentage ("HIP %"); and percentage of total impurity ("TI %"). As used in Table D24, "ND" means none detected.

TABLE D24

| Ex # | SD | Asy % | HIP % | TI % |
|---|---|---|---|---|
| 4 | 30 | 100.4 | 0.33 | 0.63 |
| 4 | 90 | 99.8 | 0.05 | 0.05 |
| 7 | 30 | 83.5 | ND | ND |
| 7 | 90 | 102.9 | ND | ND |
| 7 | 180 | 109.9 | 0.01 | 0.01 |
| 9 | 90 | 110.1 | ND | ND |
| 9 | 180 | 104.5 | 0.06 | 0.06 |
| 10 | 90 | 103.4 | 0.24 | 0.53 |
| 10 | 180 | 102 | 0.22 | 0.45 |
| 13 | 90 | 103.9 | ND | ND |
| 16 | 90 | 96.8 | 0.9 | 0.01 |
| 16 | 180 | 100.5 | 0.0003 | 0.0004 |
| 16 | 180 | 100.5 | 0.0006 | 0.0007 |
| 18 | 90 | 97.6 | ND | 0.45 |
| 19 | 90 | 98.7 | 0.19 | 0.31 |

Table D25 provides information pertaining to the impurity analysis of the chewable gel units formed in accordance with the corresponding Examples provided therein after being stored for a number of days at a temperature of 40° C. and a relative humidity of 75%. Table D25 includes values for: assay percentage ("Asy %"); highest impurity percentage ("HIP %"); and percentage of total impurity ("TI %"). As used in Table D25, "ND" means none detected.

TABLE D25

| Ex # | SD | Asy % | HIP % | TI % |
|---|---|---|---|---|
| 4 | 30 | 96.6 | 0.44 | 0.92 |
| 4 | 90 | 99.2 | 0.32 | 0.37 |
| 7 | 30 | 95.4 | ND | ND |
| 7 | 90 | 115.3 | 0.03 | 0.03 |
| 7 | 180 | 106.8 | 0.06 | 0.06 |
| 9 | 30 | 107.1 | 0.07 | 0.07 |
| 9 | 90 | 119 | ND | ND |
| 9 | 180 | 105.5 | 0.02 | 0.02 |
| 10 | 30 | 99.6 | 0.29 | 0.63 |
| 10 | 90 | 103.9 | 0.48 | 0.94 |
| 10 | 180 | 101.1 | 0.77 | 1.2 |
| 13 | 30 | 105 | ND | ND |
| 13 | 90 | 107 | ND | ND |
| 13 | 180 | 103.2 | ND | ND |
| 16 | 30 | 93.1 | ND | ND |
| 16 | 90 | 97.3 | 0.09 | 0.1 |
| 16 | 180 | 97.8 | 0.0002 | 0.0003 |
| 18 | 30 | 94.9 | ND | 0.34 |
| 18 | 90 | 94.2 | 0.02 | 0.51 |
| 19 | 30 | 98.8 | 0.29 | 0.42 |
| 19 | 90 | 97.1 | 0.55 | 0.71 |

Table D26 provides information pertaining to the impurity analysis of the chewable gel units formed in accordance with the corresponding Examples provided therein after being stored for a number of days at a temperature of 30° C. and a relative humidity of 65%. Table D26 includes values for: assay percentage ("Asy %"); highest impurity percentage ("HIP %"); and percentage of total impurity ("TI %"). As used in Table D26, "ND" means none detected.

TABLE D26

| Ex # | SD | Asy % | HIP % | TI % |
|---|---|---|---|---|
| 4 | 30 | 97.9 | 0.35 | 0.68 |
| 4 | 90 | 101.6 | 0.08 | 0.12 |
| 13 | 30 | 113.2 | ND | ND |
| 13 | 90 | 102.1 | ND | ND |
| 13 | 180 | 104 | ND | ND |

A disintegration analysis of the chewable gel units made in accordance with the Examples provided herein was performed in accordance with U.S. Pharmacopeia General Chapter <701> Disintegration. In each instance, the disintegration analysis was performed using nine hundred milliliters (900 ml) of water at a temperature of about 37° C. (±2° C.) and a sample size of six (6) chewable gel units. Table D27 provides information pertaining to the disintegration analysis of the chewable gel units formed in accordance with the corresponding Examples provided therein shortly after the curing step. Table D27 includes values for disintegration time ("DT") provided in minutes.

TABLE D27

| Ex # | DT |
|---|---|
| 2 | 30 |
| 4 | 35 |
| 6 | 35 |
| 7 | 25 |
| 9 | 31 |
| 10 | 35 |
| 13 | 28 |
| 14 | 32 |
| 15 | 35 |
| 18 | 50 |
| 22 | 40 |
| 23 | 35 |
| 24 | 37 |
| 25 | 35 |
| 26 | 37 |
| 27 | 55 |

A dissolution analysis of the chewable gel units manufactured in accordance with the Examples provided herein was performed in close accordance with U.S. Pharmacopeia General Chapter <711> Dissolution. The analysis parameters of the dissolution analysis are included in Table D28 and include the following: type of apparatus used ("Apparatus"); rotations per minute ("RPM"); dissolution medium ("Medium"); and volume of medium ("MV") given in milliliters (mL).

TABLE D28

| Ex # | Apparatus | RPM | Medium | MV |
|---|---|---|---|---|
| 2 | USP Apparatus II | 50 | Water | 900 |
| 4 | USP Apparatus I (10-Mesh) | 100 | Water | 500 |
| 4 | USP Apparatus I (10-Mesh) | 100 | Water | 500 |
| 5 | USP Apparatus I (10-Mesh) | 100 | Water | 500 |
| 6 | USP Apparatus I (10-Mesh) | 100 | Water | 500 |
| 7 | USP Apparatus II | 50 | 0.1 N HCl | 500 |
| 9 | USP Apparatus II | 50 | Water | 900 |
| 10 | USP Apparatus II | 50 | Water | 900 |
| 11 | USP Apparatus II | 50 | 0.001 N HCl | 900 |
| 13 | USP Apparatus II | 75 | Water | 900 |
| 14 | USP Apparatus II | 50 | Water | 900 |
| 15 | USP Apparatus II | 50 | SGF w/o P | 900 |
| 16 | USP apparatus II | 75 | Water | 900 |
| 17 | USP Apparatus II | 100 | Water | 500 |
| 18 | USP apparatus II | 100 | citrate buffer (2.2 pH) | 1000 |
| 19 | USP apparatus II | 50 | Water | 900 |
| 20 | USP apparatus II | 50 | Water | 900 |
| 21 | USP apparatus II | 50 | Water | 900 |

Table D29 provides information pertaining to the dissolution analysis of the chewable gel units formed in accordance with the corresponding Examples provided therein shortly after the curing step. Table D29 includes values for: run time ("RT") provided in minutes; average release percentage ("AR %"); minimum release percentage ("Min-R %"); maximum release percentage ("Max-R %"); and relative standard deviation ("RSD"). In each instance, the sample size used for the dissolution analysis was six (6) chewable gel units, the temperature of the medium was thirty-seven degrees Celsius (37° C.) (±2° C.), and the volume of the medium replenished was ten milliliters (10 ml).

TABLE D29

| Ex # | RT | AR % | Min-R % | Max-R % | RSD |
|---|---|---|---|---|---|
| 2 | 30 | 100 | 93 | 104 | 3.84 |
| 4 | 30 | 84 | 77 | 90 | 5.9 |
| 4 | 45 | 97 | 90 | 102 | 5.14 |
| 5 | 30 | 97 | 92 | 105 | 4.6 |
| 6 | 30 | 84 | 77 | 90 | 5.9 |
| 6 | 30 | 84 | 77 | 90 | 5.9 |
| 6 | 45 | 97 | 90 | 102 | 5.14 |
| 7 | 30 | 83 | 75 | 88 | 5.8 |
| 9 | 30 | 95 | 92 | 102 | 3.77 |
| 9 | 45 | 108 | 104 | 112 | 3.04 |
| 9 | 45 | 108 | 104 | 112 | 3.04 |
| 10 | 30 | 105 | 97 | 110 | 4.47 |
| 10 | 45 | 107 | 101 | 112 | 3.64 |
| 11 | 10 | 50 | 44 | 56 | 8.51 |
| 11 | 30 | 97 | 92 | 102 | 4.35 |
| 13 | 30 | 78 | 70 | 91 | 8.92 |
| 13 | 45 | 97 | 90 | 114 | 8.96 |
| 14 | 45 | 107 | 100 | 112 | 3.88 |
| 15 | 45 | 76 | 69 | 84 | 6.76 |
| 15 | 60 | 93 | 88 | 100 | 4.37 |
| 16 | 45 | 98 | 96 | 101 | — |
| 17 | 30 | 44 | 40 | 48 | — |
| 17 | 45 | 69 | 64 | 73 | — |
| 17 | 60 | 79 | 74 | 84 | — |
| 18 | 45 | 84 | 79 | 87 | — |
| 19 | 30 | 99 | 96 | 103 | — |
| 19 | 45 | 105 | 103 | 105 | — |
| 20 | 45 | 85 | 83 | 88 | — |
| 21 | 30 | 57 | 53 | 61 | — |
| 21 | 45 | 79 | 75 | 82 | — |

Table D30 provides information pertaining to the dissolution analysis of the chewable gel units formed in accordance with the corresponding Examples provided therein after being stored for thirty (30) days at a temperature of 40° C. and a relative humidity of 75%. Table D30 includes values for: run time ("RT") provided in minutes; average release percentage ("AR %"); minimum release percentage ("Min-R %"); maximum release percentage ("Max-R %"); and relative standard deviation ("RSD"). In each instance, the sample size used for the dissolution analysis was six (6) chewable gel units, the temperature of the medium was thirty-seven degrees Celsius (37° C.) (±2° C.), and the volume of the medium replenished was ten milliliters (10 ml).

TABLE D30

| Ex # | RT | AR % | Min-R % | Max-R % | RSD |
|---|---|---|---|---|---|
| 4 | 30 | 101 | 95 | 109 | 4.57 |
| 4 | 45 | 103 | 98 | 110 | 3.86 |
| 7 | 30 | 80 | 75 | 88 | 6.6 |
| 9 | 30 | 84 | 71 | 101 | 13.95 |
| 9 | 45 | 99 | 89 | 107 | 7.43 |
| 10 | 30 | 87 | 76 | 95 | 8.5 |
| 10 | 45 | 99 | 93 | 108 | 6.16 |
| 13 | 30 | 83 | 76 | 89 | 6.69 |
| 13 | 45 | 98 | 90 | 104 | 5.81 |
| 14 | 45 | 105 | 102 | 107 | 1.85 |
| 16 | 45 | 92 | 83 | 95 | — |
| 17 | 30 | 58 | 49 | 66 | — |
| 18 | 45 | 86 | 81 | 91 | — |
| 19 | 30 | 73 | 68 | 77 | — |
| 19 | 45 | 93 | 89 | 97 | — |

Table D31 provides information pertaining to the dissolution analysis of the chewable gel units formed in accordance with the corresponding Examples provided therein after being stored for thirty (30) days at a temperature of 25° C. and a relative humidity of 60%. Table D31 includes values for: run time ("RT") provided in minutes; average release percentage ("AR %"); minimum release percentage ("Min-R %"); maximum release percentage ("Max-R %"); and relative standard deviation ("RSD"). In each instance, the sample size used for the dissolution analysis was six (6) chewable gel units, the temperature of the medium was thirty-seven degrees Celsius (37° C.) (±2° C.), and the volume of the medium replenished was ten milliliters (10 ml).

TABLE D31

| Ex # | RT | AR % | Min-R % | Max-R % | RSD |
|---|---|---|---|---|---|
| 4 | 30 | 97 | 90 | 104 | 5.31 |
| 4 | 45 | 103 | 95 | 111 | 6.35 |
| 7 | 30 | 90 | 80 | 94 | 6.07 |
| 13 | 30 | 75 | 67 | 83 | 8.37 |
| 13 | 45 | 91 | 79 | 98 | 7.2 |

Table D32 provides information pertaining to the dissolution analysis of the chewable gel units formed in accordance with the corresponding Examples provided therein after being stored for ninety (90) days at a temperature of 40° C. and a relative humidity of 75%. Table D32 includes values for: run time ("RT") provided in minutes; average release percentage ("AR %"); minimum release percentage ("Min-R %"); maximum release percentage ("Max-R %"); and relative standard deviation ("RSD"). In each instance, the sample size used for the dissolution analysis was six (6) chewable gel units, the temperature of the medium was thirty-seven degrees Celsius (37° C.) (±2° C.), and the volume of the medium replenished was ten milliliters (10 ml).

TABLE D32

| Ex # | RT | AR % | Min-R % | Max-R % | RSD |
|---|---|---|---|---|---|
| 4 | 30 | 94 | 86 | 97 | 4.14 |
| 7 | 30 | 92 | 78 | 99 | 8.04 |
| 9 | 30 | 83 | 75 | 102 | 11.84 |
| 9 | 45 | 94 | 85 | 107 | 8.99 |
| 9 | 45 | 94 | 85 | 107 | 8.99 |
| 10 | 30 | 107 | 102 | 110 | 3.01 |
| 10 | 45 | 111 | 106 | 116 | 3.92 |
| 13 | 30 | 104 | 101 | 105 | 1.47 |
| 14 | 45 | 112 | 108 | 118 | 3.59 |
| 16 | 45 | 100 | 94 | 103 | — |
| 17 | 30 | 71 | 65 | 78 | — |
| 17 | 45 | 86 | 81 | 89 | — |
| 17 | 60 | 97 | 93 | 99 | — |
| 18 | 45 | 89 | 82 | 93 | — |
| 19 | 30 | 67 | 65 | 70 | — |
| 19 | 45 | 86 | 84 | 88 | — |

Table D33 provides information pertaining to the dissolution analysis of the chewable gel units formed in accordance with the corresponding Examples provided therein after being stored for ninety (90) days at a temperature of 25° C. and a relative humidity of 60%. Table D33 includes values for: run time ("RT") provided in minutes; average release percentage ("AR %"); minimum release percentage ("Min-R %"); maximum release percentage ("Max-R %"); and relative standard deviation ("RSD"). In each instance, the sample size used for the dissolution analysis was six (6) chewable gel units, the temperature of the medium was thirty-seven degrees Celsius (37° C.) (±2° C.), and the volume of the medium replenished was ten milliliters (10 ml).

TABLE D33

| Ex # | RT | AR % | Min-R % | Max-R % | RSD |
|---|---|---|---|---|---|
| 4 | 30 | 92 | 83 | 99 | 5.58 |
| 7 | 30 | 88 | 79 | 94 | 6.06 |
| 9 | 30 | 87 | 82 | 91 | 4.91 |
| 9 | 45 | 98 | 94 | 101 | 2.89 |
| 9 | 45 | 98 | 94 | 101 | 2.89 |
| 10 | 30 | 105 | 95 | 112 | 5.71 |
| 10 | 45 | 107 | 102 | 112 | 3.84 |
| 13 | 30 | 101 | 100 | 104 | 1.35 |
| 14 | 45 | 110 | 105 | 116 | 3.95 |
| 16 | 45 | 101 | 95 | 105 | — |
| 17 | 30 | 63 | 53 | 71 | — |
| 17 | 45 | 82 | 77 | 89 | — |
| 17 | 60 | 95 | 92 | 97 | — |
| 18 | 45 | 83 | 80 | 87 | — |
| 19 | 30 | 64 | 62 | 66 | — |
| 19 | 45 | 85 | 81 | 87 | — |

Table D34 provides information pertaining to the dissolution analysis of the chewable gel units formed in accordance with the corresponding Examples provided therein after being stored for one hundred eighty (180) days at a temperature of 40° C. and a relative humidity of 75%. Table D34 includes values for: run time ("RT") provided in minutes; average release percentage ("AR %"); minimum release percentage ("Min-R %"); maximum release percentage ("Max-R %"); and relative standard deviation ("RSD"). In each instance, the sample size used for the dissolution analysis was six (6) chewable gel units, the temperature of the medium was thirty-seven degrees Celsius (37° C.) (±2° C.), and the volume of the medium replenished was ten milliliters (10 ml).

TABLE D34

| Ex # | RT | AR % | Min-R % | Max-R % | RSD |
|---|---|---|---|---|---|
| 7 | 30 | 96 | 89 | 101 | 5.28 |
| 9 | 30 | 93 | 84 | 99 | 5.97 |
| 9 | 45 | 99 | 94 | 104 | 3.9 |
| 10 | 30 | 112 | 108 | 113 | 1.67 |

TABLE D34-continued

| Ex # | RT | AR % | Min-R % | Max-R % | RSD |
|---|---|---|---|---|---|
| 10 | 45 | 114 | 112 | 115 | 1.08 |
| 13 | 30 | 97 | 82 | 106 | 9.37 |
| 13 | 45 | 99 | 85 | 110 | 9.28 |
| 14 | 45 | 116 | 114 | 123 | 2.86 |
| 16 | 45 | 93 | 90 | 96 | — |
| 17 | 30 | 75 | 63 | 86 | — |
| 17 | 45 | 89 | 82 | 98 | — |
| 17 | 60 | 96 | 93 | 101 | — |

Table D35 provides information pertaining to the dissolution analysis of the chewable gel units formed in accordance with the corresponding Examples provided therein after being stored for one hundred eighty (180) days at a temperature of 25° C. and a relative humidity of 60%. Table D35 includes values for: run time ("RT") provided in minutes; average release percentage ("AR %"); minimum release percentage ("Min-R %"); maximum release percentage ("Max-R %"); and relative standard deviation ("RSD"). In each instance, the sample size used for the dissolution analysis was six (6) chewable gel units, the temperature of the medium was thirty-seven degrees Celsius (37° C.) (±2° C.), and the volume of the medium replenished was ten milliliters (10 ml).

TABLE D35

| Ex # | RT | AR % | Min-R % | Max-R % | RSD |
|---|---|---|---|---|---|
| 7 | 30 | 89 | 84 | 93 | 3.68 |
| 9 | 30 | 92 | 80 | 106 | 9.55 |
| 9 | 45 | 98 | 90 | 109 | 7.04 |
| 10 | 30 | 102 | 100 | 104 | 1.36 |
| 10 | 45 | 103 | 101 | 104 | 1.01 |
| 13 | 30 | 101 | 96 | 106 | 3.67 |
| 13 | 45 | 102 | 96 | 107 | 3.58 |
| 14 | 45 | 114 | 111 | 119 | 2.57 |
| 16 | 45 | 92 | 90 | 94 | — |
| 16 | 45 | 104 | 102 | 105 | — |
| 17 | 30 | 59 | 55 | 61 | — |
| 17 | 45 | 77 | 73 | 80 | — |
| 17 | 60 | 87 | 83 | 90 | — |

Dissolution profiles corresponding to the chewable gels formed in accordance with Examples 1, 2, 4-7, 9-11, 13, and 14 are provided in FIGS. 13-23, respectively.

A microbiological characterization analysis of the chewable gel units manufactured in accordance with the Examples provided herein was performed in accordance with USP general chapter <1112>. Table D36 provides information pertaining to the microbiological characterization analysis of the chewable gel units formed in accordance with the corresponding Examples provided therein shortly after the curing step. Table D36 includes values for Water Activity (aw).

TABLE D36

| Ex # | SD | Water Activity (aw) |
|---|---|---|
| 4 | 0 | 0.738 |
| 9 | 0 | 0.592 |
| 9 | 0 | 0.592 |
| 10 | 0 | 0.685 |
| 14 | 0 | 0.687 |
| 16 | 0 | 0.68 |
| 17 | 0 | 0.675 |
| 18 | 0 | 0.65 |
| 19 | 0 | 0.66 |

Table D37 provides information pertaining to the microbiological characterization analysis of the chewable gel units formed in accordance with the corresponding Examples provided therein after being stored for a number of days at a temperature of 25° C. and a relative humidity of 60%. Table D37 includes values for Water Activity (aw).

TABLE D37

| Ex # | SD | Water Activity (aw) |
|---|---|---|
| 4 | 30 | 0.6185 |
| 4 | 90 | 0.644 |
| 7 | 180 | 0.6468 |
| 9 | 180 | 0.645 |
| 10 | 90 | 0.591 |
| 10 | 180 | 0.6759 |
| 13 | 90 | 0.729 |
| 14 | 90 | 0.6768 |
| 14 | 180 | 0.654 |
| 16 | 90 | 0.694 |
| 16 | 180 | 0.6769 |
| 16 | 180 | 0.6782 |
| 17 | 90 | 0.661 |
| 17 | 180 | 0.6459 |
| 18 | 90 | 0.6504 |
| 19 | 90 | 0.67 | le;.4qTable D38 provides information pertaining to the microbiological characterization analysis of the chewable gel units formed in accordance with the corresponding Examples provided therein after being stored for a number of days at a temperature of 40° C. and a relative humidity of 75%. Table D38 includes values for Water Activity (aw).

TABLE D38

| Ex # | SD | Water Activity (aw) |
|---|---|---|
| 4 | 30 | 0.694 |
| 4 | 90 | 0.673 |
| 6 | 30 | 0.644 |
| 7 | 90 | 0.69 |
| 7 | 180 | 0.647 |
| 9 | 30 | 0.591 |
| 9 | 90 | 0.621 |
| 9 | 180 | 0.64 |
| 10 | 30 | 0.574 |
| 10 | 90 | 0.491 |
| 10 | 180 | 0.6804 |
| 13 | 30 | 0.728 |
| 14 | 30 | 0.6672 |
| 14 | 90 | 0.6597 |
| 14 | 180 | 0.643 |
| 16 | 90 | 0.7181 |
| 16 | 180 | 0.698 |
| 17 | 30 | 0.661 |
| 17 | 90 | 0.659 |
| 17 | 180 | 0.6039 |
| 18 | 30 | 0.658 |
| 18 | 90 | 0.6609 |
| 19 | 30 | 0.66 |
| 19 | 90 | 0.67 |

Table D39 provides information pertaining to the microbiological characterization analysis of the chewable gel units formed in accordance with the corresponding Examples provided therein after being stored for a number of days at a temperature of 30° C. and a relative humidity of 65%. Table D39 includes values for Water Activity (aw).

TABLE D39

| Ex # | SD | Water Activity (aw) |
|---|---|---|
| 4 | 30 | 0.692 |
| 4 | 90 | 0.659 |

TABLE D39-continued

| Ex # | SD | Water Activity (aw) |
|---|---|---|
| 13 | 30 | 0.718 |
| 13 | 90 | 0.738 |

A comparative dissolution analysis was conducted using chewable gels formed in accordance with Example 16 hereof and the marketed product Children's Tylenol® lot number C003XH. The parameters for the comparative dissolution analysis are provided in Table D40 and the results are provided in Table D41, which include the average release percentage ("AR %") and relative standard deviation ("RSD").

TABLE D40

| Apparatus | USP apparatus II |
|---|---|
| RPM | 75 |
| Media | Water |
| Volume | 900 ml |
| Temperature | 37° C. |
| Run Time | 45 minutes |

TABLE D41

| | Percent Release | |
|---|---|---|
| Sample # | Example 16 | C003XH |
| 1 | 101 | 97 |
| 2 | 96 | 98 |
| 3 | 98 | 97 |
| 4 | 98 | 97 |
| 5 | 99 | 97 |
| 6 | 97 | 99 |
| AR % | 98 | 98 |
| RSD | 1.75 | 0.86 |

A comparative bioavailability study was conducted using the chewable gels formed in accordance with Example 16 hereof and the marketed product Children's Tylenol® Chewables ("CTC"). This bioavailability study was performed on twelve (12) human subjects in a crossover design for the fasting stage. Pharmacokinetic parameters derived from the comparative bioavailability study are provided in Table D42, including: the maximum serum concentration of the drug (i.e., acetaminophen) achieved in the test area of the body after the drug was administered ("$C_{Max}$"); the area under the curve for a given time period, indicating the time-averaged concentration of the drug circulating in the body fluid analyzed ("$AUC_T$"); the area under the curve from time 0 extrapolated to infinite time ("$AUC_{INF}$"); the amount of time required to achieve maximum drug concentration in plasma ("$T_{Max}$"); the elimination rate constant indicating the rate at which drug fraction is eliminated per unit time at the drug elimination phase ("$K_{el}$"); and the half life of the drug—the amount of time required to achieve half the maximum drug concentration in plasma ("$T_{Half}$"). The "T/R Ratio" provided in Table D42 is the ratio of the "Geometric Mean" of Example 16 for a respective parameter to the "Geometric Mean" of CTC for the corresponding parameter. A plot comparing the mean serum concentration of acetaminophen over a 24-hour period of chewable gels formed in accordance with Example 16 to that of the reference (i.e., CTC) is provided in the chart of FIG. 24.

TABLE D42

| Parameter | Unit | Geometric Mean Example 16 | Geometric Mean CTC | T/R Ratio |
|---|---|---|---|---|
| $C_{Max}$ | ng/ml | 3480.6726 | 3261.2333 | 106.73% |
| $AUC_T$ | hr*ng/mL | 9794.9982 | 9375.0118 | 104.48% |
| $AUC_{INF}$ | hr*ng/mL | 10020.6797 | 9636.5146 | 103.99% |
| $T_{Max}$ | hr | 0.43 | 0.485 | — |
| $K_{el}$ | 1/hr | 0.156 | 0.129 | — |
| $T_{Half}$ | hr | 4.435 | 5.355 | — |

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the description provided above.

What is claimed is:

1. A process for manufacture of a translucent chewable gel that is pharmaceutically suitable for oral administration comprising the steps of:
    (a) preparing a mixture comprising water, a tonicity modifying agent, at least one taste enhancing agent, carrageenan, a buffering agent, a sugar, a non-crystallizing polyol solution, a functional/active ingredient, and a complexing agent; wherein said mixture has a pH of at least 5,
    (b) heating said mixture to a temperature in the range of about 90° C. to about 105° C. until the heated mixture has a total solid content in the range of about 65 brix to about 75 brix to form a gummy mixture; and
    (c) transferring the gummy mixture to a forming device, allowing the gummy mixture to cool in the forming device to form said chewable gel, and removing the chewable gel from the forming device after a period of time of less than 30-minutes.
2. The process as claimed in claim 1, wherein said a tonicity modifying agent comprises sodium chloride.
3. The process as claimed in claim 1, said taste enhancing agent being selected from the group consisting of corn syrup, bitter blocker powder, neotame, sucralose, and combinations thereof.
4. The process as claimed in claim 1, wherein said buffering agent comprises trisodium citrate.
5. The process as claimed in claim 1, wherein said non-crystallizing polyol solution comprises maltitol solution.
6. The process as claimed in claim 1, wherein said complexing agent comprises hydroxypropyl-beta cyclodextrin.
7. The process as claimed in claim 1, said functional/active ingredient comprises one or more active pharmaceutical ingredients.
8. The process as claimed in claim 7,
    said one or more active pharmaceutical ingredients being selected from the group consisting of acetaminophen, aspirin, azithromycin dihydrate, cetirizine hydrochloride, dextromethorphan hydrobromide, dimenhydrinate, diphenhydramine hydrochloride, fexofenadine hydrochloride, guaifenesin, ibuprofen, loratadine, methylphenidate hydrochloride, phenylephrine hydrochloride, and combinations thereof.

9. The process as claimed in claim 1, wherein said chewable gel has an active ingredient concentration in the range of about 0.001% weight-by-weight to about 5% weight-by-weight.

10. The process as claimed in claim 1, wherein said mixture includes a flavor agent.

11. The process as claimed in claim 1, wherein said mixture includes a sugar.

12. The process as claimed in claim 1, said water comprising a first water portion and a second water portion,
step (a) including the steps of:
    combining said functional/active ingredient, said complexing agent, and the first water portion to form solution-1; and
    combining solution-1 with said tonicity modifying agent, said at least one taste enhancing agent, said carrageenan, said buffering agent, said sugar, said non-crystallizing polyol solution, and the second water portion to form said mixture.

13. The process as claimed in claim 12,
step (a) including the steps of:
    combining said tonicity modifying agent, said at least one taste enhancing agent, and said second portion of said water to form solution-2; and
    combining solution-2 with said solution-1, said carrageenan, said buffering agent, said sugar, said non-crystallizing polyol solution to form said mixture.

14. The process as claimed in claim 12,
step (a) including the steps of:
    combining said tonicity modifying agent, said at least one taste enhancing agent, and said second portion of said water to form solution-2; and
    combining solution-2 with said solution-1, said carrageenan, said buffering agent, said sugar, said non-crystallizing polyol solution to form said mixture.

15. The process as claimed in claim 12,
step (a) including the steps of:
    preparing a dry mixture with said carrageenan, said buffering agent, said sugar; and
    combining the dry mixture with said solution-1, said tonicity modifying agent, said at least one taste enhancing agent, said non-crystallizing polyol solution, and the second portion of said water to form said mixture.

* * * * *